(12) United States Patent
Siliphaivanh et al.

(10) Patent No.: US 9,988,397 B2
(45) Date of Patent: Jun. 5, 2018

(54) ERK INHIBITORS

(71) Applicants: Merck Sharp & Dohme Corp., Rahway, NJ (US); MSD R&D (China) Co., Ltd., Shanghai (CN)

(72) Inventors: Phieng Siliphaivanh, Newton, MA (US); David L. Sloman, Brookline, MA (US); David Witter, Norfolk, MA (US); Umar Faruk Mansoor, Framingham, MA (US); Joseph Kozlowski, Princeton, NJ (US); Ziping Liu, Beijing (CN); Jianmin Fu, Beijing (CN); Zhilong Wan, Beijing (CN); Wei Liu, Beijing (CN); Yimin Qian, Plainsboro, NJ (US); Xianhai Huang, Warren, NJ (US)

(73) Assignees: MERCK SHARP & DOHME CORP., Rahway, NJ (US); MSD R&D (CHINA) CO., LTD, Shanghai (CN)

(*) Notice: Subject to any disclaimer, the term of this patent is extended or adjusted under 35 U.S.C. 154(b) by 10 days.

(21) Appl. No.: 15/531,771

(22) PCT Filed: Dec. 10, 2015

(86) PCT No.: PCT/US2015/064861
§ 371 (c)(1),
(2) Date: May 31, 2017

(87) PCT Pub. No.: WO2016/100051
PCT Pub. Date: Jun. 23, 2016

(65) Prior Publication Data
US 2017/0267695 A1    Sep. 21, 2017

(30) Foreign Application Priority Data
Dec. 15, 2014    (WO) ............... PCT/CN2014/093858

(51) Int. Cl.
*C07D 498/18*    (2006.01)
*C07D 471/18*    (2006.01)
*C07D 471/22*    (2006.01)

(52) U.S. Cl.
CPC ......... *C07D 498/18* (2013.01); *C07D 471/18* (2013.01); *C07D 471/22* (2013.01)

(58) Field of Classification Search
CPC .................................................... C07D 498/18
See application file for complete search history.

(56) References Cited

U.S. PATENT DOCUMENTS

| | | |
|---|---|---|
| 2010/0249096 A1 | 9/2010 | Aay et al. |
| 2013/0039906 A1 | 2/2013 | Do et al. |
| 2014/0031360 A1 | 1/2014 | Wang et al. |

FOREIGN PATENT DOCUMENTS

| | | |
|---|---|---|
| WO | 2007070398 A1 | 6/2007 |
| WO | 2008153858 A1 | 12/2008 |
| WO | 2009105500 A1 | 8/2009 |
| WO | 2014186313 A1 | 11/2014 |

*Primary Examiner* — Noble E Jarrell
*Assistant Examiner* — John S Kenyon
(74) *Attorney, Agent, or Firm* — Catherine D. Fitch; Richard S. Parr

(57) ABSTRACT

The present invention provides a compound of Formula (I) or the pharmaceutically acceptable salts, esters, and prodrugs thereof, which are ERK2 inhibitors. The invention also provides a method of inhibiting ERK2 in a patient in need of such treatment comprising administering to said patient an effective amount of at least one compound of Formula (I). The invention also provides a method for treating cancer in a patient in need of such treatment, said method comprising administering to said patient an effective amount of at least one compound of Formula (I).

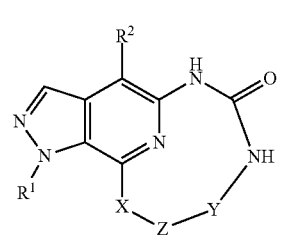

6 Claims, No Drawings

ERK INHIBITORS

This application is a National Stage application of PCT/US2015/064861, filed Dec. 10, 2015, which claims the benefit of PCT Application Serial No. PCT/CN2014/093858, filed Dec. 15, 2014, which is incorporated herein by reference in its entirety.

BACKGROUND OF THE INVENTION

The processes involved in tumor growth, progression, and metastasis are mediated by signaling pathways that are activated in cancer cells. The ERK pathway plays a central role in regulating mammalian cell growth by relaying extracellular signals from ligand-bound cell surface tyrosine kinase receptors such as erbB family, PDGF, FGF, and VEGF receptor tyrosine kinase. Activation of the ERK pathway is via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signalling pathway is an attractive pathway for anticancer therapies in a broad spectrum of human tumors.

Therefore, a welcome contribution to the art would be small-molecules (i.e., compounds) that inhibit ERK activity (ERK2 activity), which small-molecules would be useful for treating a broad spectrum of cancers, such as, for example, melanoma, pancreatic cancer, thyroid cancer, colorectal cancer, lung cancer, breast cancer, and ovarian cancer.

SUMMARY OF THE INVENTION

This invention provides compounds of the Formula I:

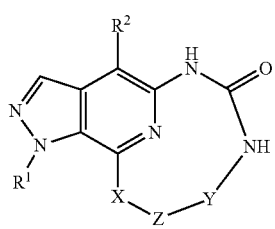

or the pharmaceutically acceptable salts, esters, and prodrugs thereof, which are ERK2 inhibitors.

DETAILED DESCRIPTION OF THE INVENTION

One embodiment of the invention is compounds of formula I

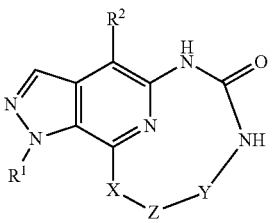

or a pharmaceutically acceptable salt thereof, wherein
$R^1$ is
1) —$C_{1-4}$ alkyl, unsubstituted or substituted with $R^{1'}$, wherein $R^{1'}$ is independently selected from halogen and $OC_{1-4}$ alkyl,
2) 6-membered unsaturated heterocycle having 1 N atom, wherein the heterocycle is unsubstituted or substituted on any ring atom with $C_{1-4}$ alkyl,
3) 6-membered unsaturated carbocycle unsubstituted or substituted on any ring atom with $C_{1-4}$ alkyl, or,
4) —$C(O)C_{1-4}$ alkyl;
$R^2$ is
hydrogen or halogen;
—X—Z is
1) —$C_{1-4}$ alkylene-Z, wherein the alkylene is unsubstituted or substituted with OH, =$CH_2$, —$C_{1-4}$ alkyl, —$C_{1-4}$ alkylene OH, or —$OC_{1-4}$ alkyl,
2)

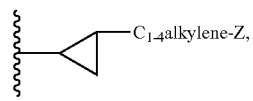

3) —$C_{1-4}$ alkenylene-Z,
4) —$NR^3C_{1-4}$ alkylene-Z,
5) —$OC_{1-4}$ alkylene-Z,
6) —$CH_2NR^3C_{1-4}$ alkylene-Z,
7) —$CH_2C(O)C_{1-4}$ alkylene-Z, or
8) —$CH_2OC_{1-4}$ alkylene-Z;
Z—Y is
O—Y, $C_{1-4}$ alkylene-Y, $NR^3$—Y or

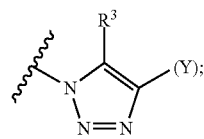

NH—Y is
NH—$CH(C_6H_3R^4R^5)C_{1-4}$ alkylene-, where $C_{1-4}$ alkylene is unsubstituted or independently mono- or di-substituted with $R^6$;
$R^3$ is independently
hydrogen or $C_{1-4}$ alkyl;
$R^4$ is
hydrogen or halogen;
$R^5$ is
hydrogen or —$OC_{1-4}$ alkyl; and
$R^6$ is
OH or $C_{1-4}$ alkyl wherein alkyl is unsubstituted or substituted with OH.

Another embodiment of the invention is compounds of formula I wherein

R$^1$ is
1) —C$_{1-4}$ alkyl, unsubstituted or substituted with R$^{1'}$, wherein R$^{1'}$ is independently selected from F and OC$_{1-4}$ alkyl, or
2) 6-membered unsaturated heterocycle having 1 N atom, wherein the heterocycle is unsubstituted or substituted on any ring atom with C$_{1-4}$ alkyl, R$^2$ is
hydrogen;

—X—Z is
1) —C$_{1-4}$ alkylene-Z, wherein the alkylene is unsubstituted or substituted with OH, =CH$_2$, —CH$_3$, —CH$_2$OH, or —OC$_{1-4}$ alkyl,
2)

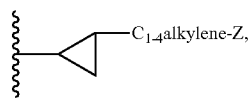

3) —C$_{1-4}$ alkylene-Z,
4) —NR$^3$C$_{1-4}$ alkylene-Z,
5) —OC$_{1-4}$ alkylene-Z,
6) —CH$_2$NR$^3$C$_{1-4}$ alkylene-Z,
7) —CH$_2$C(O)C$_{1-4}$ alkylene-Z, or
8) —CH$_2$OC$_{1-4}$ alkylene-Z;

Z—Y is
O—Y, C$_{1-4}$ alkylene-Y, NR$^3$—Y or

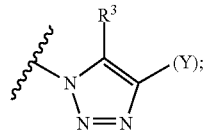

NH—Y is
NH—CH(C$_6$H$_3$R$^4$R$^5$)C$_{1-4}$ alkylene-, where C$_{1-4}$ alkylene is unsubstituted or independently mono- or di-substituted with R$^6$;

R$^3$ is independently
hydrogen or C$_{1-4}$ alkyl;
R$^4$ is
hydrogen or F;
R$^5$ is
hydrogen or —OC$_{1-4}$ alkyl; and
R$^6$ is
OH or C$_{1-4}$ alkyl wherein alkyl is unsubstituted or substituted with OH.

Another embodiment of the invention is compounds of formula I wherein
R$^1$ is
—CH$_2$CH$_3$, —CHF$_2$, —CH$_3$, —(CH$_2$)$_3$OCH$_3$, —(CH$_2$)$_2$OCH$_3$, or

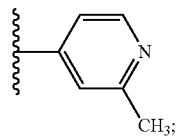 [SMILES: *c1ccnc(C)c1]

R$^2$ is
hydrogen;

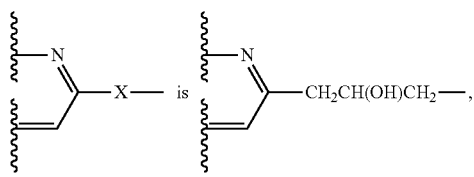

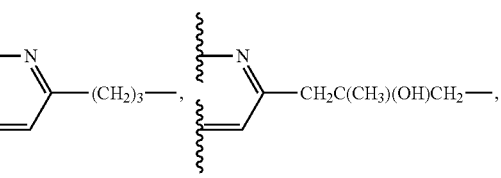

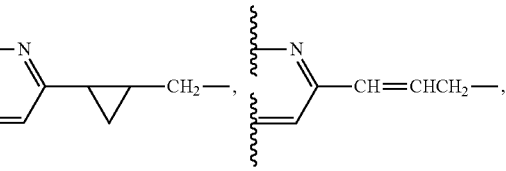

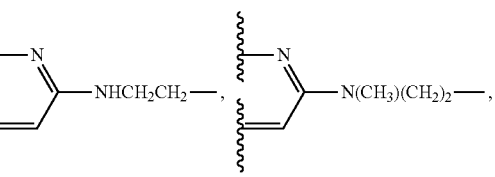

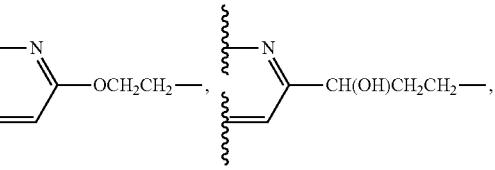

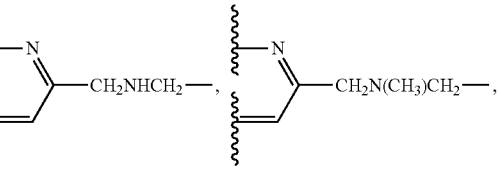

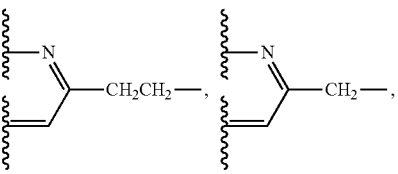

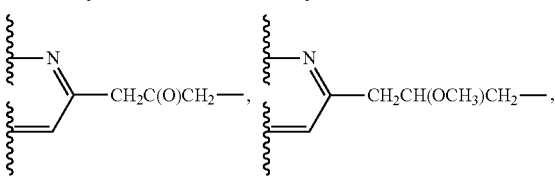

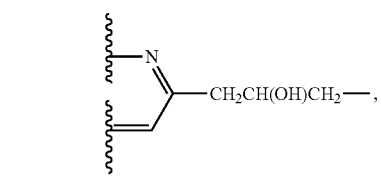

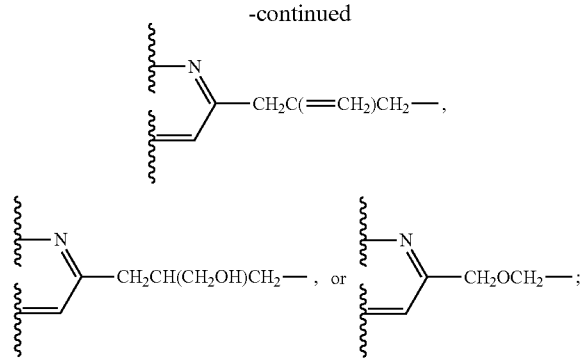

Z is
O, CH$_2$, N(CH$_3$),

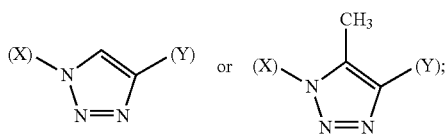

and
NH—Y— is
NH—CH(C$_6$H$_5$)CH$_2$—, NH—CH(C$_6$H$_5$)CH(OH),
NH—CH(C$_6$H$_5$)C(OH)(CH$_3$)—,
NH—CH(C$_6$H$_5$)C(CH$_3$)$_2$—, NH—CH(C$_6$H$_5$)CH(CH(OH)(CH$_3$)), or
NH—CH(C$_6$H$_3$(F)(OCH$_3$))CH$_2$—.

The term "composition" is intended to encompass a product comprising the specified ingredients in the specified amounts, as well as any product which results, directly or indirectly, from combination of the specified ingredients in the specified amounts. The term "anti-cancer agent" means a drug (medicament or pharmaceutically active ingredient) for treating cancer. The term "antineoplastic agent" means a drug (medicament or pharmaceutically active ingredient) for treating cancer (i.e., a chemotherapeutic agent). The term "at least one" means one or more than one. The meaning of "at least one" with reference to the number of compounds of the invention is independent of the meaning with reference to the number of chemotherapeutic agents. The term "chemotherapeutic agent" means a drug (medicament or pharmaceutically active ingredient) for treating cancer (i.e., and antineoplastic agent). The term "compound" with reference to the antineoplastic agents, includes the agents that are antibodies. The term "consecutively" means one following the other. The term "effective amount" means a "therapeutically effective amount". The term "therapeutically effective amount" means that amount of active compound or pharmaceutical agent that elicits the biological or medicinal response in a tissue, system, animal or human that is being sought by a researcher, veterinarian, medical doctor or other clinician. Thus, for example, in the methods of treating cancer described herein "effective amount" (or "therapeutically effective amount") means, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. Also, for example, an effective amount, or a therapeutically effective amount of the ERK inhibitor (i.e., a compound of the invention) is that amount which results in the reduction in ERK (ERK2) activity and phosphorylation. The reduction in ERK activity may be determined by the analysis of pharmacodynamic markers such as phosphorylated RSK1,2 using techniques well known in the art. The term "treating cancer" or "treatment of cancer" refers to administration to a mammal afflicted with a cancerous condition and refers to an effect that alleviates the cancerous condition by killing the cancerous cells, and also refers to an effect that results in the inhibition of growth and/or metastasis of the cancer.

The invention also provides a pharmaceutical composition comprising an effective amount of at least one compound of Formula I and a pharmaceutically acceptable carrier. The invention also provides a pharmaceutical composition comprising an effective amount of at least one compound of Formula I and an effective amount of at least one other pharmaceutically active ingredient (such as, for example, a chemotherapeutic agent), and a pharmaceutically acceptable carrier.

The invention also provides a method of inhibiting ERK2 in a patient in need of such treatment comprising administering to said patient an effective amount of at least one compound of Formula I. The invention also provides a method for treating cancer in a patient in need of such treatment, said method comprising administering to said patient an effective amount of at least one compound of Formula I. The invention also provides a method for treating cancer in a patient in need of such treatment, said method comprising administering to said patient an effective amount of at least one compound of Formula I, in combination with an effective amount of at least one chemotherapeutic agent. The methods of the invention include the administration of a pharmaceutical composition comprising at least one compound of the invention and a pharmaceutically acceptable carrier. The invention also provides any of the above methods of treating cancer wherein the cancer is colorectal. The invention also provides any of the above methods of treating cancer wherein the cancer is melanoma. The methods of treating cancers described herein can optionally include the administration of an effective amount of radiation (i.e., the methods of treating cancers described herein optionally include the administration of radiation therapy).

The methods of treating cancer described herein include methods of treating cancer that comprise administering a therapeutically effective amount of a compound of the instant invention in combination with radiation therapy and/or in combination with a second compound selected from: an estrogen receptor modulator, an androgen receptor modulator, a retinoid receptor modulator, a cytotoxicicytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed herein.

In any of the methods of treating cancer described herein, unless stated otherwise, the methods can optionally include the administration of an effective amount of radiation therapy. For radiation therapy, γ-radiation is preferred.

Thus, another example of the invention is directed to a method of treating cancer in a patient in need of such treatment, said method comprising administering an effective amount of a compound of Formula I. Another example of the invention is directed to a method of treating cancer in a patient in need of such treatment, said method comprising administering to said patient an effective amount of a compound of Formula I, and an effective amount of at least one chemotherapeutic agent.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physicians' Desk Reference, 56$^{th}$ Edition, 2002 (published by Medical Economics company, Inc. Montvale, N.J. 07645-1742), the Physicians' Desk Reference, 57$^{th}$ Edition, 2003 (published by Thompson PDR, Montvale, N.J. 07645-1742), the Physicians' Desk Reference, 60$^{th}$ Edition, 2006 (published by Thompson PDR, Montvale, N.J. 07645-1742), and the Physicians' Desk Reference, 64$^{th}$ Edition, 2010 (published by PDR Network, LLC at Montvale, N.J. 07645-1725); the disclosures of which are incorporated herein by reference thereto.

If the patient is responding, or is stable, after completion of the therapy cycle, the therapy cycle can be repeated according to the judgment of the skilled clinician. Upon completion of the therapy cycles, the patient can be continued on the compounds of the invention at the same dose that was administered in the treatment protocol. This maintenance dose can be continued until the patient progresses or can no longer tolerate the dose (in which case the dose can be reduced and the patient can be continued on the reduced dose).

Those skilled in the art will recognize that the actual dosages and protocols for administration employed in the methods of the invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula (1) and the chemotherapeutic agents will be regulated according to the judgment of the attending clinician (physician) considering such factors as age, condition and size of the patient as well as severity of the cancer being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of a chemotherapeutic agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MM scan, and successive measurements can be used to judge whether or not growth of the tumor has been retarded or even reversed. Relief of disease-related symptoms such as pain, and improvement in overall condition can also be used to help judge effectiveness of treatment.

The compounds, compositions and methods provided herein are useful for the treatment of cancer. Cancers that may be treated by the compounds, compositions and methods of the invention include, but are not limited to: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; (9) Hematologic: blood (myeloid leukemia [acute and chronic], acute lymphoblastic leukemia, chronic lymphocytic leukemia, chronic myelomonocytic (CMML), myeloproliferative diseases, multiple myeloma, myelodysplastic syndrome), Hodgkin's disease, non-Hodgkin's lymphoma [malignant lymphoma]; (10) Skin: malignant melanoma, basal cell carcinoma, squamous cell carcinoma, Karposi's sarcoma, moles dysplastic nevi, lipoma, angioma, dermatofibroma, keloids, psoriasis; and (11) Adrenal glands: neuroblastoma. Examples of cancer that may be treated by the compounds, compositions and methods of the invention include thyroid cancer, anaplastic thyroid carcinoma, epidermal cancer, head and neck cancer (e.g., squamous cell cancer of the head and neck), sarcoma, tetracarcinoma, hepatoma and multiple myeloma. Thus, the term "cancerous cell" as provided herein, includes a cell afflicted by any one of the above-identified conditions.

In the treatment of breast cancer (e.g., postmenopausal and premenopausal breast cancer, e.g., hormone-dependent breast cancer) the compound of formula (1) may be used with an effective amount of at least one antihormonal agent selected from the group consisting of: (a) aromatase inhibitors, (b) antiestrogens, and (c) LHRH analogues; and optionally an effective amount of at least one chemotherapeutic agent. Examples of aromatase inhibitors include but are not limited to: Anastrozole (e.g., Arimidex), Letrozole (e.g., Femara), Exemestane (Aromasin), Fadrozole and Formestane (e.g., Lentaron). Examples of antiestrogens include but are not limited to: Tamoxifen (e.g., Nolvadex), Fulvestrant (e.g., Faslodex), Raloxifene (e.g., Evista), and Acolbifene. Examples of LHRH analogues include but are not limited to: Goserelin (e.g., Zoladex) and Leuprolide (e.g., Leuprolide Acetate, such as Lupron or Lupron Depot). Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

In one example of the invention the cancer treated is colo-rectal cancer (such as, for example, colon adenocarcinoma and colon adenoma). Thus, another example of the invention is directed to a method of treating colo-rectal cancer in a patient in need of such treatment, said method comprising administering an effective of a compound of Formula I, or a pharmaceutically acceptable salt thereof, to said patient. Another example of the invention is directed to a method of treating colo-rectal cancer in a patient in need of such treatment, said method comprising administering to said patient an effective amount of a compound of Formula I, or a pharmaceutically acceptable salt thereof, and an effective amount of at least one chemotherapeutic agent.

In one example of the invention the cancer treated is melanoma. Thus, another example of the invention is directed to a method of treating melanoma in a patient in need of such treatment, said method comprising administering an effective amount of a compound of Formula I, or a pharmaceutically acceptable salt thereof, to said patient. Another example of the invention is directed to a method of treating melanoma in a patient in need of such treatment, said method comprising administering to said patient an effective amount of a compound of Formula I, or a pharmaceutically acceptable salt thereof, and an effective amount of at least one chemotherapeutic agent.

The compounds of the invention are also useful in preparing a medicament that is useful in treating cancer.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, programmed cell death protein 1 (PD-1) inhibitors, programmed death-ligand 1 (PD-L1) inhibitors, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

PD-1 inhibitors include pembrolizumab (lambrolizumab), nivolumab and MPDL3280A.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, TDX258, the epothilones (see for example U.S. Pat. Nos. 6,284,781 and 6,288,237) and BMS188797. In an example the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydroOxy-3,5-dimethoxyphenyl]-5,5a,6,8,8a,9-hexohydrofuro(3',4':6,7) naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an example inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. J. Med. Chem. 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl) sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273, 995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of the invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101: 329-354 (2001)). TAFIa inhibitors have been described in U.S. Ser. Nos. 60/310,927 (filed Aug. 8, 2001) and 60/349, 925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK1 and CHK2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, Nature, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734188, 60/652737, 60/670469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of the specification an NSAID is potent if it possesses an $IC_{50}$ for the inhibition of COX-2 of 1 μM or less as measured by cell or microsomal assays.

The invention also encompasses combinations with NSAID's which are selective COX-2 inhibitors. For purposes of the specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344, 991, 5,134,142, 5,380,738, 5,393,790, 5,466,823, 5,633,272 and No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl) phenyl]methyl]-1H-1,2,3-triazole-4-carboxamide,CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274:9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235, 708 and 60/244,697).

Another example of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another example, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913,0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an example, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, Cl1033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with PARP inhibitors.

A compound of the instant invention may also be useful for treating cancer in combination with the following therapeutic agents: pembrolizumab (Keytruda®), abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); DROMOSTANOLONE PROPIONATE (DROMOSTANOLONE®); DROMOSTANOLONE PROPIONATE (MASTERONE INJECTION®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); Ridaforolimus; sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®) and zoledronate (Zometa®).

In an example, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an example, the estrogen receptor modulator is tamoxifen or raloxifene.

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

And yet another example of the invention is a method of treating cancer that comprises administering a therapeutically effective amount of a compound of the instant invention in combination with paclitaxel or trastuzumab.

The invention further encompasses a method of treating or preventing cancer that comprises administering a therapeutically effective amount of a compound of the instant invention in combination with a COX-2 inhibitor.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

When any variable occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is bicyclic, it is intended that the bond be attached to any of the suitable atoms on either ring of the bicyclic moiety.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. Also, "optionally substituted" means optional substitution with the specified groups, radicals or moieties.

It will be understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of the invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemi sulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of the invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of the invention are capable of tautomerization, all individual tautomers as well as mixtures thereof are included in the scope of the invention. The present invention includes all such isomers, as well as salts, solvates (including hydrates) and solvated salts of such racemates, enantiomers, diastereomers and tautomers and mixtures thereof In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of the invention, along with unsolvated and anhydrous forms.

Reference to the compounds of the invention as those of a specific formula or embodiment, e.g., Formula I or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

Except where noted herein, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or CH$_3$ or a symbol that is an extended bond as the terminal group, e.g.

ethyl may be represented by "Et" or CH$_2$CH$_3$, propyl may be represented by "Pr" or CH$_2$CH$_2$CH$_3$, butyl may be represented by "Bu" or CH$_2$CH$_2$CH$_2$CH$_3$, etc. "C$_{1-4}$ alkyl" (or "C$_1$-C$_4$ alkyl") for example, means linear or branched chain alkyl groups, including all isomers, having the specified number of carbon atoms. For example, the structures

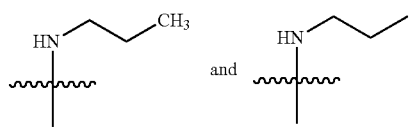

have equivalent meanings. C$_{1-4}$ alkyl includes n-, iso-, sec- and t-butyl, n- and isopropyl, ethyl and methyl. If no number is specified, 1-4 carbon atoms are intended for linear or branched alkyl groups.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically acceptable salts.

Any pharmaceutically acceptable pro-drug modification of a compound of the invention which results in conversion in vivo to a compound within the scope of the invention is also within the scope of the invention. For example, esters can optionally be made by esterification of an available carboxylic acid group or by formation of an ester on an available hydroxy group in a compound. Similarly, labile amides can be made. Pharmaceutically acceptable esters or amides of the compounds of the invention may be prepared to act as prodrugs which can be hydrolyzed back to an acid (or —COO— depending on the pH of the fluid or tissue where conversion takes place) or hydroxy form particularly in vivo and as such are encompassed within the scope of the invention. Examples of pharmaceutically acceptable prodrug modifications include, but are not limited to, —C$_{1-6}$alkyl esters and —C$_{1-6}$alkyl substituted with phenyl esters.

When any variable occurs more than one time in any constituent or in formula I, its definition on each occurrence is independent of its definition at every other occurrence. Also, combinations of substituents and/or variables are permissible only if such combinations result in stable compounds.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Except where noted herein, alkyl groups may be unsubstituted, or substituted with 1 to 3 substituents on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_0$-$C_6$ alkyl)C(O)NH—, $H_2$N—C(NH)—, —O($C_1$-$C_6$ alkyl)$CF_3$, HC(O)—, ($C_1$-$C_6$ alkyl)C(O)—, HOC(O)—, ($C_1$-$C_6$ alkyl)OC(O)—, HO($C_1$-$C_6$ alkyl)-, ($C_1$-$C_6$ alkyl)O($C_1$-$C_6$ alkyl)-, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$—, HOC(O)NH—, ($C_1$-$C_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Except where noted, the term "halogen" means fluorine, chlorine, bromine or iodine.

Except where noted, the term saturated "heterocycle" refers to a stable 4- to 7-membered mono-cyclic or stable 7- to 12-membered bicyclic or stable 12- to 14-membered tricyclic heteroatom-containing ring system unsubstituted or substituted with $C_{1-4}$ alkyl or halogen, and which consists of carbon atoms and from one to four heteroatoms independently selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Representative examples include azetidine, oxetane, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, oxane, thiane, piperazine, morpholine, thiomorpholine, dioxane, dithiane, trioxane, trithiane, azepane, oxepane, thiepane, and homopiperazine.

Except where noted herein, the term unsaturated "heterocycle" refers to a monocyclic unsaturated heterocycle having a specified number of atom members (e.g., 4, 5, 6 or 7-membered), including a specified number of heteroatoms (e.g., 1, 2, 3 or 4 heteroatoms independently selected from N, O or S), or a bicyclic unsaturated ring system having a specified number of atom members (e.g., 7, 8, 9, 10, 11 or 12-membered) including a specified number of heteroatoms (e.g., 1, 2, 3, 4, 5, 6, 7, 8, 9 or 10 heteroatoms independently selected from N, S or O) or a tricyclic unsaturated ring system having a specified number of atom members (e.g., 12-, 13- or 14-membered) including a specified number of heteroatoms (e.g., 1, 2, 3, 4, 5, 6, 7, 8, 9 or 10 heteroatoms independently selected from N, S or O) e.g., 5-membered rings containing one nitrogen (pyrrole), one oxygen (furan) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen (triazole) atoms, five-membered aromatic rings containing one oxygen, one nitrogen or one sulfur atom, five-membered aromatic rings containing two heteroatoms independently selected from oxygen, nitrogen and sulfur (e.g., oxazole), 6-membered rings containing one nitrogen (pyridine), or one oxygen (pyran) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Additional examples are pyridine, pyrimidine, thiophene, imidazole, isothiazole, oxadiazole, and isoxazole.

Except where noted herein, the term "unsaturated bicyclic heterocycle" or "unsaturated tricyclic heterocycle" refers to a heterocycle having fused rings in which at least one of the rings is not fully saturated, e.g.

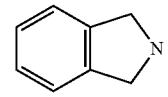

is a 9-membered unsaturated bicyclic heterocycle having one nitrogen atom.

Except where noted herein, the term "carbocycle" (and variations thereof such as "carbocyclic" or "carbocyclyl") as used herein, unless otherwise indicated, refers to a $C_3$ to $C_8$ monocyclic saturated or unsaturated ring, e.g., $C_{3-8}$ monocyclic carbocycle, or a $C_9$ to $C_{12}$ bicyclic saturated or unsaturated ring, e.g., $C_{9-12}$ bicyclic carbocycle. The carbocycle may be attached to the rest of the molecule at any carbon atom which results in a stable compound. Saturated carbocyclic rings include, for example, "cycloalkyl" rings, e.g., cyclopropyl, cyclobutyl, etc. Unsaturated carbocyclic rings include, for example, "aryl" rings. Unsaturated bicyclic carbocyclic ring systems include fused ring systems where all ring system members are carbon atoms and where at least one of the fused rings is not saturated.

Except where noted herein, the term "unsaturated bicyclic carbocycle" or "unsaturated tricyclic carbocycle" refers to a carbocycle having fused rings in which at least one of the rings is not fully saturated, e.g.

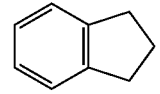

is a 9-membered unsaturated bicyclic carbocycle.

Except where noted, the term "aryl" refers to a stable 6- to 10-membered mono- or bicyclic unsaturated carbocyclic ring system such as phenyl, or naphthyl. The aryl ring can be unsubstituted or substituted with one or more of $C_{1-4}$ alkyl, hydroxyl, alkoxy, halogen, or amino.

"Celite®" (Fluka) diatomite is diatomaceous earth, and can be referred to as "celite".

Except where noted herein, carbocycle groups may be unsubstituted, or substituted on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, HS(O)$_{0-2}$—, ($C_1$-$C_6$ alkyl)S(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$, ($C_1$-$C_6$ alkyl)C(O)NH—, HC(O)NH—, $H_2$N—C(NH)—, —O($C_1$-$C_6$ alkyl)$CF_3$, ($C_1$-$C_6$ alkyl)C(O)—, HC(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)C(O)$_{1-2}$($C_1$-$C_6$ alkyl)-, ($C_1$-$C_6$ alkyl)C(O)$_{1-2}$—, HC(O)$_{1-2}$ ($C_1$-$C_6$ alkyl)-, ($C_1$-$C_6$ alkyl)OC(O)NH—, HOC(O)NH—, —P(O)(OH)$_2$, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Except where noted herein, heterocycles may be unsubstituted, or substituted on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$ ($C_1$-$C_6$ alkyl)-, HS(O)$_{0-2}$($C_1$-$C_6$ alkyl)-, ($C_1$-$C_6$ alkyl)S(O)$_{0-2}$—, ($C_1$-$C_6$ alkyl)C(O)NH—, HC(O)NH—, $H_2N$—C(NH)—, —O($C_1$-$C_6$ alkyl)$CF_3$, HC(O)—, ($C_1$-$C_6$ alkyl)C(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)O—, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$, ($C_1$-$C_6$ alkyl)OC(O)NH—, HOC(O)NH—, silyl groups (including trimethylsilyl, tetramethylsilyl, or supersilyl groups such as tri(trimethylsilyl)silyl or a silicon group connected to tert butyl groups), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, or independently or additionally substituted with 1 substituent on any one or more nitrogen atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, —C(O)$C_{1-6}$ alkyl, —C(O)NH$C_1$-$C_6$ alkyl, —C(O) NH$_2$, —$C_1$-$C_6$ alkylC(O)NH$_2$, —$C_1$-$C_6$ alkylOC(O)NH$_2$, or independently or additionally substituted with 1 substituent on any one or more sulfur atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, where such substitution results in formation of a stable compound.

Except where noted herein, structures containing substituent variables such as variable "R" below:

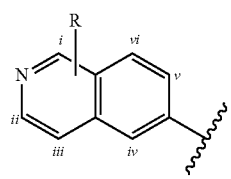

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also includes derivatives of the compound of Formula I, acting as prodrugs and solvates. Prodrugs, following administration to the patient, are converted in the body by normal metabolic or chemical processes, such as through hydrolysis in the blood, to the compound of Formula 1. Such prodrugs include those that demonstrate enhanced bioavailability, tissue specificity, and/or cellular delivery, to improve drug absorption of the compound of Formula I. The effect of such prodrugs may result from modification of physicochemical properties such as lipophilicity, molecular weight, charge, and other physicochemical properties that determine the permeation properties of the drug.

The preparation of pharmacologically acceptable salts from compounds of the Formula (I) capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula (I) form stable alkali metal, alkaline earth metal or optionally substituted ammonium salts. If the compounds of the Formula (I) have basic groups, stable acid addition salts can also be prepared using strong acids. For the, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments containing at least one compound of the Formula (I) and/or of a pharmaceutically acceptable salt of the compound of the Formula (I) and/or an optionally stereoisomeric form of the compound of the Formula (I) or a pharmaceutically acceptable salt of the stereoisomeric form of the compound of Formula (I), together with a pharmaceutically suitable and pharmaceutically acceptable vehicle, additive and/or other active substances and auxiliaries.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the compounds, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specificed otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the compounds may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

The compounds of the invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes do not necessarily correlate to that used in the claims and often, for clarity, a single substituent is shown attached to the compound where multiple sub stituents are optionally allowed under the definitions of Formula I hereinabove.

TLC is thin layer chromatography; Ts is tosyl; UV is ultraviolet; W is watts; wt. % is percentage by weight; xg is times gravity; $\alpha_D$ is the specific rotation of polarized light at 589 nm; ° C. is degrees Celsius; % w/v is percentage in weight of the former agent relative to the volume of the latter agent.

Methods for Making the Compounds of Present Invention
General Methods

The compounds of the present invention can be readily produced from known compounds or commercially available compounds by, for example, known processes described in published documents, and produced by production processes described below. The present invention is not limited to the production processes described below. The invention also includes processes for the preparation of compounds of the invention.

It should be noted that, when compounds of the present invention synthesized has a reactive group such as hydroxy group, amino group, carboxyl group, or thiol group as its substituent, such group may be adequately protected with a protective group in each reaction step and the protective group may be removed at an adequate stage. The process of such introduction and removal of the protective group may be adequately determined depending on the group to be protected and the type of the protective group, and such introduction and removal are conducted, for example, by the process described in the review section of Greene, T. W., et. al., *"Protective Groups in Organic Synthesis"*, 2007, 4th Ed., Wiley, New York, or Kocienski, P., *"Protecting Groups"* 1994, Thieme.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claim.

General Methods

All solvents used were commercially available and were used without further purification. Reactions were typically run using anhydrous solvents under an inert atmosphere of nitrogen.

$^1$H spectra were recorded at 300 or 400 MHz for proton on a Bruker Mercury Plus 400 NMR Spectrometer equipped with a Bruker 400 BBO probe. All deuterated solvents contained typically 0.03% to 0.05% v/v tetramethylsilane, which was used as the reference signal (set at δ 0.00 for both $^1$H and $^{13}$C).

LCMS analyses were performed on a SHIMADZU LCMS consisting of an UFLC 20-AD and LCMS 2020 MS detector. The column used was a Shim-pack XR-ODS, 2.2 μm, 3.0×50 mm. A linear gradient was applied, starting at 95% A (A: 0.05% TFA in water) and ending at 100% B (B: 0.05% TFA in MeCN) over 2.2 min with a total run time of 3.6 min. The column temperature was at 40° C. with the flow rate of 1.0 mL/min. The Diode Array Detector was scanned from 200-400 nm. The mass spectrometer was equipped with an electrospray ion source (ES) operated in a positive or negative mode.

HPLC analyses were performed on a SHIMADZU UFLC with two LC20 AD pump and a SPD-M20A Photodiiode Array Detector. The column used was an)(Bridge $C_{18}$, 3.5 μm, 4.6×100 mm. A linear gradient was applied, starting at 90% A (A: 0.05% TFA in water) and ending at 95% B (B: 0.05% TFA in MeCN) over 10 min with a total run time of 15 min. The column temperature was at 40° C. with the flow rate of 1.5 mL/min. The Diode Array Detector was scanned from 200-400 nm.

Thin layer chromatography (TLC) was performed on Alugram® (Silica gel 60 $F_{254}$) from Mancherey-Nagel and UV was typically used to visualize the spots. Additional visualization methods were also employed in some cases. In these cases the TLC plate was developed with iodine (generated by adding approximately 1 g of $I_2$ to 10 g silica gel and thoroughly mixing), ninhydrin (available commercially from Aldrich), or Magic Stain (generated by thoroughly mixing 25 g $(NH_4)_6Mo_7O_{24}\cdot 4H_2O$, 5 g $(NH_4)_2Ce(IV)(NO_3)_6$ in 450 mL water and 50 mL concentrated $H_2SO_4$) to visualize the compound. Flash chromatography was preformed using 40-63 μm (230-400 mesh) silica gel from Silicycle following analogous techniques to those disclosed in Still, W. C.; Kahn, M.; and Mitra, M. *Journal of Organic Chemistry*, 1978, 43, 2923. Typical solvents used for flash chromatography or thin layer chromatography were mixtures of chloroform/methanol, dichloromethane/methanol, ethyl acetate/methanol and petroleum ether/ethyl acetate.

Preparative HPLC was performed on either a Waters Prep LC 4000 System using a Waters 2487 Diode Array or on a Waters LC Module 1 plus. The column used was SunFire Prep C18 OBD Column, 5 μm, 19×150 mm. Narrow gradients with acetonitrile/water, with the water containing either 0.1% trifluoroacetic acid or 0.1% $NH_4HCO_3$, were used to elute the compound at a flow rate of 20 mL/min and a total run time between 20-30 min. Detector, 254 nm, 220 nm.

Chiral HPLC conditions: Column, Chiralpak IA, 5 μm, 20×150 mm; Mobile phase, Hex/EtOH or IPA; Detector, 254 nm, 220 nm.

The following abbreviations have been used:
AcOH acetic acid
aq. aqueous
BINAP 2,2'-bis(diphenylphosphino)-1,1'-binaphthyl
Boc tert-butyloxycarbonyl
$Boc_2O$ di-tert-butyl dicarbonate
BrettPhos Precatalyst
DCM dichloromethane
DIEA diisopropylethylamine
DMAP 4-dimethylaminopyridine
DMF N,N-dimethylformamide
DMSO dimethylsulfoxide
EtOAc ethyl acetate
EI electron ionization
equiv. equivalent
EtOH ethanol
HPLC high performance liquid chromatography
IBX 2-iodoxybenzoic acid
J coupling constant
LCMS liquid chromatography-mass spectometry
m-CPBA m-chloroperoxybenzoic acid
MeOH methanol
MeCN acetonitrile
MS mass spectrometry
NMR nuclear magnetic resonance
Prep-TLC preparative thin layer chromatography
pTsOH p-toluenesulfonic acid
TEA triethylamine
TFA trifluoroacetic acid
THF tetrahydrofuran
TMSCl trimethylchlorosilane Starting materials used were either available from commercial sources or prepared according to literature procedures and had experimental data in accordance with those reported.

In the schemes and examples, unless otherwise indicated, R is unsubstituted or substituted $C_{1-4}$ alkyl substituted with halogen and/or $-OC_{1-4}$ alkyl, or unsubstituted or substituted unsaturated heterocycle, wherein substitution includes $C_{1-4}$ alkyl and/or halogen; and R' is $C_6H_3R^4R^5$, wherein $R^4$ is H or halogen and $R^5$ is H or $-OC_{1-4}$ alkyl.

INTERMEDIATES

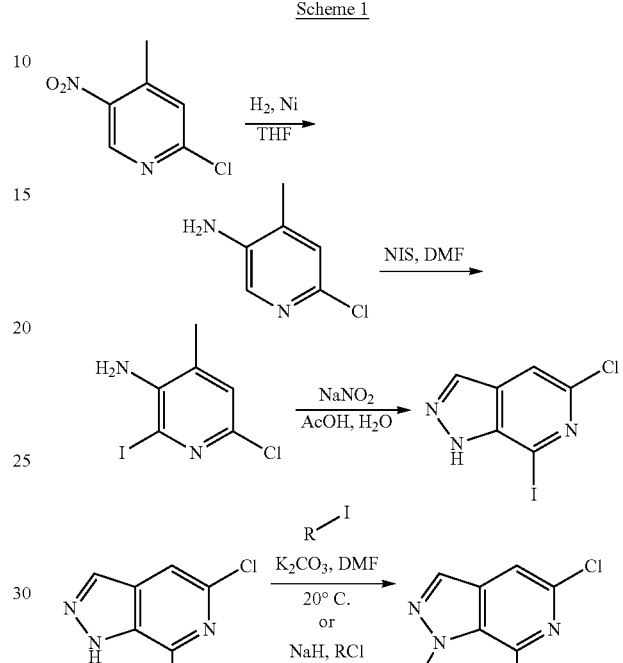

Scheme 1

Intermediate I

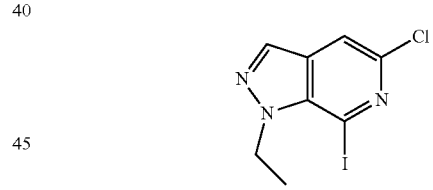

5-Chloro-1-ethyl-7-iodo-1H-pyrazolo[3,4-c]pyridine

Step 1: 6-Chloro-4-methylpyridin-3-amine

To a solution of 2-chloro-4-methyl-5-nitropyridine (200 g, 1.16 mol) in THF (1000 mL) was added Raney-nickel (68.0 g, 1.16 mol) in portions. The resulting mixture was purged in 2-4 atm. hydrogen and stirred for 16 h at 25° C. under an atmosphere of hydrogen (2~4 atm.). The reaction mixture was filtered, and the filtrate was concentrated under vacuum to give 6-chloro-4-methylpyridin-3-amine, which was used directly for the next step without further purification. MS (EI) calc'd for $C_6H_8ClN_2$ $[M+H]^+$ 143, found 143.

Step 2: 6-Chloro-2-iodo-4-methylpyridin-3-amine

To a solution of 6-chloro-4-methylpyridin-3-amine (100 g, 701 mmol) in DMF (1000 mL) was added 1-iodopyrrolidine-2,5-dione (189 g, 842 mmol) in portions. The mixture was stirred for 10 h at 25° C. and then concentrated under reduced pressure. The residue was diluted with water and extracted with EtOAc, washed with brine, dried (Na$_2$SO$_4$), filtered and concentrated. The residue was purified by chromatography on SiO$_2$, eluted with petroleum ether/EtOAc (10:1) to give 6-chloro-2-iodo-4-methylpyridin-3-amine. MS (EI) calc'd for C$_6$H$_7$ClIN$_2$ [M+H]$^+$ 269, found 269.

Step 3: 5-Chloro-7-iodo-1H-pyrazolo[3,4-c]pyridine

To a solution of 6-chloro-2-iodo-4-methylpyridin-3-amine (80 g, 298 mmol) in AcOH (500 mL) was added a solution of sodium nitrite (22.61 g, 328 mmol) in water (200 mL) in portions at 0° C. The resulting mixture was stirred for 10 h at 25° C. and concentrated under vacuum and diluted with water. The pH value of the solution was adjusted to 7 with saturated NaHCO$_3$ and then extracted with DCM, washed with brine, dried (Na$_2$SO$_4$), filtered and concentrated to give 5-chloro-7-iodo-1H-pyrazolo[3,4-c]pyridine. MS (EI) calc'd for C$_6$H$_4$ClIN$_3$ [M+H]$^+$ 280, found 280.

Step 4: 5-Chloro-1-ethyl-7-iodo-1H-pyrazolo[3,4-c]pyridine

To a solution of 5-chloro-7-iodo-1H-pyrazolo[3,4-c]pyridine (5 g, 17.89 mmol) in DMF (50 mL) were added K$_2$CO$_3$ (4.95 g, 35.8 mmol) and iodoethane (2.79 g, 17.89 mmol). The resulting solution was stirred for 2 h at 25° C. and then concentrated under vacuum. The residue was diluted with DCM, washed with water, dried (Na$_2$SO$_4$), filtered and concentrated. The residue was purified by chromatography on SiO$_2$, eluted with petroleum ether/EtOAc (10:1) to give the desired isomer 5-chloro-1-ethyl-7-iodo-1H-pyrazolo[3,4-c]pyridine. MS (EI) calc'd for C$_8$H$_8$ClIN$_3$ [M+H]$^+$ 308, found 308; $^1$H NMR (300 MHz, CDCl$_3$) 8.02 (s, 1 H), 7.57 (s, 1 H), 4.89 (q, J=7.2 Hz, 2 H), 1.53 (t, J=7.2 Hz, 3 H).

| Intermediate # | Structure | IUPAC Name | Exact Mass [M + H]+ |
|---|---|---|---|
| II | 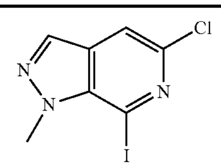 | 5-Chloro-1-methyl-7-iodo-1H-pyrazolo[3,4-c]pyridine | Calc'd 294, found 294 |

Intermediate III

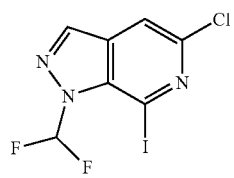 [SMILES: FC(F)n1ncc2cc(Cl)nc(I)c21]

5-Chloro-1-(difluoromethyl)-7-iodo-1H-pyrazolo[3,4-c]pyridine

To a cooled (0° C.) mixture of sodium hydride (4.29 g, 107 mmol) (60% in mineral oil) in THF (150 mL) was added 5-chloro-7-iodo-1H-pyrazolo[3,4-c]pyridine, step 3 from intermediate 1 synthesis, (10.0 g, 35.8 mmol) and the mixture was stirred at 25° C. for 30 min. Then chlorodifluoromethane (6.19 g, 71.6 mmol) was added. After stirring for 4 h at 25° C., the reaction mixture was quenched with water, extracted with EtOAc, then washed with brine, dried (Na$_2$SO$_4$), filtered and concentrated under reduced pressure. The residue was purified by chromatography on SiO$_2$, eluted with petroleum ether/EtOAc (10:1) to give 5-chloro-1-(difluoromethyl)-7-iodo-1H-pyrazolo[3,4-c]pyridine (750 mg). MS (EI) calc'd for C$_7$H$_4$ClF$_2$IN$_3$ [M+H]$^+$ 330, found 330.

Scheme 2

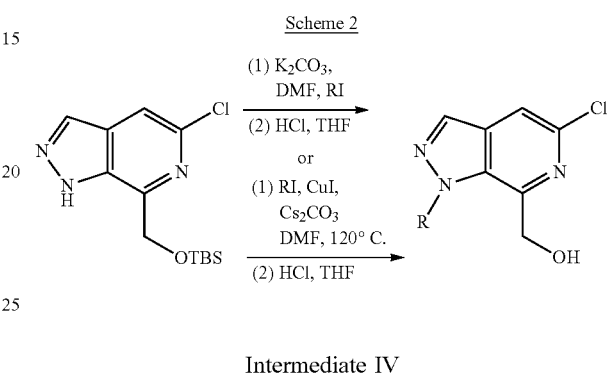

Intermediate IV

[5-chloro-1-methyl-1H-pyrazolo[3,4-c]pyridin-7-yl]methanol

To a solution of 7-[[(tert-butyldimethylsilyl)oxy]methyl]-5-chloro-1H-pyrazolo[3,4-c]pyridine (1 g, 3.36 mmol) in DMF (10 mL) were added iodomethane (477 mg, 3.36 mmol) and potassium carbonate (700 mg, 5.07 mmol). The resulting mixture was stirred for 10 h at 20° C. and then filtered. The filtrate was concentrated under reduced pressure. The residue was diluted with DCM, washed with saturated NaHCO$_3$, dried (Na$_2$SO$_4$), and filtered. After removal of the solvent by evaporation, the residue was purified by chromatography on SiO$_2$, eluted with petroleum ether/EtOAc (2:1) to give the desired isomer, 7-[[(tert-butyldimethylsilyl)oxy]methyl]-5-chloro-1-methyl-1H-pyrazolo[3,4-c]pyridine, which was dissolved in THF/HCl (4 M)=1:2 (24 mL). The mixture was stirred for 30 min and concentrated. The residue was diluted with saturated NaHCO$_3$, extracted with DCM, washed with brine, dried (Na$_2$SO$_4$) and filtered. The filtrate was concentrated under reduced pressure to give [5-chloro-1-methyl-1H-pyrazolo[3,4-c]pyridin-7-yl]methanol (200 mg). MS (EI) calc'd for C$_8$H$_9$ClN$_3$O [M+H]$^+$ 198, found 198.

| Intermediate # | Structure | IUPAC Name | Exact Mass [M + H]+ |
|---|---|---|---|
| V | 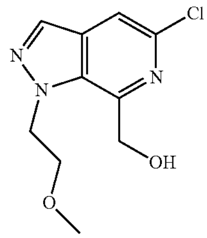 [SMILES: COCCn1ncc2cc(Cl)nc(CO)c21] | (5-chloro-1-(2-methoxyethyl)-1H-pyrazolo[3,4-c]pyridin-7-yl)methanol | Calc'd 242, found 242 |
| VI | 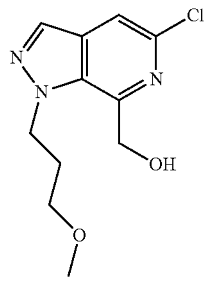 [SMILES: COCCCn1ncc2cc(Cl)nc(CO)c21] | (5-chloro-1-(3-methoxypropyl)-1H-pyrazolo[3,4-c]pyridin-7-yl)methanol | Calc'd 256, found 256 |

Intermediate VII

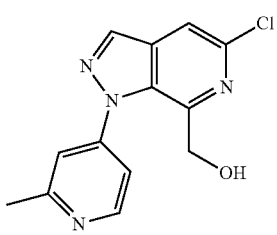 [SMILES: Cc1cc(-n2ncc3cc(Cl)nc(CO)c32)ccn1]

(5-Chloro-1-(2-methylpyridin-4-yl)-1H-pyrazolo[3,4-c]pyridin-7-yl)methanol

Step 1: 7-(((tert-Butyldimethylsilyl)oxy)methyl)-5-chloro-1-(2-methylpyridin-4-yl)-1H-pyrazolo[3,4-c]pyridine To a solution of 7-(((tert-butyldimethylsilyl)oxy)methyl)-5-chloro-1H-pyrazolo[3,4-c]pyridine (1 g, 3.36 mmol) in DMF (20 mL) were added 4-iodo-2-methylpyridine (0.88 g, 4.03 mmol), CuI (0.19 g, 1.01 mmol), $Cs_2CO_3$ (2.19 g, 6.71 mmol) and 2-acetylcyclohexanone (0.28 g, 2.014 mmol). The mixture was purged by bubbling nitrogen for 3 min and then stirred for 1.5 h at 120° C. under microwave irradiation. The resulting mixture was concentrated under vacuum. The residue was purified by chromatography on $SiO_2$, eluted with DCM/MeOH (20:1) to give 7-(((tert-butyldimethylsilyl)oxy)methyl)-5-chloro-1-(2-methylpyridin-4-yl)-1H-pyrazolo[3,4-c]pyridine. MS (EI) calc'd for $C_{19}H_{26}ClN_4OSi$ [M+H]$^+$ 389, found 389.

Step 2: (5-Chloro-1-(2-methylpyridin-4-yl)-1H-pyrazolo[3,4-c]pyridin-7-yl)methanol 7-(((tert-Butyldimethylsilyl)oxy)methyl)-5-chloro-1-(2-methylpyridin-4-yl)-1H-pyrazolo[3,4-c]pyridine (260 mg, 0.67 mmol) was dissolved in THF/HCl (4 M)=1:2 (24 mL). The mixture was stirred for 30 min and concentrated under reduced pressure. The residue was diluted with saturated $NaHCO_3$, extracted with DCM, washed with brine, dried ($Na_2SO_4$) and filtered. The filtrate was concentrated under reduced pressure. The residue was purified by chromatography on $SiO_2$, eluted with DCM/MeOH (10:1) to give (5-chloro-1-(2-methylpyridin-4-yl)-1H-pyrazolo[3,4-c]pyridin-7-yl)methanol. MS (EI) calc'd for $C_{13}H_{12}ClN_4O$ [M+H]$^+$ 275, found 275.

Scheme 3

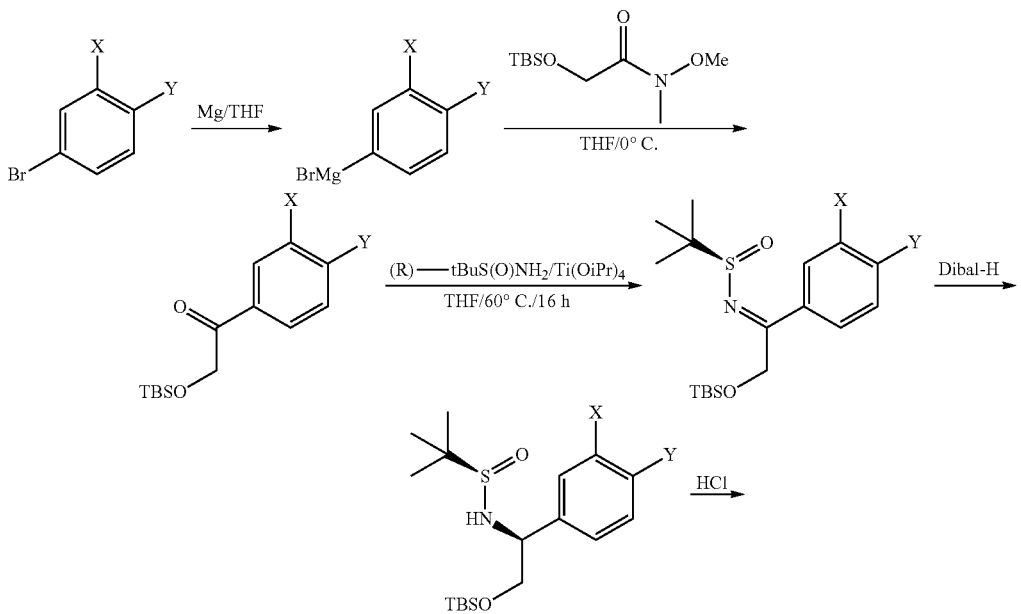

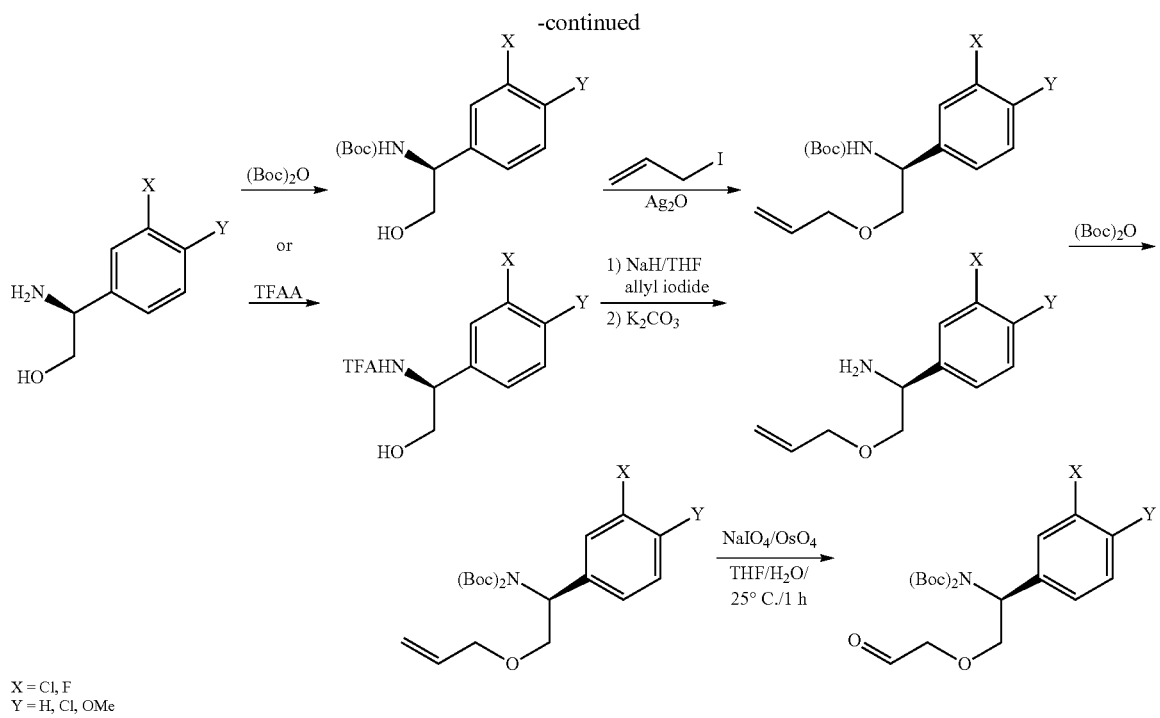

X = Cl, F
Y = H, Cl, OMe

Intermediate VIII

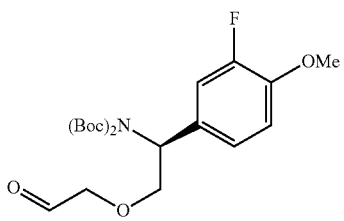

(S)-tert-Butyl N-[(tert-butoxy)carbonyl]-N-[(1S)-1-(3-fluoro-4-methoxyphenyl)-2-(2-oxoethoxy)ethyl]carbamate Step 1. 2-(tert-Butyldimethylsilyloxy)-1-(3-fluoro-4-methoxyphenyl)ethanone To a mixture of magnesium (0.89 g, 36.6 mmol) and 1,2-dibromoethane (0.23 g, 1.22 mmol) in THF (5 mL) was added a solution of 4-bromo-2-fluoro-1-methoxybenzene (5.00 g, 24.39 mmol) in THF (50 mL) at 20° C. dropwise during 30 min. After stirring for 1 h at 20° C., a solution of 2-((tert-butyldimethylsilyl)oxy)-N-methoxy-N-methylacetamide (5.69 g, 24.39 mmol) in THF (50 mL) was added. The reaction progress was monitored by LCMS. The reaction mixture was quenched with water (100 mL) and extracted with ethyl acetate (3×100 mL). The combined organic layers were washed with brine (100 mL), dried over anhydrous sodium sulfate and filtered. The filtrate was concentrated under reduced pressure, the residue was purified by chromatography on $SiO_2$, eluted with petroleum ether/EtOAc (10:1) to afford 2-((tert-butyldimethylsilyl)oxy)-1-(3-fluoro-4-methoxyphenyl)ethanone. MS (EI) calc'd for $C_{15}H_{24}FO_3Si$ $[M+H]^+$ 299, found 299.

Step 2. (R,E)-N-(2-(tert-butyldimethylsilyloxy)-1-(3-fluoro-4-methoxyphenyl)ethylidene)-2-methylpropane-2-sulfinamide To a mixture of 2-((tert-butyldimethylsilyl)oxy)-1-(3-fluoro-4-methoxyphenyl)ethanone (45.0 g, 151 mmol) and (R)-2-methylpropane-2-sulfinamide (21.9 g, 181 mmol) in THF (500 mL) was added titanium (IV) isopropoxide (110 mL, 377 mmol). The resulting mixture was stirred for 12 h at 70° C. The reaction progress was monitored by LCMS. The reaction mixture was quenched with brine (50 mL) and the solid was filtered out. The filtrate was concentrated under reduced pressure to afford (R,E)-N-(2-((tert-butyldimethylsilyl)oxy)-1-(3-fluoro-4-methoxyphenyl)ethylidene)-2-methylpropane-2-sulfinamide, which was used directly for next step without further purification. MS (EI) calc'd for $C_{19}H_{33}FNO_3SSi$ $[M+H]^+$ 402, found 402.

Step 3. (R)-N-(2-(tert-butyldimethylsilyloxy)-1-(3-fluoro-4-methoxyphenyl)ethyl)-2-methylpropane-2-sulfinamide To a mixture of (R,E)-N-(2-((tert-butyldimethylsilyl)oxy)-1-(3-fluoro-4-methoxyphenyl)ethylidene)-2-methylpropane-2-sulfinamide (30 g, 74.7 mmol) in THF (200 mL) was added DIBAL-H (106 g, 187 mmol) dropwise at −78° C. under $N_2$. The resulting mixture was stirred for 1 h at −78° C. The reaction progress was monitored by LCMS. The reaction mixture was quenched with brine (500 mL) and the solid was filtered out. The filtrate was concentrated under reduced pressure to afford (R)-N-((S)-2-((tert-butyldimethylsilyl)oxy)-1-(3-fluoro-4-methoxyphenyl)ethyl)-2-methylpropane-2-sulfinamide. MS (EI) calc'd for $C_{19}H_{35}FNO_3SSi$ $[M+H]^+$ 404, found 404.

Step 4. (S)-2-amino-2-(3-fluoro-4-methoxyphenyl)ethanol

To a mixture of (R)—N—((S)-2-((tert-butyldimethylsilyl)oxy)-1-(3-fluoro-4-methoxyphenyl)ethyl)-2-methylpropane-2-sulfinamide (40 g, 99 mmol) was added 5 N HCl in MeOH (1000 mL). The resulting mixture was stirred for 12 h at 25° C. The reaction progress was monitored by LCMS. The reaction mixture was washed with ethyl acetate (3×500 mL) and the organic layer was discarded. The aqueous layer was adjust to PH=10 by $K_2CO_3$ powder and extracted with dichloromethane/methanol (10:1) (5×500 mL). The organic layer was concentrated under reduced pressure to afford (S)-2-amino-2-(3-fluoro-4-methoxyphenyl)ethanol, which was used directly for next step without further purification. MS (EI) calc'd for $C_9H_{13}FNO_2$ $[M+H]^+$ 186, found 186.

Step 5. (S)-tert-Butyl 1-(3-fluoro-4-methoxyphenyl)-2-hydroxyethylcarbamate

To a mixture of (S)-2-amino-2-(3-fluoro-4-methoxyphenyl)ethanol (3.0 g, 16.2 mmol) in THF (100 mL), was added di-tert-butyl dicarbonate (5.3 g, 24.3 mmol) at 25° C. After stirring for 1 h at 25° C., the reaction mixture was quenched with water (100 mL) and extracted with ethyl acetate (3×100 mL). The combined organic layers were washed with brine (100 mL), dried over anhydrous sodium sulfate and filtered. The filtrate was concentrated under reduced pressure, the residue was purified by chromatography on $SiO_2$, eluted with petroleum ether/EtOAc (1:1) to give (S)-tert-butyl (1-(3-fluoro-4-methoxyphenyl)-2-hydroxyethyl)carbamate. MS (EI) calc'd for $C_{14}H_{21}FNO_4$ $[M+H]^+$ 286, found 286.

Step 6. (S)-tert-Butyl 2-(allyloxy)-1-(3-fluoro-4-methoxyphenyl)ethylcarbamate To a mixture of (S)-tert-butyl (1-(3-fluoro-4-methoxyphenyl)-2-hydroxyethyl)carbamate (1.00 g, 3.50 mmol) in toluene (20 mL) were added 3-iodoprop-1-ene (0.88 g, 5.26 mmol), KI (0.87 g, 5.26 mmol) and silver oxide (2.44 g, 10.51 mmol). The resulting mixture was stirred for 16 h at 110° C. and cooled down to ambient temperature. The reaction mixture was quenched with water (10 mL). The solid was filtered out and the filtrate was extracted with ethyl acetate (3×50 mL). The combined organic layers were washed with brine (50 mL), dried over anhydrous sodium sulfate and filtered. The filtrate was concentrated under reduced pressure, the residue was purified by chromatography on $SiO_2$, eluted with petroleum ether/EtOAc (3:1) to give (S)-tert-butyl (2-(allyloxy)-1-(3-fluoro-4-methoxyphenyl)ethyl)carbamate. MS (EI) calc'd for $C_{17}H_{25}FNO_4$ $[M+H]^+$ 326, found 326.

Step 7. (S)-tert-Butyl N-[(tert-butoxy)carbonyl]-N-[(1S)-1-(3-fluoro-4-methoxyphenyl)-2-(prop-2-en-1-yloxy)ethyl]carbamate To a mixture of (S)-tert-butyl (2-(allyloxy)-1-(3-fluoro-4-methoxyphenyl)ethyl)carbamate (0.90 g, 2.77 mmol) in THF (20 mL) were added di-tert-butyl dicarbonate (1.21 g, 5.53 mmol) and DMAP (676 mg, 5.53 mmol). The resulting mixture was stirred for 3 h at 70° C. and cooled down to ambient temperature. The reaction mixture was quenched with water (20 mL) and extracted with ethyl acetate (3×100 mL). The combined organic layers were washed with brine (50 mL), dried over anhydrous sodium sulfate and filtered. The filtrate was concentrated under reduced pressure, the residue was purified by chromatography on $SiO_2$, eluted with petroleum ether/EtOAc (3:1) to give tert-butyl N-[(tert-butoxy)carbonyl]-N-[(1S)-1-(3-fluoro-4-methoxyphenyl)-2-(prop-2-en-1-yloxy)ethyl]carbamate. MS m/z $[2M+Na]^+$: 873.

Step 8. (S)-tert-Butyl N-[(tert-butoxy)carbonyl]-N-[(1S)-1-(3-fluoro-4-methoxyphenyl)-2-(2-oxoethoxy)ethyl]carbamate To a mixture of tert-butyl N-[(tert-butoxy)carbonyl]-N-[(1S)-1-(3-fluoro-4-methoxyphenyl)-2-(prop-2-en-1-yloxy)ethyl]carbamate (900 mg, 2.115 mmol) in THF (20 mL) and Water (2 mL) were added sodium periodate (679 mg, 3.17 mmol) and osmium tetroxide (0.066 mL, 0.212 mmol). After stirring for 3 h at 25° C., the reaction mixture was quenched with water (20 mL) and extracted with ethyl acetate (3×100 mL). The combined organic layers were washed with brine (50 mL), dried over anhydrous sodium sulfate and filtered. The filtrate was concentrated under reduced pressure, the residue was purified by chromatography on $SiO_2$, eluted with petroleum ether/EtOAc (2:1) to give tert-butyl N-[(tert-butoxy)carbonyl]-N-[(1S)-1-(3-fluoro-4-methoxyphenyl)-2-(2-oxoethoxy)ethyl]carbamate. MS (EI) calc'd for $C_{21}H_3FNO_7$ $[M+H]^+$ 428, found 428.

Intermediate IX

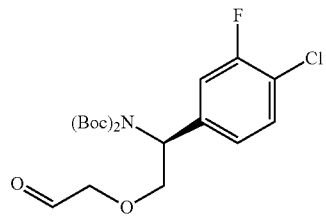

(S)-tert-Butyl N-[(tert-butoxy)carbonyl] 1-(4-chloro-3-fluorophenyl)-2-(2-oxoethoxy)ethylcarbamate Synthesis of intermediate IX is similar to Intermediate VIII besides the following procedures from intermediate (S)-2-Amino-2-(4-chloro-3-fluorophenyl)ethanol.

Step 1. (S)-N-(1-(4-Chloro-3-fluorophenyl)-2-hydroxyethyl)-2,2,2-trifluoroacetamide TEA (4.85 mL, 34.8 mmol) was added dropwise to a stirred, cooled (0° C.) mixture of 2,2,2-trifluoroacetic anhydride (3.66 g, 17.40 mmol) and (S)-2-Amino-2-(4-chloro-3-fluorophenyl)ethanol (2.19 g, 11.6 mmol) in dichloromethane (50 mL). After stirring at 25° C. for 2 h, the reaction mixture was diluted with dichloromethane (50 mL), washed with saturated aqueous ammonium chloride (2×30 mL), dried ($Na_2SO_4$) and filtered. The filtrate was evaporated under reduced pressure. The residue was purified by chromatography on $SiO_2$, eluted with petroleum ether/EtOAc (3:1) to give (S)-N-(1-(4-chloro-3-fluorophenyl)-2-hydroxyethyl)-2,2,2-trifluoroacetamide. MS (EI) calc'd for $C_{10}H_9ClF_4NO_2$ $[M+H]^+$ 286, found 286.

Step 2. (S)-N-(2-(Allyloxy)-1-(4-chloro-3-fluorophenyl)ethyl)-2,2,2-trifluoroacetamide To a suspension of sodium hydride (0.62 g, 15.4 mmol) (60% in mineral oil) in THF (50 mL) was added a solution of (S)-N-(1-(4-Chloro-3-fluorophenyl)-2-hydroxyethyl)-2,2,2-trifluoroacetamide (3.00 g, 10.5 mmol) in THF (10 mL) at 0° C. After stirring for 30 min at 0° C., 3-bromoprop-1-ene (1.56 g, 12.9 mmol) was added. The resulting mixture was stirred at 25° C. for 2 h, quenched with water (50 mL) and extracted with ethyl acetate (3×100 mL). The combined organic phases were washed with brine (2×100 mL), dried ($Na_2SO_4$), and filtered. The filtrate was evaporated under reduced pressure. The residue was purified by chromatography on $SiO_2$, eluted with petroleum ether/EtOAc (10:1) to give (S)-N-(2-(allyloxy)-1-(4-chloro-3-fluorophenyl)ethyl)-2,2,2-trifluoroacetamide. MS (EI) calc'd for $C_{13}H_{13}ClF_4NO_2$ [M+H]$^+$ 326, found 326.

Step 3. (S)-2-(Allyloxy)-1-(4-chloro-3-fluorophenyl)ethanamine

To a solution of (S)-N-(2-(allyloxy)-1-(4-chloro-3-fluorophenyl)ethyl)-2,2,2-trifluoroacetamide (1.50 g, 4.61 mmol) in methanol (20 mL) were added potassium carbonate (1.27 g, 9.21 mmol) and water (2 mL). The resulting mixture was stirred at 65° C. for 3 h. After cooling down to ambient temperature, the reaction mixture was quenched with water (50 mL) and extracted with ethyl acetate (3×50 mL). The combined organic phases were washed with brine (2×50 mL), dried ($Na_2SO_4$), and filtered. The filtrate was evaporated under reduced pressure to give (S)-2-(allyloxy)-1-(4-chloro-3-fluorophenyl)ethanamine, which was used directly for next step without further purification. MS (EI) calc'd for $C_{11}H_{14}ClFNO$ [M+H]$^+$ 230, found 230.

Step 4. (S)-tert-Butyl (2-(allyloxy)-1-(4-chloro-3-fluorophenyl)ethyl)carbamate

To a solution of (S)-2-(allyloxy)-1-(4-chloro-3-fluorophenyl)ethanamine (1.05 g, 4.57 mmol) in dichloromethane (50 mL) were added TEA (1.27 mL, 9.14 mmol) and di-tert-butyl dicarbonate (1.20 g, 5.49 mmol). After stirring at 25° C. for 15 h, the reaction mixture was quenched with water (50 mL) and extracted with dichloromethane (3×50 mL). The combined organic phases were washed with brine (2×50 mL), dried ($Na_2SO_4$), and filtered. The filtrate was evaporated under reduced pressure to give a crude product of (S)-tert-butyl (2-(allyloxy)-1-(4-chloro-3-fluorophenyl)ethyl)carbamate, which was used directly for the next step without further purification. MS (EI) calc'd for $C_{16}H_{22}ClFNO_3$ [M+H]$^+$ 330, found 330.

Intermediate X

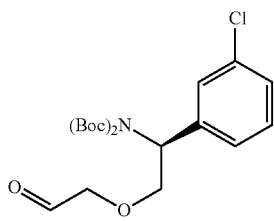

tert-Butyl N-[(tert-butoxy)carbonyl]-N-(1S)-1-(3-chlorophenyl)-2-(2-oxoethoxy)ethyl carbamate Step 1: (S)-tert-butyl (1-(3-chlorophenyl)-2-hydroxyethyl)carbamate A mixture of (S)-2-amino-2-(3-chlorophenyl)ethanol (4.70 g, 27.4 mmol), Boc$_2$O (9.54 mL, 41.1 mmol) and Et$_3$N (7.63 mL, 54.8 mmol) in DCM (100 mL) was stirred at 25° C. for 24 h. Water (200 mL) was added and the mixture was extracted with dichloromethane (3×50 mL). The combined organic phases were washed with brine (3×50 mL), dried ($Na_2SO_4$) and filtered. After the solvent was evaporated under reduced pressure, the residue was purified by chromatography on $SiO_2$, eluted with dichloromethane/methanol (100:1-20:1) to give (S)-tert-butyl (1-(3-chlorophenyl)-2-hydroxyethyl)carbamate. MS (EI) calc'd for $C_{13}H_{19}ClNO_3$ [M+H]$^+$ 272, found 272; $^1$H-NMR (300 MHz, DMSO-d$_6$): δ ppm 7.44-7.26 (m, 5 H), 4.83 (t, J=5.7 Hz, 1 H), 4.52 (t, J=6.0 Hz, 1 H), 3.54-3.46 (m, 2 H), 1.37 (s, 9 H).

Step 2. (S)-tert-Butyl (2-(allyloxy)-1-(3-chlorophenyl)ethyl)carbamate

A mixture of (S)-tert-butyl (1-(3-chlorophenyl)-2-hydroxyethyl)carbamate (2.00, 7.36 mmol), 3-iodoprop-1-ene (1.85 g, 11.04 mmol), KI (1.22 g, 7.36 mmol) and silver oxide (8.53 g, 36.8 mmol) in toluene (20 mL) was stirred at 100° C. for 12 h. The mixture was filtered, washing with ethyl acacate (100 mL), and the filtrate was washed with brine (3×20 mL), dried (Na$_2$SO$_4$) and filtered. The filtrate was concentrated under reduced pressure. The residue was purified by chromatography on $SiO_2$, eluted with petroleum ether/EtOAc (100:1-10:1) to give (S)-tert-butyl (2-(allyloxy)-1-(3-chlorophenyl)ethyl)carbamate. MS (EI) calc'd for $C_{16}H_{23}ClNO_3$ [M+H]$^+$ 312, found 312; $^1$H-NMR (300 MHz, DMSO-d$_6$): δ ppm 7.47-7.27 (m, 5 H), 5.91-5.76 (m, 1 H), 5.28-5.10 (m, 2 H), 4.83-4.72 (m, 1 H), 3.95 (d, J=5.1, 2 H), 3.53-3.44 (m, 2 H), 1.37 (s, 9 H).

Step 3. tert-Butyl N-[(tert-butoxy)carbonyl]-N-(1S)-1-(3-chlorophenyl)-2-(prop-2-en-1-yloxy)ethyl carbamate A mixture of (S)-tert-butyl (2-(allyloxy)-1-(3-chlorophenyl)ethyl)carbamate (0.90 g, 2.89 mmol), di-tert-butyl dicarbonate (0.95 g, 4.33 mmol) and DMAP (0.35 g, 2.89 mmol) in THF (20 mL) was stirred at 70° C. for 4 h. The mixture was cooled to 20° C., diluted with ethyl acetate (50 mL), washed with brine (3×20 mL), dried (Na$_2$SO$_4$) and filtered. The filtrate was concentrated under reduced pressure. The residue was purified by chromatography on $SiO_2$, eluted with petroleum ether/EtOAc (100:1-20:1) to give tert-butyl N-[(tert-butoxy)carbonyl]-N-(1S)-1-(3-chlorophenyl)-2-(prop-2-en-1-yloxy)ethyl carbamate. MS (EI) calc'd for $C_{21}H_{31}ClNO_5$ [M+H]$^+$ 412, found 412; $^1$H-NMR (300 MHz, DMSO-d$_6$): δ ppm 7.43-7.28 (m, 4 H), 5.93-5.82 (m, 1 H), 5.40 (t, J=7.2 Hz, 1 H), 5.30-5.14 (m, 2 H), 4.00-3.89 (m, 4 H), 1.37 (s, 18 H).

Step 4. tert-Butyl N-[(tert-butoxy)carbonyl]-N-(1S)-1-(3-chlorophenyl)-2-(2-oxoethoxy)ethyl carbamate A mixture of tert-butyl N-[(tert-butoxy)carbonyl]-(1S)-1-(3-chlorophenyl)-2-(prop-2-en-1-yloxy)ethyl carbamate (300 mg, 0.728 mmol), osmium(VIII) oxide (18.52 mg, 0.073 mmol) and sodium periodate (779 mg, 3.64 mmol) in THF (10 mL) and water (1 mL) was stirred at 25° C. for 3 h. The reaction mixture was diluted with ethyl acetate (50 mL), washed with brine (3×20 mL), dried (Na$_2$ SO$_4$), and filtered. The filtrate was concentrated under reduced pressure. The residue was purified by chromatography on $SiO_2$, eluted with petroleum ether/EtOAc (100:1-25:1) to give tert-butyl N-[(tert-butoxy)carbonyl]-N-(1S)-1-(3-chlorophenyl)-2-(2-oxoethoxy)ethyl carbamate. MS (EI) calc'd for $C_{20}H_{29}ClNO_6$ [M+H]$^+$ 414, found 414; $^1$H-NMR (300 MHz, DMSO-d$_6$): δ ppm 9.58 (s, 1 H), 7.37-7.29 (m, 4 H), 5.44 (m, 1 H), 4.34-4.27 (m, 2 H), 4.20-3.99 (m, 2 H), 1.36 (s, 18 H).

Synthetic Method 1

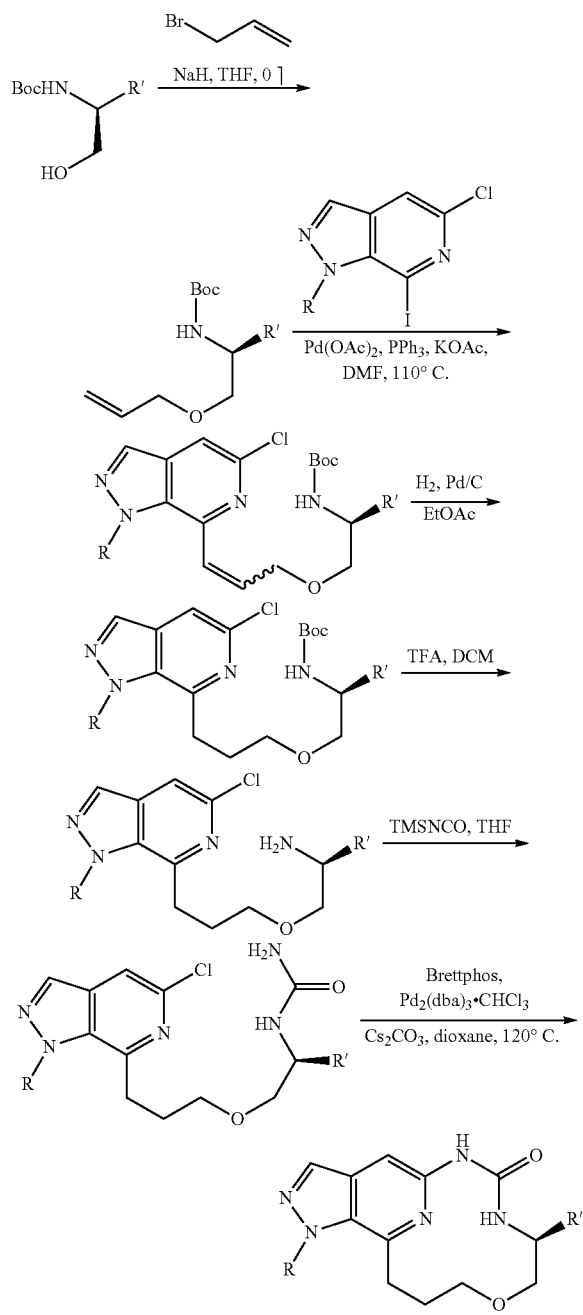

The experimental conditions for example 1 were used as standard protocol through out with appropriate reagent.

An embodiment of the invention is all of the species exemplified in Examples 1-58. The ERK2 IC$_{50}$ in nanomolar (nM) for the compounds of the invention, measured according to the assay "Active human ERK2 (hERK2) Activity Assay" described below, is shown in the Example next to the structure or compound name.

Example 1

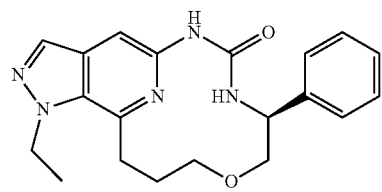 [SMILES: CCn1ncc2cc3nc(c21)CCCOC[C@H](c1ccccc1)NC(=O)N3]

(9S)-1-Ethyl-9-phenyl-1,6,9,10,13,14-hexahydro-12H-5,15-(azeno)pyrazolo[4,3-i][1,4,6]oxadiazacyclotetradecin-7(8H)-one Step 1: (S)-tert-Butyl (2-(allyloxy)-1-phenylethyl)carbamate To a cooled 0° C. mixture of sodium hydride (0.61 g, 15.17 mmol)(60% in mineral oil) in THF (100 mL) was added (S)-tert-butyl (2-hydroxy-1-phenylethyl)carbamate (3.00 g, 12.64 mmol). After stirred for 30 min at 0° C., 3-bromoprop-1-ene (1.53 g, 12.64 mmol) was added. The mixture was stirred at 25° C. for 2 h, quenched with water and concentrated under reduced pressure. The residue was diluted with EtOAc, washed with water, brine, dried (Na$_2$SO$_4$), filtered and concentrated. The crude product was purified by chromatography on SiO$_2$, eluted with petroleum ether/EtOAc (10:1) to give (S)-tert-butyl (2-(allyloxy)-1-phenylethyl)carbamate. MS (EI) calc'd for $C_{16}H_{24}NO_3$ [M+H]$^+$ 278, found 278.

Step 2: (S)-tert-Butyl 2-(3-(5-chloro-1-ethyl-1H-pyrazolo[3,4-c]pyridin-7-yl)allyloxy)-1-phenylethylcarbamate; standard Heck coupling A mixture of (S)-tert-butyl (2-(allyloxy)-1-phenylethyl) carbamate (631 mg, 2.28 mmol), 5-chloro-1-ethyl-7-iodo-1H-pyrazolo[3,4-c]pyridine (700 mg, 2.28 mmol), Pd(OAc)$_2$ (51.1 mg, 0.23 mmol), potassium acetate (447 mg, 4.55 mmol) and triphenylphosphine (59.7 mg, 0.23 mmol) in DMF (15 mL) was degassed under vacuum, purged by bubbling nitrogen for 3 min and then stirred for 3 h at 110° C. The resulting mixture was concentrated under vacuum. The residue was diluted with water, extracted with EtOAc, washed with brine, dried (Na$_2$SO$_4$), filtered and concentrated. The residue was purified by chromatography on SiO$_2$, eluted with petroleum ether/EtOAc (5:1) to give (S)-tert-butyl 2-(3-(5-chloro-1-ethyl-1H-pyrazolo[3,4-c]pyridin-7-yl)allyloxy)-1-phenylethylcarbamate. MS (EI) calc'd for $C_{24}H_{30}ClN_4O_3$ [M+H]$^+$ 457, found 457.

Step 3: (S)-tert-Butyl 2-(3-(5-chloro-1-ethyl-1H-pyrazolo[3,4-c]pyridin-7-yl)propoxy)-1-phenylethyl-carbamate A suspension of (S)-tert-butyl 2-(3-(5-chloro-1-ethyl-1H-pyrazolo[3,4-c]pyridin-7-yl)allyloxy)-1-phenylethylcarbamate (340 mg, 0.74 mmol) and 10% Pd/C (50 mg, 0.047 mmol) in EtOAc (30 mL) was purged in 2-4 atm. of hydrogen and stirred for 10 h at 25° C. under an atmosphere of hydrogen (2~4 atm.). The mixture was filtered and concentrated under reduced pressure. The residue was used directly for the next step without further purification. MS (EI) calc'd for $C_{24}H_{32}ClN_4O_3$ [M+H]$^+$ 459, found 459.

Step 4: (S)-2-(3-(5-Chloro-1-ethyl-1H-pyrazolo[3,4-c]pyridin-7-yl)propoxy)-1-phenylethanamine; standard TFA deprotection (S)-tert-butyl 2-(3-(5-chloro-1-ethyl-1H-pyrazolo[3,4-c]pyridin-7-yl)propoxy)-1-phenylethylcarbamate (340 mg, 0.74 mmol) was dissolved with trifluoroacetic acid (5 mL)/DCM (5 mL) and stirred for 2 h at 25° C. Then the resulting solution was concentrated under reduced pressure. The residue was diluted with saturated NaHCO$_3$, extracted with EtOAc, washed with brine, dried (Na$_2$SO$_4$), filtered and concentrated. The residue was used directly in the next step without further purification. MS (EI) calc'd for C$_{19}$H$_{24}$ClN$_4$O [M+H]$^+$ 359, found 359.

Step 5: (S)-1-(2-(3-(5-Chloro-1-ethyl-1H-pyrazolo[3,4-c]pyridin-7-yl)propoxy)-1-phenylethyl)urea; standard urea formation Trimethylsilylisocyanate (417 mg, 3.62 mmol) was added to a stirred mixture of (S)-2-(3-(5-chloro-1-ethyl-1H-pyrazolo[3,4-c]pyridin-7-yl)propoxy)-1-phenylethanamine (260 mg, 0.73 mmol) in THF (15 mL) and the mixture was stirred at 60° C. for 12 h. The resulting mixture was concentrated under reduced pressure. The residue was purified by Prep-TLC (DCM/MeOH=20:1) to give (S)-1-(2-(3-(5-chloro-1-ethyl-1H-pyrazolo[3,4-c]pyridin-7-yl)propoxy)-1-phenylethyl)urea. MS (EI) calc'd for C$_{20}$H$_{25}$ClN$_5$O$_2$ [M+H]$^+$ 402, found 402.

Step 6: (9S)-1-Ethyl-9-phenyl-1,6,9,10,13,14-hexahydro-12H-5,15-(azeno)pyrazolo[4,3-i][1,4,6]oxadiazacyclotetradecin-7(8H)-one; standard Buchwald coupling To a mixture of (S)-1-(2-(3-(5-chloro-1-ethyl-1H-pyrazolo[3,4-c]pyridin-7-yl)propoxy)-1-phenylethyl)urea (120 mg, 0.30 mmol) in dioxane (5 mL) was added Pd$_2$(dba)$_3$·CHCl$_3$ (16.5 mg, 0.03 mmol), Brettphos (12.6 mg, 0.03 mmol), Cs$_2$CO$_3$ (207 mg, 0.60 mmol). The resulting mixture was purged by bubbling nitrogen for 3 min, heated to 120° C. and stirred for 5 h. The mixture was concentrated under reduced pressure. The residue was diluted with water, extracted with EtOAc, washed with brine, dried (Na$_2$SO$_4$), filtered and concentrated under vacuum. The residue was purified by Prep-TLC (DCM/MeOH=20:1) to give (9S)-1-ethyl-9-phenyl-1,6,9,10,13,14-hexahydro-12H-5,15-(azeno)pyrazolo[4,3-i][1,4,6]oxadiazacyclotetradecin-7(8H)-one. MS (EI) calc'd for C$_{20}$H$_{24}$N$_5$O$_2$ [M+H]$^+$ 366, found 366; $^1$H NMR (300 MHz, DMSO-d$_6$) δ 11.48 (d, J=7.8 Hz, 1 H), 9.21 (s, 1 H), 8.10 (s, 1 H), 7.41-7.31 (m, 4 H), 7.26-7.24 (m, 1 H), 7.04 (s, 1H), 4.82-4.79 (m, 1 H), 4.58 (q, J=7.2 Hz, 2 H), 3.95-3.90 (m, 1 H), 3.81-3.77 (m, 1 H), 3.63-3.58 (m, 1 H), 3.48-3.45 (m, 1 H), 3.36-3.29 (m, 2 H), 2.28-2.26 (m, 1 H), 2.08-2.03 (m, 1 H), 1.41 (t, J=7.2 Hz, 3 H).

Example 2

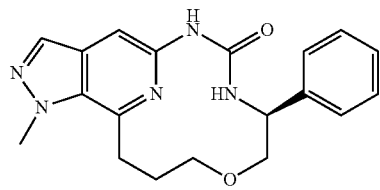 [SMILES: Cn1ncc2cc3nc(c21)CCCOC[C@H](c1ccccc1)NC(=O)N3]

(9S)-1-Methyl-9-phenyl-1,6,9,10,13,14-hexahydro-12H-5,15-(azeno)pyrazolo[4,3-i][1,4,6]oxadiazacyclotetradecin-7(8H)-one This compound was synthesized by the same method as described in example 1 except intermediate II was used in step 2: MS (EI) calc'd for C$_{19}$H$_{22}$N$_5$O$_2$[M+H]$^+$ 352, found 352; $^1$H NMR (300 MHz, DMSO-d$_6$) δ 11.49 (d, J=7.8 Hz, 1 H), 9.20 (s, 1 H), 8.04 (s, 1 H), 7.42-7.31 (m, 4 H), 7.26-7.23 (m, 1 H), 7.03 (s, 1 H), 4.81-4.78 (m, 1 H), 4.26 (s, 3 H), 3.95-3.90 (m, 1 H), 3.81-3.74 (m, 1 H), 3.61-3.56 (m, 1 H), 3.46-3.32 (m, 3 H), 2.27-2.23 (m, 1 H), 2.07-2.02 (m, 1 H).

Synthetic Method 2

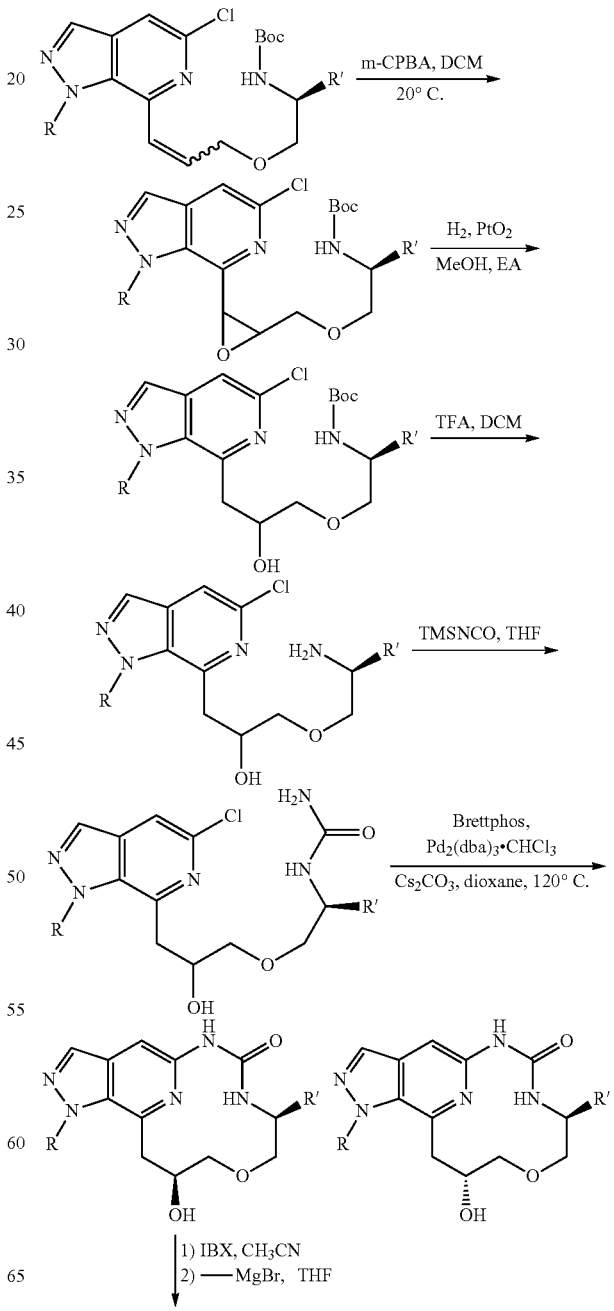

-continued

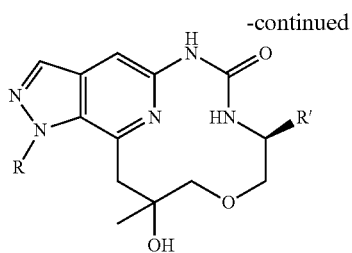

Example 3

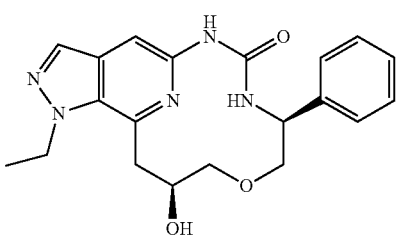 [SMILES: CCn1ncc2cc3nc(c21)C[C@H](O)COC[C@H](c1ccccc1)NC(=O)N3]

(9S,13S)-1-Ethyl-13-hydroxy-9-phenyl-1,6,9,10,13,14-hexahydro-12H-5,15-(azeno)pyrazolo[4,3-i][1,4,6]oxadiazacyclotetradecin-7(8H)-one Example 4

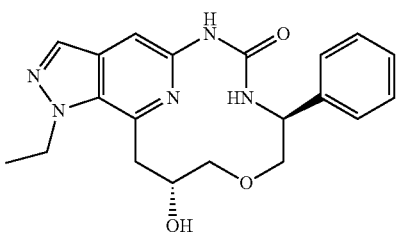 [SMILES: CCn1ncc2cc3nc(c21)C[C@@H](O)COC[C@H](c1ccccc1)NC(=O)N3]

(9S,13R)-1-Ethyl-13-hydroxy-9-phenyl-1,6,9,10,13,14-hexahydro-12H-5,15-(azeno)pyrazolo[4,3-i][1,4,6]oxadiazacyclotetradecin-7(8H)-one Step 1: tert-Butyl (S)-2-((3-(5-chloro-1-ethyl-1H-pyrazolo[3,4-c]pyridin-7-yl)oxiran-2-yl)methoxy)-1-phenylethylcarbamate m-CPBA (2.0 g, 11.59 mmol) was added to a stirred mixture of (S)-tert-butyl (2-((3-(5-chloro-1-ethyl-1H-pyrazolo [3,4-c]pyridin-7-yl)allyl)oxy)-1-phenylethyl)carbamate (2.2 g, 3.51 mmol) in DCM (30 mL). After stirring for 10 h at 25° C., the resulting mixture was quenched by 10% $Na_2SO_3$ and extracted with EtOAc, washed with saturated $NaHCO_3$, brine, dried ($Na_2SO_4$), filtered and concentrated under reduce pressure. The residue was purified by chromatography on $SiO_2$, eluted with petroleum ether/EtOAc (2:1) to give tert-butyl (S)-2-((3-(5-chloro-1-ethyl-1H-pyrazolo[3,4-c]pyridin-7-yl)oxiran-2-yl)methoxy)-1-phenylethylcarbamate. MS (EI) calc'd for $C_{24}H_{30}ClN_4O_4$ [M+H]$^+$ 473, found 473.

Step 2: tert-Butyl (S)-2-(3-(5-chloro-1-ethyl-1H-pyrazolo [3,4-c]pyridin-7-yl)-2-hydroxypropoxy)-1-phenylethylcarbamate To a solution of tert-butyl ((1S)-2-((3-(5-chloro-1-ethyl-1H-pyrazolo[3,4-c]pyridin-7-yl)oxiran-2-yl)methoxy)-1-phenylethyl)carbamate (800 mg, 1.69 mmol) in MeOH/EtOAc (1/1, 30 mL) was added platinum(IV) oxide (300 mg, 1.32 mmol). The mixture was purged in 2~4 atm. of hydrogen and stirred for 5 h at 20° C. under an atmosphere of hydrogen (2~4 atm.). The reaction mixture was filtered and concentrated under reduced pressure. The residue was used directly for the next step without further purification. MS (EI) calc'd for $C_{24}H_{32}ClN_4O_4$ [M+H]$^+$ 475, found 475.

Step 3: 1-((S)-2-Amino-2-phenylethoxy)-3-(5-chloro-1-ethyl-1H-pyrazolo[3,4-c]pyridin-7-yl)propan-2-ol This compound was synthesized by TFA deprotection as described in example 1 at step 4, except tert-butyl (S)-2-(3-(5-chloro-1-ethyl-1H-pyrazolo[3,4-c]pyridin-7-yl)-2-hydroxypropoxy)-1-phenylethylcarbamate was used. MS (EI) calc'd for $C_{19}H_{24}ClN_4O_2$ [M+H]$^+$ 375, found 375.

Step 4: 1-((1S)-2-(3-(5-Chloro-1-ethyl-1H-pyrazolo [3,4-c]pyridin-7-yl)-2-hydroxypropoxy)-1-phenylethyl)urea This compound was synthesized by the similar procedure as described in example 1 at step 5 except 1-((S)-2-amino-2-phenylethoxy)-3-(5-chloro-1-ethyl-1H-pyrazolo[3,4-c]pyridin-7-yl)propan-2-ol was used. MS (EI) calc'd for $C_{20}H_{25}ClN_5O_2$ [M+H]$^+$ 418, found 418.

Step 5: (9S,13S)-1-Ethyl-13-hydroxy-9-phenyl-1,6,9,10,13,14-hexahydro-12H-5,15-(azeno)pyrazolo[4,3-i][1,4,6]oxadiazacyclotetradecin-7(8H)-one and (9S,13R)-1-Ethyl-13-hydroxy-9-phenyl-1,6,9,10,13,14-hexahydro-12H-5,15-(azeno)pyrazolo[4,3-i][1,4,6]oxadiazacyclotetradecin-7(8H)-one These compounds were synthesized by the similar Buchwald coupling as described in example 1 at step 6 except 1-((1S)-2-(3-(5-chloro-1-ethyl-1H-pyrazolo[3,4-c]pyridin-7-yl)-2-hydroxypropoxy)-1-phenylethyl)urea was used. The two isomers were separated by chiral HPLC.

(9S,13R)-1-Ethyl-13-hydroxy-9-phenyl-1,6,9,10,13,14-hexahydro-12H-5,15-(azeno)pyrazolo[4,3-i][1,4,6]oxadiazacyclotetradecin-7(8H)-one: MS (EI) calc'd for $C_{20}H_{24}N_5O_3$ [M+H]$^+$ 382, found 382; $^1$H NMR (400 MHz, DMSO-$d_6$): δ 11.55 (d, J=8.0 Hz, 1H), 9.23 (s, 1 H), 8.08 (s, 1 H), 7.40-7.31 (m, 4 H), 7.23 (t, J=7.2 Hz, 1 H), 7.03 (s, 1 H), 5.22 (d, J=4.8 Hz, 1 H), 4.83-4.81 (m, 1 H), 4.78-4.73 (m, 1 H), 4.60-4.55 (m, 1 H), 4.37 (br s, 1 H), 4.01 (d, J=10.0 Hz, 1 H), 3.64-3.41 (m, 4 H), 3.35-3.34 (m, 1 H), 1.40 (t, J=7.2 Hz, 3 H).

(9S,13S)-1-Ethyl-13-hydroxy-9-phenyl-1,6,9,10,13,14-hexahydro-12H-5,15-(azeno)pyrazolo[4,3-i][1,4,6]oxadiazacyclotetradecin-7(8H)-one: MS (EI) calc'd for $C_{20}H_{24}N_5O_3$ [M+H]$^+$ 382, found 382; $^1$H NMR (400 MHz, DMSO-$d_6$): δ 11.71 (d, J=7.2 Hz, 1 H), 9.17 (s, 1 H), 8.11 (s, 1 H), 7.40-7.32 (m, 4 H), 7.24 (t, J=7.2 Hz, 1 H), 7.04 (s, 1 H), 5.28 (d, J=4.8 Hz, 1 H), 4.81-4.79 (m, 1 H), 4.62-4.56 (m, 2 H), 4.02-4.00 (m, 1 H), 3.85-3.81 (m, 1 H), 3.63-3.60 (m, 1 H), 3.52-3.39 (m, 3 H), 3.25-3.22 (m, 1H), 1.43 (t, J=7.0 Hz, 3 H).

Example 5

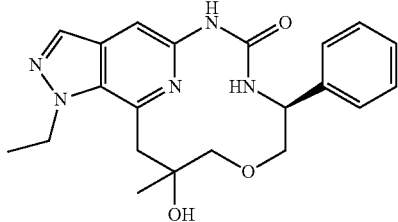 [SMILES: CCn1ncc2cc3nc(c21)CC(C)(O)COC[C@H](c1ccccc1)NC(=O)N3]

(9S)-1-Ethyl-13-hydroxy-13-methyl-9-phenyl-1,6,9,10,13,14-hexahydro-12H-5,15-(azeno)pyrazolo[4,3-i][1,4,6]oxadiazacyclotetradecin-7(8H)-one To a stirred mixture of (9S,13S)-1-ethyl-13-hydroxy-9-phenyl-1,6,9,10,13,14-hexahydro-12H-5,15-(azeno)pyrazolo[4,3-i][1,4,6]oxadiazacyclotetradecin-7(8H)-one (15 mg, 0.038 mmol) in MeCN (5 mL) was added IBX (40 mg, 0.14 mmol). After stirring for 1 h at 80° C., the resulting mixture was filtered and concentrated under reduced pressure. The residue was dissolved in dry THF (5 mL) and then methylmagnesium bromide (3 mL, 9.00 mmol) was added dropwise at 0° C. under nitrogen. The reaction mixture was stirred for 10 h at 25° C. and then quenched by saturated NH$_4$Cl, extracted with EtOAc, washed with saturated NaHCO$_3$, brine, dried (Na$_2$SO$_4$), filtered and concentrated under reduced pressure. The residue was purified by Prep-HPLC to give (9S)-1-ethyl-13-hydroxy-13-methyl-9-phenyl-1,6,9,10,13,14-hexahydro-12H-5,15-(azeno)pyrazolo[4,3-i][1,4,6]oxadiazacyclotetradecin-7(8H)-one. MS (EI) calc'd for C$_{21}$H$_{26}$N$_5$O$_3$ [M+H]$^+$ 396, found 396; $^1$H NMR (400 MHz, DMSO-d$_6$): δ 12.09 (d, J=8.4 Hz, 1 H), 9.19 (s, 1 H), 8.09 (s, 1 H), 7.43-7.34 (m, 4 H), 7.26 (t, J=7.2 Hz, 1 H), 7.05 (s, 1 H), 4.91-4.86 (m, 3 H), 4.64-4.61 (m, 1 H), 3.99 (d, J=9.6 Hz, 1 H), 3.44-3.37 (m, 2 H), 3.21 (d, J=13.6 Hz, 1 H), 3.13 (s, 2 H), 1.42 (t, J=7.2 Hz, 3H), 1.35 (s, 3 H).

Synthetic Method 3

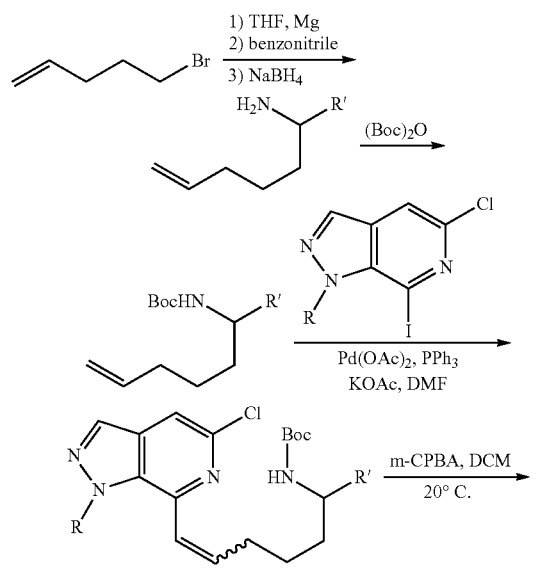

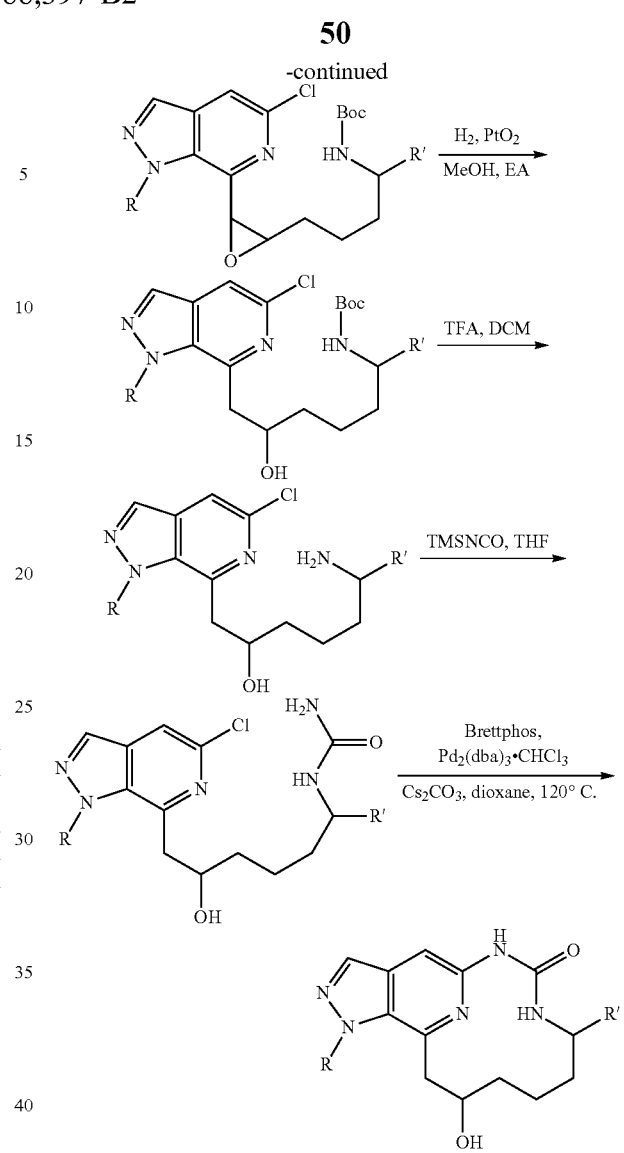

Example 6

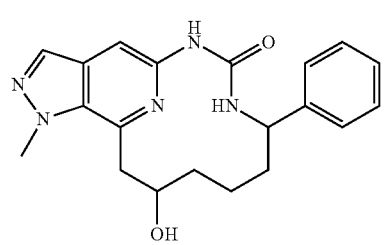 [SMILES: Cn1ncc2cc3nc(c21)CC(O)CCCC(c1ccccc1)NC(=O)N3]

13-Hydroxy-1-methyl-9-phenyl-1,6,9,10,11,12,13,14-octahydro-5,15-(azeno)pyrazolo[4,3-f][1,3]diazacyclotetradecin-7(8H)-one Step 1: 1-Phenylhex-5-en-1-amine To a solution of 5-bromopent-1-ene (6.0 g, 40.3 mmol) in THF (50 mL) was added magnesium (1.2 g, 48.4 mmol) and the mixture was stirred at 70° C. for 2 h under nitrogen. Then the solution was cooled to ambient temperature, and benzonitrile (4.2 g, 40.3 mmol) was added. The resulting mixture was stirred at ambient temperature for 2 h, and sodium borohydride (4.6 g, 121 mmol) was added. After stirring for 16 h, the reaction mixture was quenched by water, extracted with EtOAc, washed with brine, dried (Na$_2$SO$_4$), and filtered. The filtrate was concentrated under reduced pressure. The residue was purified by chromatography on SiO$_2$, eluting with petroleum ether/EtOAc (5:1) to give 1-phenylhex-5-en-1-amine. MS (EI) calc'd for C$_{12}$H$_{18}$N [M+H]$^+$ 176, found 176.

Step 2: tert-Butyl (1-phenylhex-5-en-1-yl)carbamate

To a solution of 1-phenylhex-5-en-1-amine (1.0 g, 5.71 mmol) in DCM (50 mL) was added TEA (1.2 g, 11.4 mmol), and di-tert-butyl dicarbonate (1.9 g, 8.56 mmol). The reaction mixture was stirred for 12 h at 25° C. The reaction mixture was diluted with DCM, washed with brine, dried (Na$_2$SO$_4$), filtered and concentrated under reduced pressure. The residue was purified by chromatography on SiO$_2$, eluting with petroleum ether/EtOAc (20:1) to give tert-butyl (1-phenylhex-5-en-1-yl)carbamate. MS (EI) calc'd for C$_{17}$H$_{26}$NO$_2$ [M+H]$^+$ 276, found 276.

Step 3: tert-Butyl (6-(5-chloro-1-methyl-1H-pyrazolo[3,4-c]pyridin-7-yl)-1-phenylhex-5-en-1-yl)carbamate This compound was synthesized by the similar Heck coupling as described in example 1 at step 6, except tert-butyl (1-phenylhex-5-en-1-yl)carbamate was used. MS (EI) calc'd for C$_{24}$H$_{30}$ClN$_4$O$_2$ [M+H]$^+$ 441, found 441.

Step 4: tert-Butyl 4-(3-(5-chloro-1-methyl-1H-pyrazolo [3,4-c] pyridin-7-yl)oxiran-2-yl)-1-phenylbutylcarbamate This compound was synthesized by the similar epoxidation as described in example 3 at step 1, except tert-butyl (6-(5-chloro-1-methyl-1H-pyrazolo[3,4-c]pyridin-7-yl)-1-phenylhex-5-en-1-yl)carbamate was used. MS (EI) calc'd for C$_{24}$H$_{30}$ClN$_4$O$_3$ [M+H]$^+$ 457, found 457.

Step 5: tert-Butyl 6-(5-chloro-1-methyl-1H-pyrazolo [3,4-c]pyridin-7-yl)-5-hydroxy-1-phenylhexylcarbamate This compound was synthesized by the similar hydrogenation as described in example 3 at step 2 except tert-butyl 4-(3-(5-chloro-1-methyl-1H-pyrazolo[3,4-c]pyridin-7-yl) oxiran-2-yl)-1-phenylbutylcarbamate was used. MS (EI) calc'd for C$_{24}$H$_{32}$ClN$_4$O$_3$ [M+H]$^+$ 459, found 459.

Step 6: 6-Amino-1-(5-chloro-1-methyl-1H-pyrazolo [3,4-c]pyridin-7-yl)-6-phenylhexan-2-ol This compound was synthesized by TFA deprotection as described in example 1 at step 4 except tert-butyl 6-(5-chloro-1-methyl-1H-pyrazolo[3,4-c]pyridin-7-yl)-5-hydroxy-1-phenylhexylcarbamate was used. MS (EI) calc'd for C$_{19}$H$_{24}$ClN$_4$O [M+H]$^+$ 359, found 359.

Step 7: 1-(6-(5-Chloro-1-methyl-1H-pyrazolo [3,4-c]pyridin-7-yl)-5-hydroxy-1-phenylhexyl)urea This compound was synthesized by similar urea formation as described in example 1 at step 5 except 6-amino-1-(5-chloro-1-methyl-1H-pyrazolo[3,4-c]pyridin-7-yl)-6-phenylhexan-2-ol was used. MS (EI) calc'd for C$_{20}$H$_{25}$ClN$_5$O$_2$ [M+H]$^+$ 402, found 402.

Step 8: 13-Hydroxy-1-methyl-9-phenyl-1,6,9,10,11,12,13,14-octahydro-5,15-(azeno)pyrazolo[4,3-f][1,3] diazacyclotetradecin-7(8H)-one This compound was synthesized by the similar Buchwald coupling as described in example 1 at step 6 except 1-(6-(5-chloro-1-methyl-1H-pyrazolo[3,4-c]pyridin-7-yl)-5-hydroxy-1-phenylhexyl)urea was used. ($^1$H NMR showed it was a mixture of diastereomers): MS (EI) calc'd for C$_{20}$H$_{24}$N$_5$O$_2$ [M+H]$^+$ 366, found 366; $^1$H NMR (300 MHz, CD$_3$OD): δ 11.59 (d, J=6.0 Hz, 0.5 H), 11.30 (d, J=5.4 Hz, 0.5 H), 7.97, 7.96 (ss, 1 H), 7.36-7.24 (m, 5 H), 7.03, 7.01 (ss, 1 H), 5.12-5.08 (m, 0.5 H), 4.79-4.71 (m, 1 H), 4.57-4.52 (m, 0.5 H), 4.37, 4.36 (ss, 3 H), 3.80-3.55 (m, 2 H), 2.40-2.38 (m, 1 H), 2.18-2.09 (m, 1 H), 1.89-1.82 (m, 2 H). Synthetic Method 4

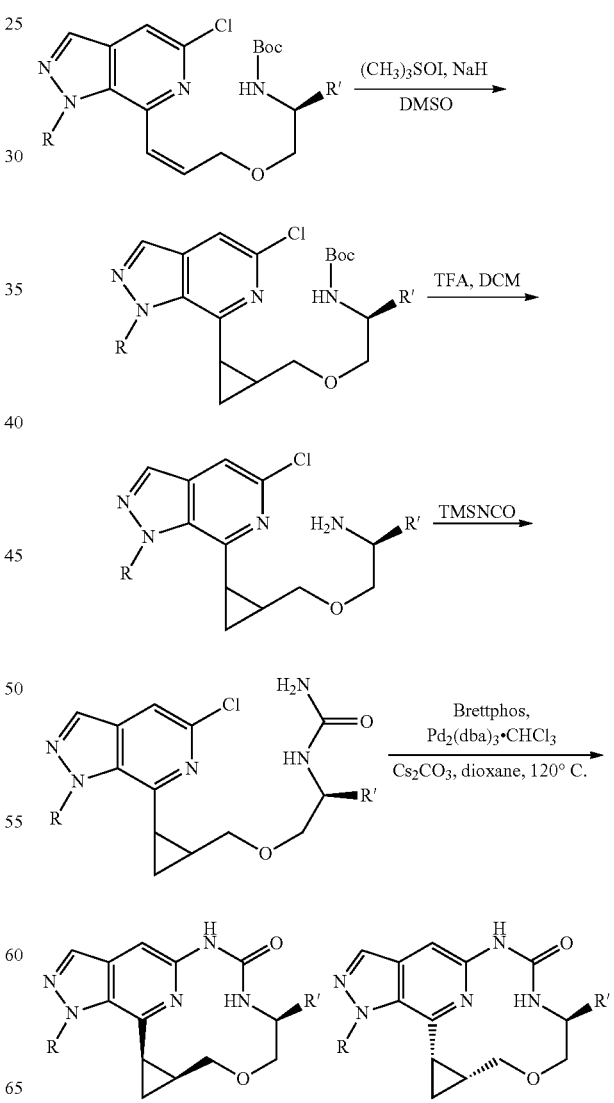

Example 7

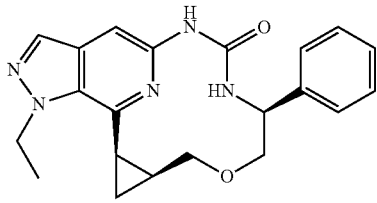 [SMILES: CCn1ncc2cc3nc(c21)[C@@H]1C[C@@H]1COC[C@H](c1ccccc1)NC(=O)N3]

(9S,12aS,13 aR)-1-Ethyl-9-phenyl-1,6,9,10,12,12a,
13,13a-octahydro-5,14-(azeno)cyclopropa[1]pyrazolo
[4,3-i][1,4,6]oxadiazacyclotetradecin-7(8H)-one

Example 8

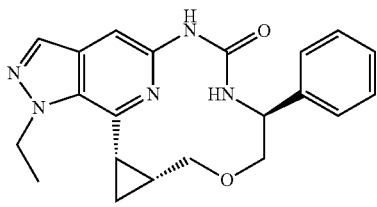 [SMILES: CCn1ncc2cc3nc(c21)[C@H]1C[C@H]1COC[C@H](c1ccccc1)NC(=O)N3]

(9S,12aR,13aS)-1-Ethyl-9-phenyl-1,6,9,10,12,12a,
13,13a-octahydro-5,14-(azeno)cyclopropa[1]pyra-
zolo[4,3-i][1,4,6]oxadiazacyclotetradecin-7(8H)-one

Step 1: tert-Butyl ((1S)-2-((2-(5-chloro-1-ethyl-1H-pyrazolo[3,4-c]pyridin-7-yl)cyclopropyl)methoxy)-1-phenylethyl)carbamate To a solution of (S,Z)-tert-butyl (2-((3-(5-chloro-1-ethyl-1H-pyrazolo[3,4-c]pyridin-7-yl)allyl)oxy)-1-phenylethyl)carbamate (860 mg, 1.88 mmol) in DMSO (10 mL) under nitrogen was added sodium hydride (151 mg, 3.76 mmol) and trimethylsulfoxonium iodide (828 mg, 3.76 mmol). The resulting mixture was stirred for 16 h at 25° C. and then quenched by water. The resulting solution was extracted with EtOAc, washed with saturated NaHCO$_3$, brine, dried (Na$_2$SO$_4$), filtered and concentrated under reduced pressure. The residue was purified by chromatography on SiO$_2$, eluted with petroleum ether/EtOAc (1:1) to give tert-butyl ((1S)-2-((2-(5-chloro-1-ethyl-1H-pyrazolo[3,4-c]pyridin-7-yl)cyclopropyl)methoxy)-1-phenylethyl)carbamate. MS (EI) calc'd for C$_{25}$H$_{32}$ClN$_4$O$_3$ [M+H]$^+$ 471, found 471.

Step 2: (1S)-2-((2-(5-Chloro-1-ethyl-1H-pyrazolo[3,4-c]pyridin-7-yl)cyclopropyl)methoxy)-1-phenylethanamine This compound was synthesized by TFA deprotection as described in example 1 at step 4 except tert-butyl ((1S)-2-((2-(5-chloro-1-ethyl-1H-pyrazolo[3,4-c]pyridin-7-yl)cyclopropyl)methoxy)-1-phenylethyl)carbamate was used. MS (EI) calc'd for C$_{20}$H$_{24}$ClN$_4$O [M+H]$^+$ 371, found 371.

Step 3: 1-((1S)-2-((2-(5-chloro-1-ethyl-1H-pyrazolo[3,4-c]pyridin-7-yl)cyclopropyl)methoxy)-1-phenylethyl)urea This compound was synthesized by the similar urea formation as described in example 1 at step 5 except (1S)-2-((2-(5-chloro-1-ethyl-1H-pyrazolo[3,4-c]pyridin-7-yl)cyclopropyl)methoxy)-1-phenylethanamine was used. MS (EI) calc'd for C$_{21}$H$_{25}$ClN$_5$O$_2$ [M+H]$^+$ 414, found 414.

Step 4: (9S,12aS,13aR)-1-Ethyl-9-phenyl-1,6,9,10, 12,12a,13,13a-octahydro-5,14-(azeno)cyclopropa[1]pyrazolo[4,3-i][1,4,6]oxadiazacyclotetradecin-7 (8H)-one and (9S,12aR,13aS)-1-Ethyl-9-phenyl-1,6, 9,10,12,12a,13,13a-octahydro-5,14-(azeno) cyclopropa[1]pyrazolo[4,3-i][1,4,6] oxadiazacyclotetradecin-7(8H)-one These compounds were synthesized by the similar Buchwald coupling as described in example 1 at step 6 except 1-((1S)-2-((2-(5-chloro-1-ethyl-1H-pyrazolo[3,4-c]pyridin-7-yl)cyclopropyl)methoxy)-1-phenylethyl)urea was used. The two isomers were separated by chiral HPLC.

(9S,12aS,13aR) or (9S,12aR,13aS)-1-Ethyl-9-phenyl-1,6,9,10,12,12a,13,13a-octahydro-5,14-(azeno)cyclopropa[1]pyrazolo[4,3-i][1,4,6]oxadiazacyclotetradecin-7(8H)-one: MS (EI) calc'd for C$_{21}$H$_{24}$N$_5$O$_2$ [M+H]$^+$ 378, found 378; $^1$H NMR (400 MHz, DMSO-d$_6$): δ 12.56 (d, J=6.4 Hz, 1 H), 9.24 (s, 1 H), 8.12 (s, 1 H), 7.35-7.30 (m, 4 H), 7.20 (t, J=7.2 Hz, 1 H), 6.98 (s, 1 H), 4.82-4.64 (m, 3 H), 4.06 (t, J=10.4 Hz, 2 H), 3.89 (m, 1 H), 3.19 (t, J=11.8 Hz, 1 H), 2.56-2.50 (m, 1 H), 1.80-1.78 (m, 1 H), 1.47 (t, J=7.2 Hz, 3 H), 1.43-1.39 (m, 1 H), 1.21-1.16 (m, 1 H).

(9S,12aR,13aS) or (9S,12aS,13aR)-1-Ethyl-9-phenyl-1,6, 9,10,12,12a,13,13a-octahydro-5,14-(azeno)cyclopropa[1]pyrazolo[4,3-i][1,4,6]oxadiazacyclotetradecin-7(8 H)-one: MS (EI) calc'd for C$_{21}$H$_{24}$N$_5$O$_2$ [M+H]$^+$ 378, found 378; $^1$H NMR (400 MHz, DMSO-d$_6$): δ 12.25 (s, 1 H), 9.12 (s, 1 H), 8.12 (s, 1 H), 7.36-7.29 (m, 4 H), 7.23 (t, J=7.0 Hz, 1 H), 6.96 (s, 1 H), 4.77-4.68 (m, 2 H), 4.60 (m, 1 H), 3.94 (m, 1 H), 3.82 (m, 1 H), 3.43 (t, J=10.6 Hz, 1 H), 3.33-3.27 (m, 1 H), 2.47-2.43 (m, 1 H), 1.82 (br s, 1 H), 1.53-1.45 (m, 4 H), 1.25-1.22 (m, 1 H).

Synthetic Method 5

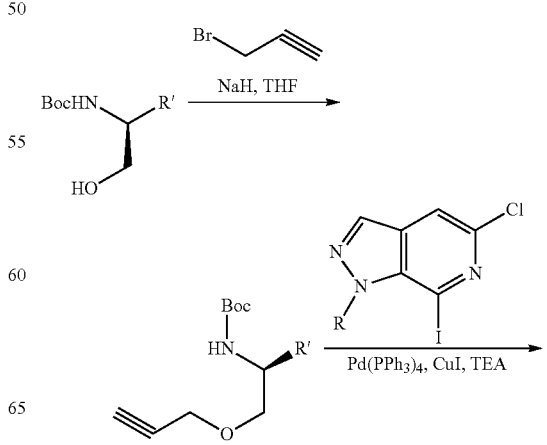

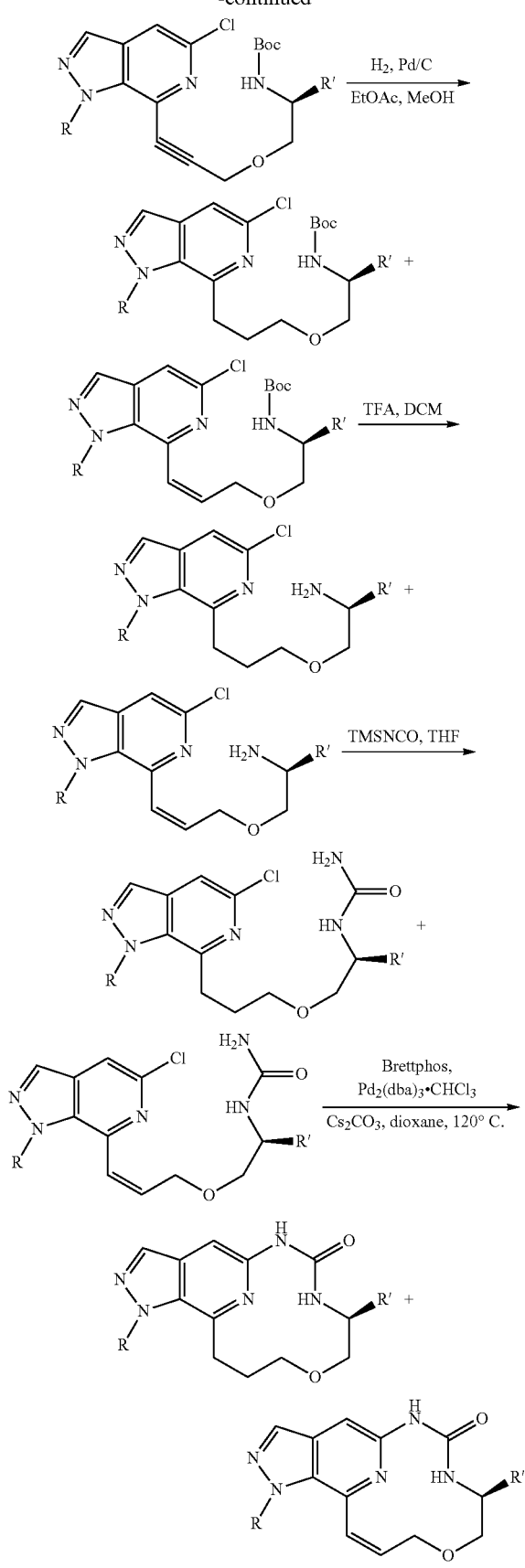

Example 9

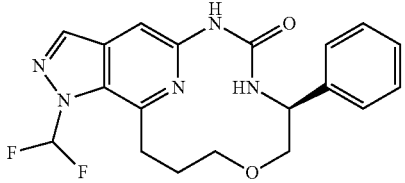

(9S)-1-(Difluoromethyl)-9-phenyl-1,6,9,10,13,14-hexahydro-12H-5,15-(azeno)pyrazolo[4,3-i][1,4,6]oxadiazacyclotetradecin-7(8H)-one Example 10

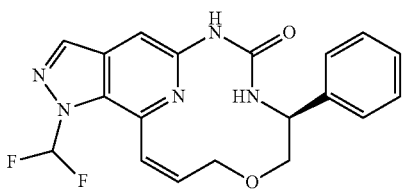 [SMILES: O=C1Nc2cc3cnn(C(F)F)c3c(n2)/C=C\COC[C@H](c2ccccc2)N1]

(9S,13Z)-1-(Difluoromethyl)-9-phenyl-1,6,9,10-tetrahydro-12H-5,15-(azeno)pyrazolo[4,3-i][1,4,6]oxadiazacyclotetradecin-7(8H)-one Step 1: (S)-tert-Butyl (1-phenyl-2-(prop-2-yn-1-yloxy)ethyl)carbamate This compound was synthesized by the similar alkylation as described in example 1 at step 1 except (S)-tert-butyl (2-hydroxy-1-phenylethyl)carbamate (10 g, 42.1 mmol) and propargyl bromide (7.52 g, 63.2 mmol) were used. MS (EI) calc'd for $C_{16}H_{22}NO_3$ [M+H]$^+$ 276, found 276.

Step 2: (S)-tert-Butyl 2-(3-(5-chloro-1-(difluoromethyl)-1H-pyrazolo[3,4-c]pyridin-7-yl)prop-2-ynyloxy)-1-phenylethylcarbamate A mixture of (S)-tert-butyl (1-phenyl-2-(prop-2-yn-1-yloxy)ethyl)carbamate (1.5 g, 5.46 mmol), 5-chloro-1-(difluoromethyl)-7-iodo-1H-pyrazolo[3,4-c]pyridine (1.80 g, 5.46 mmol), Pd(PPh$_3$)$_4$ (316 mg, 0.27 mmol), copper(I) iodide (52.0 mg, 0.27 mmol) and TEA (553 mg, 5.46 mmol) in MeCN (10 mL) was stirred at 25° C. for 3 h under nitrogen. The resulting mixture was concentrated under vacuum. The residue was diluted with water, extracted with EtOAc, washed with brine, dried (Na$_2$SO$_4$), filtered and concentrated under reduced pressure. The crude product was purified by chromatography on SiO$_2$, eluted with petroleum ether/EtOAc (5:1) to give (S)-tert-butyl 2-(3-(5-chloro-1-(difluoromethyl)-1H-pyrazolo[3,4-c]pyridin-7-yl)prop-2-ynyloxy)-1-phenylethylcarbamate. MS (EI) calc'd for $C_{23}H_{24}ClF_2N_4O_3$ [M+H]$^+$ 477, found 477.

Step 3: (S)-tert-Butyl 2-(3-(5-chloro-1-(difluoromethyl)-1H-pyrazolo[3,4-c]pyridin-7-yl)propoxy)-1-phenylethylcarbamate and (S,Z)-tert-butyl 2-(3-(5-chloro-1-(difluoromethyl)-1H-pyrazolo[3,4-c]pyridin-7-yl)allyloxy)-1-phenylethylcarbamate A suspension of (S)-tert-butyl 2-(3-(5-chloro-1-(difluoromethyl)-1H-pyrazolo[3,4-c]pyridin-7-yl)prop-2-ynyloxy)-1-phenylethylcarbamate (500 mg, 1.05 mmol) and 10% Pd/C (200 mg, 1.88 mmol) in EtOAc (15 mL) was purged in 2~4 atm. hydrogen and stirred for 5 h at 25° C. under an atmosphere of hydrogen (2~4 atm.). The reaction mixture was filtered and concentrated under reduced pressure. The residue was used directly for the next step without further purification. LCMS showed the major product was (S)-tert-butyl 2-(3-(5-chloro-1-(difluoromethyl)-1H-pyrazolo[3,4-c]pyridin-7-yl)propoxy)-1-phenylethylcarbamate (MS (EI) calc'd for $C_{23}H_{28}ClF_2N_4O_3$ [M+H]$^+$ 481, found 481); ~10% of (S,Z)-tert-butyl 2-(3-(5-chloro-1-(difluoromethyl)-1H-pyrazolo[3,4-c]pyridin-7-yl)allyloxy)-1-phenylethylcarbamate was contained: MS (EI) calc'd for $C_{23}H_{26}ClF_2N_4O_3$ [M+H]$^+$ 479, found 479.

Step 4: (S)-2-(3-(5-Chloro-1-(difluoromethyl)-1H-pyrazolo[3,4-c]pyridin-7-yl)propoxy)-1-phenyl ethanamine and (S,Z)-2-(3-(5-chloro-1-(difluoromethyl)-1H-pyrazolo[3,4-c]pyridin-7-yl)allyloxy)-1-phenylethanamine These compounds were synthesized by similar TFA deprotection as described in example 1 at step 4 except a mixture of (S)-tert-butyl 2-(3-(5-chloro-1-(difluoromethyl)-1H-pyrazolo[3,4-c]pyridin-7-yl)propoxy)-1-phenylethylcarbamate and (S,Z)-tert-butyl 2-(3-(5-chloro-1-(difluoromethyl)-1H-pyrazolo[3,4-c]pyridin-7-yl)allyloxy)-1-phenylethylcarbamate was used. (S)-2-(3-(5-chloro-1-(difluoromethyl)-1H-pyrazolo[3,4-c]pyridin-7-yl)propoxy)-1-phenyl ethanamine: MS (EI) calc'd for $C_{18}H_{20}ClF_2N_4O$ [M+H]$^+$ 381, found 381. (S,Z)-2-(3-(5-chloro-1-(difluoromethyl)-1H-pyrazolo[3,4-c]pyridin-7-yl)allyloxy)-1-phenylethanamine. MS (EI) calc'd for $C_{18}H_{18}ClF_2N_4O$ [M+H]$^+$ 379, found 379.

Step 5: (S)-1-(2-(3-(5-Chloro-1-(difluoromethyl)-1H-pyrazolo[3,4-c]pyridin-7-yl)propoxy)-1-phenylethyl)urea and (S,Z)-1-(2-(3-(5-chloro-1-(difluoromethyl)-1H-pyrazolo[3,4-c]pyridin-7-yl)allyloxy)-1-phenylethyl)urea These compounds were synthesized by similar urea formation as described in example 1 at step 5 except a mixture of (S)-2-(3-(5-chloro-1-(difluoromethyl)-1H-pyrazolo[3,4-c]pyridin-7-yl)propoxy)-1-phenylethanamine and (S,Z)-2-(3-(5-chloro-1-(difluoromethyl)-1H-pyrazolo[3,4-c]pyridin-7-yl)allyloxy)-1-phenylethanamine was used. (S)-1-(2-(3-(5-chloro-1-(difluoromethyl)-1H-pyrazolo[3,4-c]pyridin-7-yl)propoxy)-1-phenylethyl)urea: MS (EI) calc'd for $C_{19}H_{21}ClF_2N_5O_2$ [M+H]$^+$ 424, found 424. (S,Z)-1-(2-(3-(5-chloro-1-(difluoromethyl)-1H-pyrazolo[3,4-c]pyridin-7-yl)allyloxy)-1-phenylethyl)urea: MS (EI) calc'd for $C_{19}H_{19}ClF_2N_5O_2$ [M+H]$^+$ 422, found 422.

Step 6: (9S)-1-(Difluoromethyl)-9-phenyl-1,6,9,10,13,14-hexahydro-12H-5,15-(azeno)pyrazolo[4,3-i][1,4,6]oxadiazacyclotetradecin-7(8H)-one and (9S,13Z)-1-(Difluoromethyl)-9-phenyl-1,6,9,10-tetrahydro-12H-5,15-(azeno)pyrazolo[4,3-i][1,4,6]oxadiazacyclotetradecin-7(8H)-one These compounds were synthesized by the Buchwald coupling as described in example 1 at step 6 except a mixture of (S)-1-(2-(3-(5-chloro-1-(difluoromethyl)-1H-pyrazolo[3,4-c]pyridin-7-yl)propoxy)-1-phenylethyl)urea and (S,Z)-1-(2-(3-(5-chloro-1-(difluoromethyl)-1H-pyrazolo[3,4-c]pyridin-7-yl)allyloxy)-1-phenylethyl)urea was used. The two desired products were separated by Prep-HPLC.

(9S)-1-(Difluoromethyl)-9-phenyl-1,6,9,10,13,14-hexahydro-12H-5,15-(azeno)pyrazolo[4,3-i][1,4,6]oxadiazacyclotetradecin-7(8H)-one: MS (EI) calc'd for $C_{19}H_{20}F_2N_5O_2$ [M+H]$^+$ 388, found 388; $^1$H NMR (300 MHz, CDCl$_3$): δ 11.46 (d, J=6.4 Hz, 1 H), 8.22 (s, 1 H), 7.83 (s, 1 H), 7.47 (t, J=7.2 Hz, 2 H), 7.35 (t, J=7.2 Hz, 2 H), 7.27-7.22 (m, 2 H), 6.68 (s, 1 H), 5.01-4.97 (m, 1 H), 4.04-3.99 (m, 1 H), 3.91-3.84 (m, 1 H), 3.74-3.59 (m, 2 H), 3.45-3.38 (m, 2 H), 2.39-2.33 (m, 1 H), 2.18-2.13 (m, 1 H).

(9S,13Z)-1-(Difluoromethyl)-9-phenyl-1,6,9,10-tetrahydro-12H-5,15-(azeno)pyrazolo[4,3-i][1,4,6]oxadiazacyclotetradecin-7(8 H)-one: MS (EI) calc'd for $C_{19}H_{18}F_2N_5O_2$ [M+H]$^+$ 386, found 386; $^1$H NMR (300 MHz, CDCl$_3$): δ 11.55 (d, J=6.4 Hz, 1 H), 8.18 (s, 1 H), 8.06 (s, 1 H), 7.75 (t, J=13.5 Hz, 1 H), 7.47-7.45 (m, 2 H), 7.36-7.22 (m, 4 H), 6.94 (s, 1 H), 6.38-6.29 (m, 1 H), 5.16-5.10 (m, 1 H), 4.67-4.61 (m, 1 H), 4.30-4.22 (m, 2 H), 3.89-3.79 (m, 1 H).

Synthetic Method 6

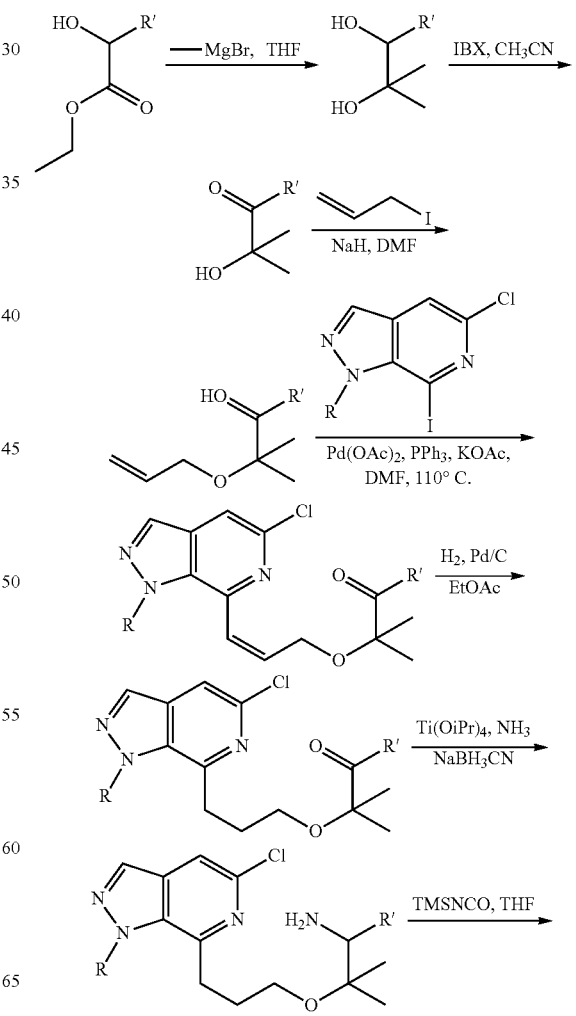

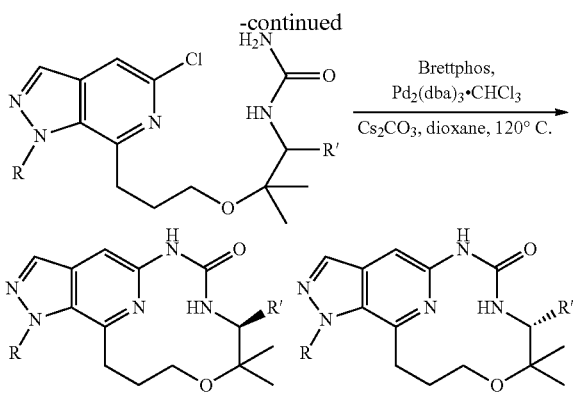

Example 11

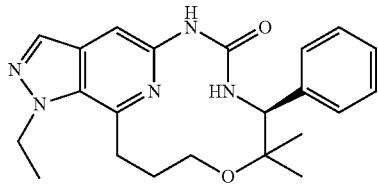

(9S)-1-Ethyl-10, 10-dimethyl-9-phenyl-1,6,9,10,13,
14-hexahydro-12H-5,15-(azeno)pyrazolo [4,3-i][1,4,
6]oxadiazacyclotetradecin-7(8H)-one Example 12

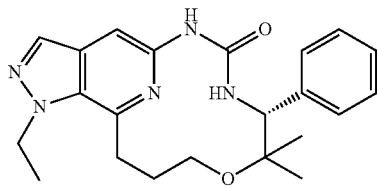 [SMILES: CCn1ncc2cc3nc(c21)CCCOC(C)(C)[C@@H](c1ccccc1)NC(=O)N3]

(9R)-1-Ethyl-10,10-dimethyl-9-phenyl-1,6,9,10,13,
14-hexahydro-12H-5,15-(azeno)pyrazolo[4,3-i][1,4,
6]oxadiazacyclotetradecin-7(8H)-one Step 1: 2-Methyl-1-phenylpropane-1,2-diol Methylmagnesium bromide (185 mL, 555 mmol) was added dropwise to a stirred, cooled (−60° C.) solution of ethyl 2-hydroxy-2-phenylacetate (20 g, 111 mmol) in dry THF (200 mL) under nitrogen. The mixture was stirred for 10 h at 25° C. and then quenched by saturated NH$_4$Cl, extracted with EtOAc, washed with saturated NaHCO$_3$ and brine, dried (Na$_2$SO$_4$), and filtered. The filtrate was concentrated under reduced pressure to give 2-methyl-1-phenylpropane-1, 2-diol. MS (EI) calc'd for C$_{10}$H$_{15}$O$_2$ [M+H]$^+$ 167, found 167; $^1$H NMR (400 MHz, DMSO): δ 7.35-7.34 (m, 2 H), 7.29-7.25 (m, 2 H), 7.22-7.19 (m, 1 H), 5.16 (d, J=4.4 Hz, 1 H), 4.31 (d, J=4.4 Hz, 1 H), 4.22 (s, 1 H), 1.05 (s, 3 H), 0.96 (s, 3 H).

Step 2: 2-Hydroxy-2-methyl-1-phenylpropan-1-one

IBX (30.3 g, 108 mmol) was added to a stirred mixture of 2-methyl-1-phenylpropane-1, 2-diol (9 g, 54.1 mmol) in MeCN (100 mL). After stirring for 1 h at 80° C., the resulting mixture was filtered and concentrated under reduced pressure. The residue was purified by chromatography on SiO$_2$, eluted with petroleum ether/EtOAc (1:1) to give 2-hydroxy-2-methyl-1-phenylpropan-1-one. MS (EI) calc'd for C$_{10}$H$_{13}$O$_2$ [M+H]$^+$ 165, found 165; $^1$H NMR (300 MHz, DMSO): δ 8.18-8.14 (m, 2 H), 7.60-7.55 (m, 1 H), 7.50-7.44 (m, 2 H), 5.70 (s, 1 H), 1.41 (s, 6 H).

Step 3: 2-(Allyloxy)-2-methyl-1-phenylpropan-1-one

This compound was synthesized by the similar alkylation procedure as described in example 1 at step 1 except 2-hydroxy-2-methyl-1-phenylpropan-1-one was used. MS (EI) calc'd for C$_{13}$H$_{17}$O$_2$ [M+H]$^+$ 205, found 205; $^1$H NMR (300 MHz, CDCl$_3$): δ 7.64-7.59 (m, 2 H), 7.45-7.37 (m, 3 H), 6.07-5.95 (m, 1 H), 5.32-5.25 (m, 1 H), 5.18-5.13 (m, 1 H), 4.17-4.14 (m, 2 H), 1.57 (s, 3 H), 0.99 (s, 3 H).

Step 4: 2-(3-(5-Chloro-1-ethyl-1H-pyrazolo[3,4-c] pyridin-7-yl)allyloxy)-2-methyl-1-phenylpropan-1-one This compound was synthesized by similar palladium coupling as described in example 1 at step 2 except 2-(allyloxy)-2-methyl-1-phenylpropan-1-one was used. MS (EI) calc'd for C$_{21}$H$_{23}$ClN$_3$O$_2$ [M+H]$^+$ 384, found 384.

Step 5: 2-(3-(5-Chloro-1-ethyl-1H-pyrazolo[3,4-c] pyridin-7-yl)propoxy)-2-methyl-1-phenylpropan-1-one This compound was synthesized by the hydrogenation procedure as described in example 1 at step 3 except 2-(3-(5-chloro-1-ethyl-1H-pyrazolo[3,4-c]pyridin-7-yl)allyloxy)-2-methyl-1-phenylpropan-1-one was used. MS (EI) calc'd for C$_{21}$H$_{25}$ClN$_3$O$_2$ [M+H]$^+$ 386, found 386.

Step 6: 2-(3-(5-Chloro-1-ethyl-1H-pyrazolo[3,4-c] pyridin-7-yl)propoxy)-2-methyl-1-phenylpropan-1-amine To a mixture of 2-(3-(5-chloro-1-ethyl-1H-pyrazolo[3,4-c]pyridin-7-yl)propoxy)-2-methyl-1-phenylpropan-1-one (730 mg, 1.90 mmol) in EtOH (15 mL) were added a solution of ammonia in MeOH (7 M, 1.35 mL, 9.51 mmol) and tetraisopropoxytitanium (1.08 g, 3.80 mmol). After stirring for 15 h at 80° C., the resulting mixture was cooled down to ambient temperature. Then sodium cyanotrihydroborate (179 mg, 2.85 mmol) was added and stirred for 2 h at 25° C. The reaction mixture was quenched by water and concentrated under reduced pressure. The residue was diluted with water, extracted with EtOAc, washed with brine, dried (Na$_2$SO$_4$), filtered and concentrated under reduced pressure. The crude product was purified by chromatography on SiO$_2$, eluted with DCM/MeOH (20/1) to give 2-(3-(5-chloro-1-ethyl-1H-pyrazolo [3, 4-c] pyridin-7-yl)propoxy)-2-methyl-1-phenylpropan-1-amine. MS (EI) calc'd for C$_{21}$H$_{28}$ClN$_4$O [M+H]$^+$ 387, found 387.

Step 7: 1-(2-(3-(5-Chloro-1-ethyl-1H-pyrazolo[3,4-c]pyridin-7-yl)propoxy)-2-methyl-1-phenylpropyl)urea This compound was synthesized by the urea formation procedure as described in example 1 at step 5 except 2-(3-(5-chloro-1-ethyl-1H-pyrazolo[3,4-c]pyridin-7-yl)propoxy)-2-methyl-1-phenylpropan-1-amine was used. MS (EI) calc'd for $C_{22}H_{29}ClN_5O_2$ [M+H]$^+$ 430, found 430.

Step 8: (9S)-1-Ethyl-10,10-dimethyl-9-phenyl-1,6,9,10,13,14-hexahydro-12H-5,15-(azeno)pyrazolo[4,3-i][1,4,6]oxadiazacyclotetradecin-7(8H)-one and (9R)-1-Ethyl-10,10-dimethyl-9-phenyl-1,6,9,10,13,14-hexahydro-12H-5,15-(azeno)pyrazolo[4,3-i][1,4,6]oxadiazacyclotetradecin-7(8H)-one These compounds were synthesized by similar Buchwald procedure as described in example 1 at step 6 except 1-(2-(3-(5-chloro-1-ethyl-1H-pyrazolo[3,4-c]pyridin-7-yl)propoxy)-2-methyl-1-phenylpropyl)urea was used. The two isomers were separated by chiral HPLC.

(9S) or (9R)-1-Ethyl-10,10-dimethyl-9-phenyl-1,6,9,10,13,14-hexahydro-12H-5,15-(azeno)pyrazolo[4,3-i][1,4,6]oxadiazacyclotetradecin-7(8H)-one: MS (EI) calc'd for $C_{22}H_{28}N_5O_2$ [M+H]$^+$ 394, found 394; $^1$H NMR (400 MHz, DMSO-$d_6$) δ 11.39 (d, J=8.8 Hz, 1 H), 9.11 (s, 1 H), 8.09 (s, 1 H), 7.41 (d, J=6.8 Hz, 2 H), 7.30 (t, J=7.2 Hz, 2 H), 7.24 (t, J=7.2 Hz, 1 H), 7.01 (s,1 H), 4.60 (q, J=7.2 Hz, 2 H), 4.48 (d, J=4.4 Hz, 1 H), 3.77-3.75 (m, 1 H), 3.62-3.60 (m, 1 H), 3.44-3.42 (m, 1 H), 3.37-3.35 (m, 1 H), 2.34-2.32 (m, 1 H), 2.17-2.14 (m, 1 H), 1.42 (t, J=7.2 Hz, 3 H), 1.30 (s, 3 H), 0.84 (s, 3 H).

(9R) or (9S)-1-Ethyl-10,10-dimethyl-9-phenyl-1,6,9,10,13,14-hexahydro-12H-5,15-(azeno)pyrazolo[4,3-i][1,4,6]oxadiazacyclotetradecin-7(8H)-one: MS (EI) calc'd for $C_{22}H_{28}N_5O_2$ [M+H]$^+$ 394, found 394; $^1$H NMR (400 MHz, DMSO-$d_6$) δ 11.39 (d, J=4.8 Hz, 1 H), 9.11 (s, 1 H), 8.09 (s, 1 H), 7.41 (d, J=6.8 Hz, 2 H), 7.30 (t, J=7.2 Hz, 2 H), 7.23 (t, J=7.2 Hz, 1 H), 7.01 (s, 1 H), 4.60 (q, J=7.2 Hz, 2 H), 4.48 (d, J=8.8 Hz, 1 H), 3.79-3.74 (m, 1 H), 3.64-3.58 (m, 1 H), 3.48-3.43 (m, 1 H), 3.37-3.31 (m, 1 H), 2.53-2.50 (m, 1 H), 2.36-2.33 (m, 1 H), 1.42 (t, J=7.2 Hz, 3 H), 1.30 (s, 3 H), 0.85 (s, 3 H).

Synthetic Method 7

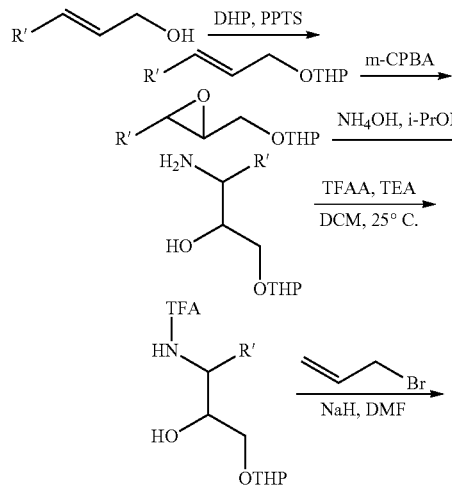

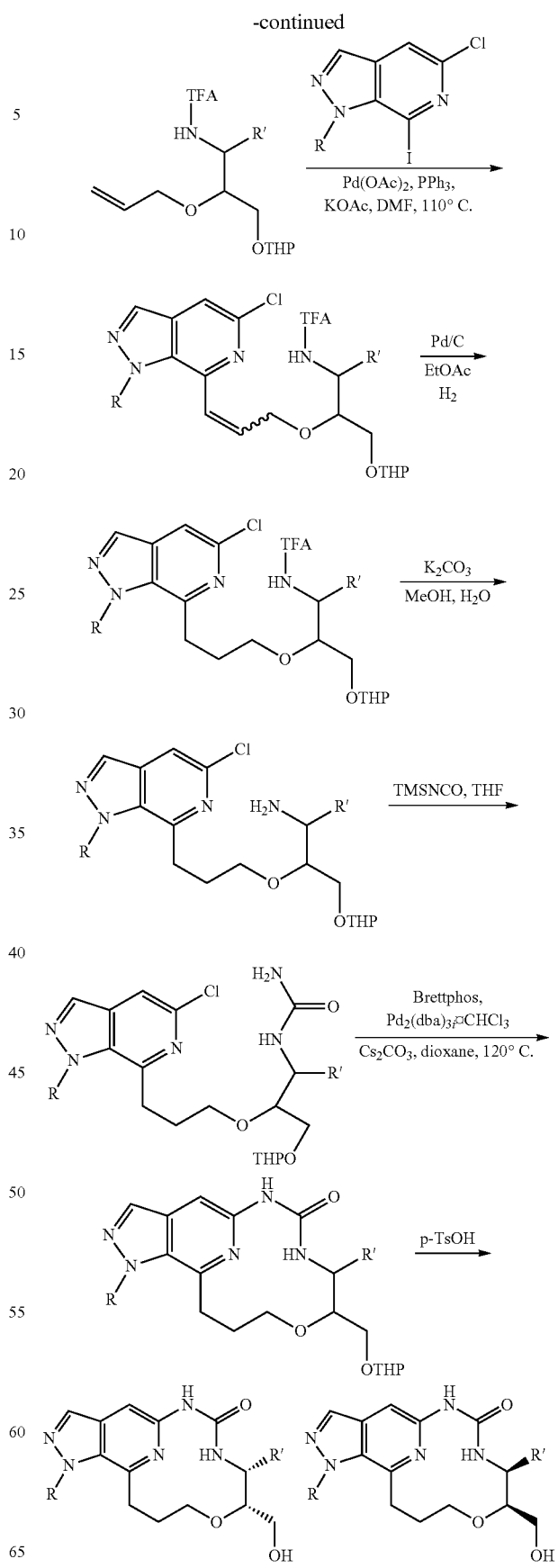

Example 13

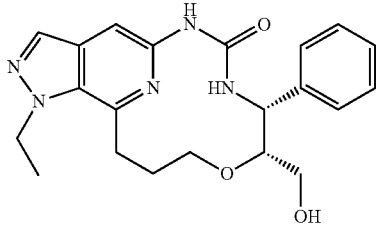 [SMILES: CCn1ncc2cc3nc(c21)CCCO[C@@H](CO)[C@@H](c1ccccc1)NC(=O)N3]

(9R,10R)-1-Ethyl-10-(hydroxymethyl)-9-phenyl-1,6,
9,10,13,14-hexahydro-12H-5,15-(azeno)pyrazolo[4,
3-i][1,4,6]oxadiazacyclotetradecin-7(8H)-one Example 14

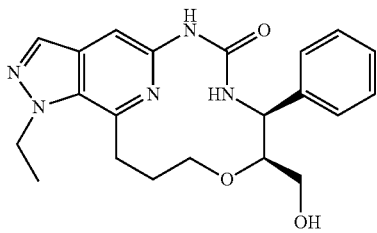 [SMILES: CCn1ncc2cc3nc(c21)CCCO[C@H](CO)[C@H](c1ccccc1)NC(=O)N3]

(9S,10S)-1-Ethyl-10-(hydroxymethyl)-9-phenyl-1,6,
9,10,13,14-hexahydro-12H-5,15-(azeno)pyrazolo[4,
3-i][1,4,6]oxadiazacyclotetradecin-7(8H)-one Step 1: 2-(Cinnamyloxy)-tetrahydro-2H-pyran Pyridinium 4-toluenesulfonate (0.47 g, 1.86 mmol) was added to a stirred mixture of (E)-3-phenylprop-2-en-1-ol (5 g, 37.3 mmol) and 3,4-dihydro-2H-pyran (4.09 mL, 44.7 mmol) in DCM (100 mL). The mixture was stirred for 12 h at 25° C. and then diluted with DCM, washed with brine, dried ($Na_2SO_4$), and filtered. The filtrate was concentrated under reduced pressure to give 2-(cinnamyloxy)-tetrahydro-2H-pyran which was used directly for the next step without further purification.

Step 2: 2-((3-Phenyloxiran-2-yl)methoxy)tetrahydro-2H-pyran

To a mixture of 2-(cinnamyloxy)tetrahydro-2H-pyran (7.50 g, 34.4 mmol) in dichloromethane (300 ml) was added mCPBA (11.86 g, 68.7 mmol). After stirring at 25° C. for 5 h, the reaction mixture was diluted with dichloromethane (100 mL), washed with saturated sodium hydrogen carbonate (3×100 mL), dried ($Na_2SO_4$) and filtered. Upon concentrated under reduced pressure, the residue was purified by chromatography on $SiO_2$, eluted with petroleum ether/EtOAc (20:1) to give 2-((3-phenyloxiran-2-yl)methoxy)tetrahydro-2H-pyran. $^1H$ NMR (400 MHz, $CDCl_3$): δ 7.40-7.29 (m, 5 H), 4.73-4.72 (m, 1 H), 3.95-3.82 (m, 4 H), 3.58-3.55 (m, 1 H), 3.28-3.26 (m, 1 H), 1.88-1.77 (m, 2 H), 1.70-1.56 (m, 4 H).

Step 3: 1-Amino-1-phenyl-3-((tetrahydro-2H-pyran-2-yl)oxy)propan-2-ol 2-((3-phenyloxiran-2-yl)methoxy)tetrahydro-2H-pyran (6 g, 25.6 mmol) was dissolved in ammonia (15 mL) and 2-propanol (30 mL). Then the solution was heated to 80° C. and stirred for 3 h in a sealed tube. The reaction mixture was cooled down to ambient temperature and the solvent was evaporated under reduced pressure. The residue was purified by chromatography on $SiO_2$, eluted with petroleum ether/EtOAc (1:5) to give 1-amino-1-phenyl-3-((tetrahydro-2H-pyran-2-yl)oxy)propan-2-ol. MS (EI) calc'd for $C_{14}H_{22}NO_3$ $[M+H]^+$ 252, found 252.

Step 4: 2,2,2-Trifluoro-N-(2-hydroxy-1-phenyl-3-((tetrahydro-2H-pyran-2-yl)oxy)propyl)acetamide Trifluoroacetic anhydride (1.61 mL, 9.55 mmol) was added dropwise to a stirred, cooled (0° C.) solution of 1-amino-1-phenyl-3-((tetrahydro-2H-pyran-2-yl)oxy)propan-2-ol (2.0 g, 7.96 mmol) in DCM (30 mL). After stirring for 2 h at 25° C., the reaction mixture was diluted with DCM, washed with Saturated $NH_4Cl$, then dried ($Na_2SO_4$), filtered and concentrated. The residue was purified by chromatography on $SiO_2$, eluted with petroleum ether/EtOAc (1:1) to afford 2,2,2-trifluoro-N-(2-hydroxy-1-phenyl-3-((tetrahydro-2H-pyran-2-yl)oxy)propyl)acetamide. MS (EI) calc'd for $C_{16}H_{21}F_3NO_4$ $[M+H]^+$ 348, found 348.

Step 5: N-(2-(Allyloxy)-1-phenyl-3-(tetrahydro-2H-pyran-2-yloxy)propyl)-2,2,2-trifluoroacetamide This compound was synthesized by similar alkylation as described in example 1 at step 1 except 2,2,2-trifluoro-N-(2-hydroxy-1-phenyl-3-((tetrahydro-2H-pyran-2-yl)oxy)propyl)acetamide was used. MS (EI) calc'd for $C_{19}H_{25}F_3NO_4$ $[M+H]^+$ 388, found 388.

Step 6: N-(2-(3-(5-Chloro-1-ethyl-1H-pyrazolo[3,4-c]pyridin-7-yl)allyloxy)-1-phenyl-3-(tetrahydro-2H-pyran-2-yloxy)propyl)-2,2,2-trifluoroacetamide This compound was synthesized by the similar palladium coupling as described in example 1 at step 2 except N-(2-(allyloxy)-1-phenyl-3-(tetrahydro-2H-pyran-2-yloxy)propyl)-2,2,2-trifluoroacetamide was used. MS (EI) calc'd for $C_{27}H_{31}ClF_3N_4O_4$ $[M+H]^+$ 567, found 567.

Step 7: N-(2-(3-(5-Chloro-1-ethyl-1H-pyrazolo[3,4-c]pyridin-7-yl)propoxy)-1-phenyl-3-(tetrahydro-2H-pyran-2-yloxy)propyl)-2,2,2-trifluoroacetamide This compound was synthesized by the similar hydrogenation as described in example 1 at step 3 except N-(2-(3-(5-chloro-1-ethyl-1H-pyrazolo[3,4-c]pyridin-7-yl)allyloxy)-1-phenyl-3-(tetrahydro-2H-pyran-2-yloxy)propyl)-2,2,2-trifluoroacetamide was used. MS (EI) calc'd for $C_{27}H_{33}ClF_3N_4O_4$ $[M+H]^+$ 569, found 569.

Step 8: 2-(3-(5-Chloro-1-ethyl-1H-pyrazolo[3,4-c]pyridin-7-yl)propoxy)-1-phenyl-3-((tetrahydro-2H-pyran-2-yl)oxy)propan-1-amine To a solution of N-(2-(3-(5-chloro-1-ethyl-1H-pyrazolo[3,4-c]pyridin-7-yl)propoxy)-1-phenyl-3-((tetrahydro-2H-pyran-2-yl)oxy)propyl)-2,2,2-trifluoroacetamide (100 mg, 0.17 mmol) in MeOH (6 mL) was added a solution of K₂CO₃ (121 mg, 0.88 mmol) in water (2 mL). After stirring for 5 h at 65° C., the mixture was cooled to ambient temperature. Then water (30 mL) was added and the mixture was extracted with EtOAc, washed with brine, dried (Na₂SO₄) and filtered. The filtrate was concentrated under reduced pressure to give 2-(3-(5-chloro-1-ethyl-1H-pyrazolo [3,4-c]pyridin-7-yl)propoxy)-1-phenyl-3-((tetrahydro-2H-pyran-2-yl)oxy)propan-1-amine. MS (EI) calc'd for $C_{25}H_{34}ClN_4O_3$ [M+H]⁺ 473, found 473.

Step 9: 1-(2-(3-(5-Chloro-1-ethyl-1H-pyrazolo[3,4-c]pyridin-7-yl)propoxy)-1-phenyl-3-(tetrahydro-2H-pyran-2-yloxy)propyl)urea This compound was synthesized by similar urea formation as described in example 1 at step 5 except 2-(3-(5-chloro-1-ethyl-1H-pyrazolo[3,4-c]pyridin-7-yl)propoxy)-1-phenyl-3-((tetrahydro-2H-pyran-2-yl)oxy)propan-1-amine was used: MS (EI) calc'd for $C_{26}H_{35}ClN_5O_4$ [M+H]⁺ 516, found 516.

Step 10: 1-Ethyl-10-(tetrahydro-2H-pyran-2-yloxy)-9-phenyl-1,6,9,10,13,14-hexahydro-12H-5,15-(azeno)pyrazolo[4,3-i][1,4,6]oxadiazacyclotetradecin-7(8H)-one This compound was synthesized by similar Buchwald coupling as described in example 1 at step 6 except 1-(2-(3-(5-chloro-1-ethyl-1H-pyrazolo[3,4-c]pyridin-7-yl)propoxy)-1-phenyl-3-(tetrahydro-2H-pyran-2-yloxy)propyl)urea was used. MS (EI) calc'd for $C_{26}H_{34}N_5O_4$ [M+H]⁺ 480, found 480.

Step 11: (9R,10R)-1-Ethyl-10-(hydroxymethyl)-9-phenyl-1,6,9,10,13,14-hexahydro-12H-5,15-(azeno) pyrazolo[4,3-i][1,4,6]oxadiazacyclotetradecin-7 (8H)-one and (9 S,10 S)-1-ethyl-10-(hydroxymethyl)-9-phenyl-1,6,9,10,13,14-hexahydro-12H-5,15-(azeno)pyrazolo[4,3-i][1,4,6] oxadiazacyclotetradecin-7(8H)-one To a solution of 1-ethyl-10-(tetrahydro-2H-pyran-2-yloxy)-9-phenyl-1,6,9,10,13,14-hexahydro-12H-5,15-(azeno)pyrazolo[4,3-i][1,4,6]oxadiazacyclotetradecin-7 (8H)-one (100 mg, 0.21 mmol) in MeOH (10 mL) and DCM (10 mL) was added p-toluenesulfonic acid (79 mg, 0.42 mmol). The mixture was degassed with nitrogen and stirred for 5 h at 25° C. Then water was added and the mixture was extracted with EtOAc, washed with saturated NaHCO₃, brine, dried (Na₂SO₄) and concentrated under reduced pressure. The residue was purified by Prep-TLC (DCM/MeOH=10:1). The two isomers were separated by a chiral HPLC.

(9R,10R) or (9S,10S)-1-ethyl-10-(hydroxymethyl)-9-phenyl-1,6,9,10,13,14-hexahydro-12H-5,15-(azeno)pyrazolo[4,3-i][1,4,6]oxadiazacyclotetradecin-7(8H)-one: MS (EI) calc'd for $C_{21}H_{26}N_5O_3$ [M+H]⁺ 396, found 396; ¹H NMR (400 MHz, DMSO-d₆) δ 11.75 (d, J=9.2 Hz, 1 H), 9.17 (s, 1 H), 8.11 (s, 1 H), 7.41-7.39 (m, 2 H), 7.34-7.31 (m, 2 H), 7.25 (t, J=7.2 Hz, 1 H), 7.03 (s, 1 H), 4.86-4.84 (m, 1 H), 4.83-4.75 (m, 1 H), 4.60 (q, J=7.2 Hz, 2 H), 4.00-3.96 (m, 1 H), 3.54-3.53 (m, 1 H), 3.52-3.47 (m, 3 H), 3.08-3.06 (m, 2 H), 2.39-2.36 (m, 1 H), 2.11-2.07 (m, 1 H), 1.43 (t, J=7.2 Hz, 3 H).

(9S,10S) or (9R,10R)-1-ethyl-10-(hydroxymethyl)-9-phenyl-1,6,9,10,13,14-hexahydro-12H-5,15-(azeno)pyrazolo[4,3-i][1,4,6]oxadiazacyclotetradecin-7(8 H)-one: MS (EI) calc'd for $C_{21}H_{26}N_5O_3$ [M+H]⁺ 396, found 396; ¹H NMR (400 MHz, DMSO-d₆) δ 11.74 (d, J=9.2 Hz, 1 H), 9.17 (s, 1 H), 8.11 (s, 1 H), 7.40-7.34 (m, 2 H), 7.32-7.30 (m, 2 H), 7.25 (t, J=7.2 Hz, 1 H), 7.04 (s, 1 H), 4.86-4.84 (m, 1 H), 4.75-4.72 (m, 1 H), 4.60 (q, J=7.2 Hz, 2 H), 4.00-3.98 (m, 1 H), 3.54-3.41 (m, 4 H), 3.08-3.06 (m, 2 H), 2.39-2.37 (m, 1 H), 2.08-2.07 (m, 1 H), 1.43 (t, J=6.8 Hz, 3 H).

Synthetic Method 8

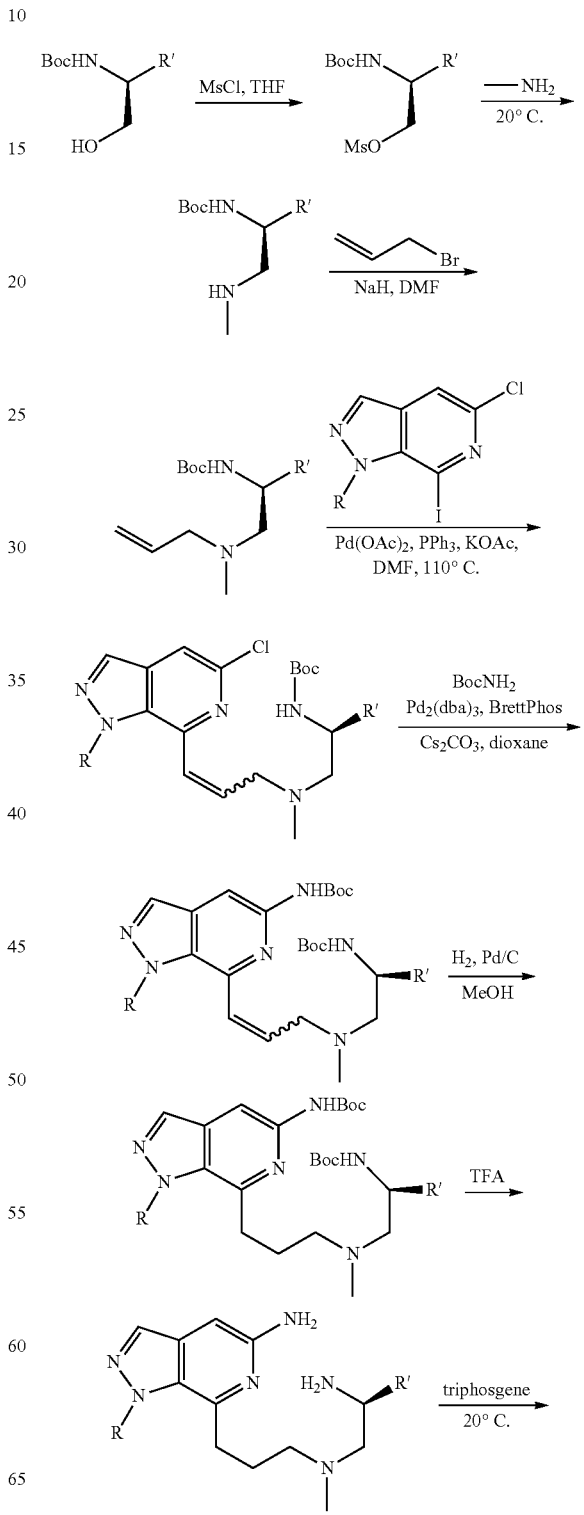

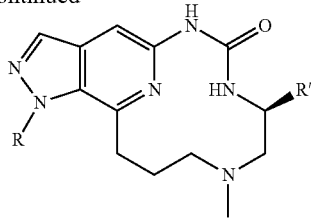

Example 15

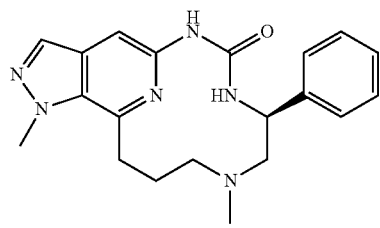

(9S)-1,11-Dimethyl-9-phenyl-1,6,9,10,11,12,13,14-octahydro-5,15-(azeno)pyrazolo[3,4-k][1,3,6]triazacyclotetradecin-7(8H)-one Step 1: (S)-2-((tert-Butoxycarbonyl)amino)-2-phenylethyl methanesulfonate A solution of methanesulfonyl chloride (4.93 mL, 63.2 mmol) in THF (10 mL) was added to a stirred, cooled (0° C.) mixture of (S)-tert-butyl (2-hydroxy-1-phenylethyl)carbamate (10.0 g, 42.1 mmol) and TEA (11.7 mL, 84 mmol) in THF (300 mL). The reaction mixture was stirred for 1 h at 0° C. and then quenched by saturated NaHCO$_3$, extracted with EtOAc, washed with brine, dried (Na$_2$SO$_4$) and filtered. The filtrate was concentrated under reduced pressure to give (S)-2-((tert-butoxycarbonyl)amino)-2-phenylethyl methanesulfonate. MS (EI) calc'd for $C_{14}H_{22}NO_5S$ [M+H]$^+$ 316, found 316.

Step 2: (S)-tert-Butyl (2-(methylamino)-1-phenylethyl)carbamate

To a solution of (S)-2-((tert-butoxycarbonyl)amino)-2-phenylethyl methanesulfonate (14.0 g, 44.4 mmol) in THF (100 mL) was added a solution of methanamine (13.8 g, 444 mmol) in MeOH (300 mL). After stirring for 16 h at 25° C., the reaction mixture was quenched by water, extracted with EtOAc, washed with brine, dried (Na$_2$SO$_4$), filtered and concentrated under reduced pressure. The residue was purified by chromatography on SiO$_2$, eluted with DCM/MeOH (40:1) to give (S)-tert-butyl (2-(methylamino)-1-phenylethyl)carbamate. MS (EI) calc'd for $C_{14}H_{23}N_2O_2$ [M+H]$^+$ 251, found 251.

Step 3: (S)-tert-Butyl (2-(allyl(methyl)amino)-1-phenylethyl)carbamate

This compound was synthesized by similar alkylation procedure as described in example 1 at step 1 except (S)-tert-butyl (2-(methylamino)-1-phenylethyl)carbamate was used. MS (EI) calc'd for $C_{17}H_{27}N_2O_2$ [M+H]$^+$ 291, found 291.

Step 4: (S)-tert-Butyl 2-((3-(5-chloro-1-ethyl-1H-pyrazolo[3,4-c]pyridin-7-yl)allyl)(methyl)amino)-1-phenylethylcarbamate This compound was synthesized by similar palladium coupling as described in example 1 at step 2 except (S)-tert-butyl (2-(allyl(methyl)amino)-1-phenylethyl)carbamate was used. MS (EI) calc'd for $C_{24}H_{31}ClN_5O_2$ [M+H]$^+$ 456, found 456.

Step 5: (S)-tert-Butyl (2-((3-(5-tert-butoxycarbonylamino-1-methyl-1H-pyrazolo[3,4-c]pyridin-7-yl)allyl)(methyl)amino)-1-phenylethyl)carbamate To a mixture of (S)-tert-butyl (2-((3-(5-chloro-1-methyl-1H-pyrazolo[3,4-c]pyridin-7-yl)allyl)(methyl)amino)-1-phenylethyl)carbamate (500 mg, 1.09 mmol) in dioxane (10 mL) were added tert-butyl carbamate (193 mg, 1.65 mmol), Brettphos (29.4 mg, 0.06 mmol), Cs$_2$CO$_3$ (715 mg, 2.19 mmol) and Pd$_2$(dba)$_3$·CHCl$_3$ (50.2 mg, 0.055 mmol). The resulting mixture was stirred for 3 h at 120° C. in an oil bath. The reaction mixture was cooled down and concentrated under vacuum. The residue was purified by chromatography on SiO$_2$, eluted with petroleum ether/EtOAc (2:1) to give (S)-tert-butyl (2-((3-(5-tert-butoxycarbonylamino-1-methyl-1H-pyrazolo[3,4-c]pyridin-7-yl)allyl)(methyl)amino)-1-phenylethyl)carbamate. MS (EI) calc'd for $C_{29}H_{41}N_6O_4$ [M+1-1]$^+$537, found 537.

Step 6: (S)-tert-Butyl (2-((3-(5-tert-butoxy carbonyl amino-1-methyl-1H-pyrazolo [3,4-c]pyridin-7-yl)propyl)(methyl)amino)-1-phenylethyl)carbamate This compound was synthesized by similar hydrogenation procedure as described in example 1 at step 3 except (S)-tert-butyl (2-((3-(5-tert-butoxycarbonylamino-1-methyl-1H-pyrazolo[3,4-c]pyridin-7-yl)allyl)(methyl) amino)-1-phenylethyl)carbamate was used, and methanol was used as a solvent. MS (EI) calc'd for $C_{29}H_{43}N_6O_4$ [M+H]$^+$ 539, found 539.

Step 7: (S)-N1-(3-(5-1-methyl-1H-pyrazolo[3,4-c] pyridin-7-yl)propyl)-N1-methyl-2-phenylethane-1,2-diamine This compound was synthesized by similar TFA deprotection as described in example 1 at step 4 except (S)-tert-butyl (2-((3-(5-tert-butoxycarbonylamino-1-methyl-1H-pyrazolo[3,4-c]pyridin-7-yl)propyl)(methyl)amino)-1-phenylethyl)carbamate was used. MS (EI) calc'd for $C_{19}H_{27}N_6$ [M+H]$^+$ 339, found 339.

Step 8: (9S)-1,11-Dimethyl-9-phenyl-1,6,9,10,11,12,13,14-octahydro-5,15-(azeno)pyrazolo[3,4-k][1,3,6]triazacyclotetradecin-7(8H)-one To a solution of (S)-N1-(3-(5-amino-1-methyl-1H-pyrazolo[3,4-c]pyridin-7-yl)propyl)-N1-methyl-2-phenylethane-1,2-diamine (75 mg, 0.22 mmol) in DCM (6 mL) was added triphosgene (21.1 mg, 0.071 mmol) and TEA (0.099 mL, 0.71 mmol). After stirring for 2 h at 25° C., the reaction mixture was quenched with saturated NaHCO$_3$, extracted with DCM and concentrated under reduced pressure. The crude product was purified by Prep-TLC (DCM/MeOH=20:1) to give (9S)-1,11-dimethyl-9-phenyl-1,6,9,10,11,12,13,14-octahydro-5,15-(azeno)pyrazolo[3,4-k][1,3,6]triazacyclotetradecin-7(8H)-one. MS (EI) calc'd for $C_{20}H_{25}N_6O$ [M+H]$^+$ 365, found 365. $^1$H NMR (400 MHz, CDCl$_3$) δ 11.71 (d, J=7.2 Hz, 1 H), 7.89 (s, 1 H), 7.49 (d, J=7.2 Hz, 2 H), 7.42 (s, 1 H), 7.37 (t, J=7.6 Hz, 2 H), 7.29-7.24 (m, 1 H), 6.79 (s, 1 H), 4.97-4.94 (m, 1 H), 4.33 (s, 3 H), 3.52-3.35 (m, 2 H), 2.88 (d, J=3.6 Hz, 2 H), 2.73-2.71 (m, 1 H), 2.59-2.54 (m, 1 H), 2.32-2.27 (m, 1 H), 2.05 (s, 3 H), 1.93-1.91 (m, 1 H).

Synthetic Method 9

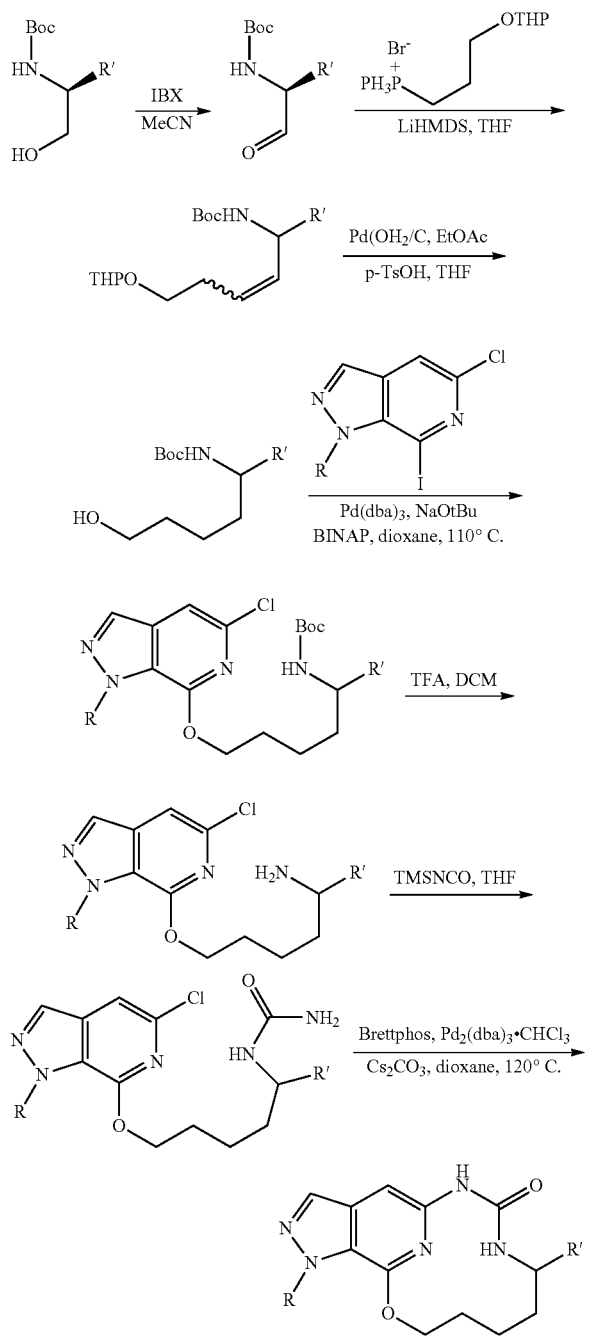

Example 16

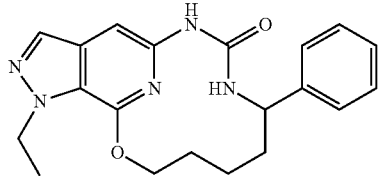 [SMILES: CCn1ncc2cc3nc(c21)OCCCCC(c1ccccc1)NC(=O)N3]

1-Ethyl-9-phenyl-1,6,8,9,10,11,12,13-octahydro-7H-5,15-(azeno)pyrazolo [3,4-c][1,7,9]oxadiazacyclotetradecin-7-one

Step 1: (S)-tert-Butyl (2-oxo-1-phenylethyl)carbamate

To a solution of (S)-tert-butyl (2-hydroxy-1-phenylethyl)carbamate (20.0 g, 84 mmol) in MeCN (500 mL) was added 2-iodylbenzoic acid (47.2 g, 169 mmol) under nitrogen. The resulting solution was stirred for 2 h at 80° C. and then cooled to ambient temperature and filtered. The filtrate was concentrated under vacuum to give (S)-tert-butyl (2-oxo-1-phenylethyl)carbamate, which was used directly for the next step without further purification.

Step 2: tert-Butyl 1-phenyl-5-(tetrahydro-2H-pyran-2-yloxy)pent-2-enylcarbamate Under a nitrogen atmosphere, lithium bis(trimethylsilyl)amide (46.8 mL, 46.8 mmol) was added dropwise to a solution of bromotriphenyl(3-((tetrahydro-2H-pyran-2-yl)oxy)propyl)phosphorane (20.6 g, 42.5 mmol, synthesized from 3-bromopropan-1-ol according to J. Org. Chem. 2013, 78, 7701.) in THF (5 mL) at −78° C. The resulting mixture was warmed to −10° C. and stirred for 30 minutes. Next, a solution of (S)-tert-butyl (2-oxo-1-phenylethyl)carbamate (5 g, 21.3 mmol) in THF (5 mL) was added dropwise at −30° C. over 15 min. The resulting mixture was warmed to 20° C. and stirred for 2 h. The reaction mixture was quenched by water and extracted with EtOAc, washed with brine, dried (Na$_2$SO$_4$), filtered and concentrated under reduced pressure. The residue was purified by chromatography on SiO$_2$, eluting with petroleum ether/EtOAc (10:1) to give tert-butyl 1-phenyl-5-(tetrahydro-2H-pyran-2-yloxy)pent-2-enylcarbamate. MS (EI) calc'd for $C_{21}H_{32}NO_4$ [M+H]$^+$ 362, found 362.

Step 3: tert-Butyl (5-hydroxy-1-phenylpentyl)carbamate

To a solution of tert-butyl 1-phenyl-5-(tetrahydro-2H-pyran-2-yloxy)pent-2-enylcarbamate (3.0 g, 8.30 mmol) in MeOH (30 mL) was added Pd/C (0.1 g, 0.83 mmol) (dry, 10%). The resulting mixture was purged in 2~4 atm. of hydrogen and stirred for 10 h at 25° C. under an atmosphere of hydrogen (2~4 atm.). Then the reaction mixture was filtered and concentrated under reduced pressure. The residue was dissolved in MeOH (50 mL) and treated with 4-methylbenzenesulfonic acid (1.1 g, 6.60 mmol). The resulting solution was stirred for 1 h at 25° C., then quenched by saturated NaHCO$_3$, extracted with EtOAc, washed with brine, dried (Na$_2$SO$_4$), filtered and concentrated under reduced pressure. The residue was purified by chromatography on SiO$_2$, eluted with petroleum ether/EtOAc (2:1) to give tert-butyl (5-hydroxy-1-phenylpentyl)carbamate. MS (EI) calc'd for C$_{16}$H$_{26}$NO$_3$ [M+H]$^+$ 280, found 280.

Step 4: tert-Butyl 5-(5-chloro-1-ethyl-1H-pyrazolo[3,4-c]pyridin-7-yloxy)-1-phenylpentylcarbamate To a solution of 5-chloro-1-ethyl-7-iodo-1H-pyrazolo[3,4-c]pyridine (500 mg, 1.63 mmol) and tert-butyl (5-hydroxy-1-phenylpentyl)carbamate (454 mg, 1.63 mmol) in 1,4-dioxane (15 mL) were added Pd$_2$(dba)$_3$·CHCl$_3$ (84 mg, 0.081 mmol), BINAP (50.6 mg, 0.081 mmol) and sodium tert-butoxide (316 mg, 3.25 mmol). The resulting mixture was stirred for 10 h at 110° C. and then filtered. The filtrate was concentrated under vacuum. The residue was purified by chromatography on SiO$_2$, eluted with petroleum ether/EtOAc (3:1) to give tert-butyl 5-(5-chloro-1-ethyl-1H-pyrazolo[3,4-c]pyridin-7-yloxy)-1-phenylpentylcarbamate. MS (EI) calc'd for C$_{24}$H$_{32}$ClN$_4$O$_3$ [M+H]$^+$ 459, found 459.

Step 5: 5-(5-Chloro-1-ethyl-1H-pyrazolo[3,4-c]pyridin-7-yloxy)-1-phenylpentan-1-amine This compound was synthesized by similar TFA deprotection as described in example 1 at step 4 except 5-(5-chloro-1-ethyl-1H-pyrazolo[3,4-c]pyridin-7-yloxy)-1-phenylpentylcarbamate was used. MS (EI) calc'd for C$_{19}$H$_{24}$ClN$_4$O [M+H]$^+$ 359, found 359.

Step 6: 1-(5-(5-Chloro-1-ethyl-1H-pyrazolo[3,4-c]pyridin-7-yloxy)-1-phenylpentyl)urea This compound was synthesized by similar urea formation as described in example 1 at step 5 except 5-(5-chloro-1-ethyl-1H-pyrazolo[3,4-c]pyridin-7-yloxy)-1-phenylpentan-1-amine was used. MS (EI) calc'd for C$_{20}$H$_{25}$ClN$_5$O$_2$ [M+H]$^+$ 402, found 402.

Step 7: 1-Ethyl-9-phenyl-1,6,8,9,10,11,12,13-octahydro-7H-5,15-(azeno)pyrazolo[3,4-c][1,7,9]oxadiazacyclotetradecin-7-one This compound was synthesized by the similar Buchwald coupling as described in example 1 at step 6 except 1-(5-(5-Chloro-1-ethyl-1H-pyrazolo[3,4-c]pyridin-7-yloxy)-1-phenylpentyl)urea was used: MS (EI) calc'd for C$_{20}$H$_{24}$N$_5$O$_2$ [M+H]$^+$ 366, found 366; $^1$H NMR (400 MHz, DMSO-d$_6$) δ 10.69 (d, J=5.6 Hz, 1 H), 9.19 (s, 1 H), 8.04 (s, 1 H), 7.35-7.28 (m, 4 H), 7.22 (t, J=6.8 Hz, 1 H), 6.69 (s, 1 H), 4.89 (br s, 1 H), 4.79-4.75 (m, 1 H), 4.59-4.52 (m, 3 H), 2.16-2.10 (m, 2 H), 2.00-1.96 (m, 2 H), 1.48-1.47 (m, 1 H), 1.43 (t, J=6.8 Hz, 3 H), 1.26 (br s, 1 H).δ

Example 17

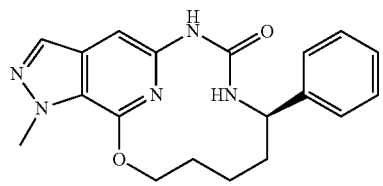 [SMILES: Cn1ncc2cc3nc(c21)OCCCC[C@H](c1ccccc1)NC(=O)N3]

(9R)-1-Methyl-9-phenyl-1,6,8,9,10,11,12,13-octahydro-7H-5,15-(azeno)pyrazolo[3,4-c][1,7,9]oxadiazacyclotetradecin-7-one This compound was synthesized by the same method as described in example 16 except 5-chloro-1-methyl-7-iodo-1H-pyrazolo[3,4-c]pyridine and (R)-tert-butyl (5-hydroxy-1-phenylpentyl)carbamate were used: MS (EI) calc'd for C$_{19}$H$_{22}$N$_5$O$_2$ [M+H]$^+$ 352, found 352; $^1$H NMR (400 MHz, DMSO-d$_6$) δ 10.69 (d, J=5.6 Hz, 1 H), 9.19 (s, 1 H), 8.01 (s, 1 H), 7.35-7.28 (m, 4 H), 7.22 (t, J=6.8 Hz, 1 H), 6.67 (s, 1 H), 4.88 (br s, 1 H), 4.79-4.73 (m, 1 H), 4.59-4.51 (m, 1 H), 4.19 (s, 3 H), 2.16-2.10 (m, 2 H), 2.00-1.96 (m, 2 H), 1.51-1.48 (m, 1 H), 1.26-1.24 (m, 1 H).

Synthetic Method 10

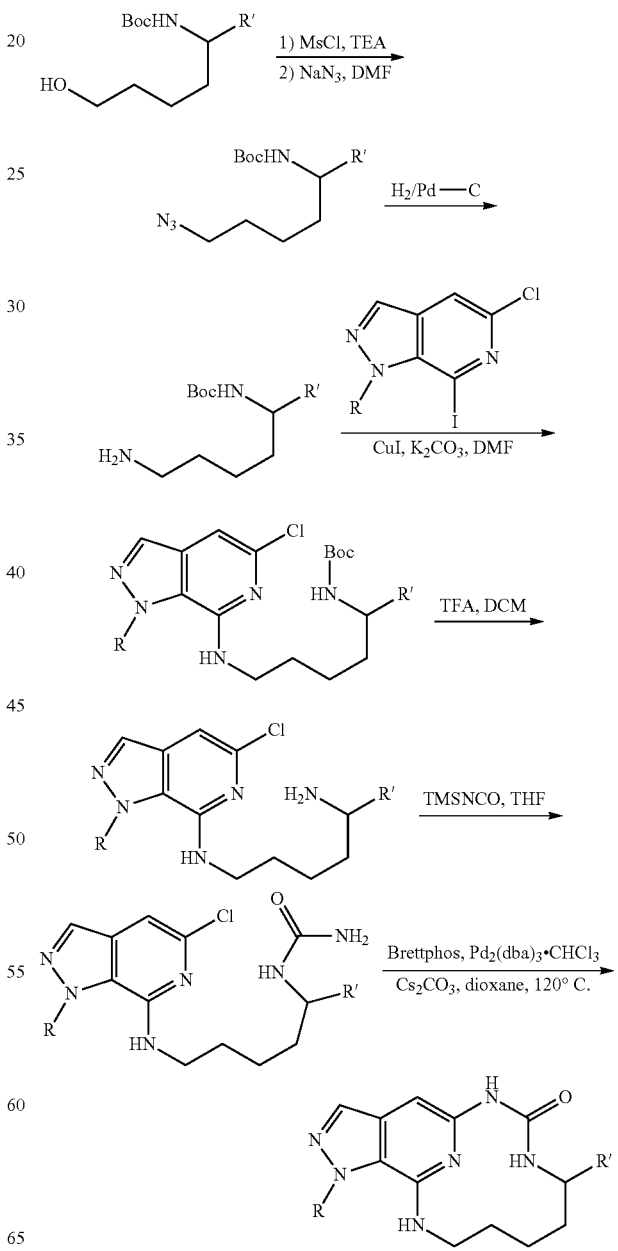

Example 18

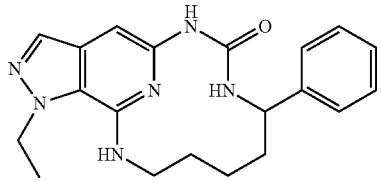 [SMILES: CCn1ncc2cc3nc(c21)NCCCCC(c1ccccc1)NC(=O)N3]

1-Ethyl-9-phenyl-1,6,9,10,11,12,13,14-octahydro-5,15-(azeno)pyrazolo[4,3-f][1,3,9]triazacyclotetradecin-7(8H)-one

Step 1: tert-Butyl (5-azido-1-phenylpentyl)carbamate

To a solution of tert-butyl (5-hydroxy-1-phenylpentyl)carbamate (1.5 g, 5.37 mmol) and TEA (0.82 g, 8.05 mmol) in THF (25 mL) was added methanesulfonyl chloride (0.74 g, 6.44 mmol) at 0° C. in 5 min. The resulting solution was stirred at 25° C. for 2 h and then quenched by saturated NaHCO$_3$. The mixture was extracted with EtOAc, washed with brine, dried (Na$_2$SO$_4$), and filtered. The filtrate was concentrated under reduced pressure to give 1.6 g of 5-((tert-butoxycarbonyl)amino)-5-phenylpentyl methanesulfonate, which was dissolved in N,N-dimethylacetamide (15 mL). Then sodium azide (0.55 g, 8.39 mmol) was added and the resulting solution was stirred at 25° C. for 2 h. The reaction mixture was quenched by saturated NH$_4$Cl, extracted with EtOAc, washed with brine, dried (Na$_2$SO$_4$) and filtered. The filtrate was concentrated under reduced pressure to give tert-butyl (5-azido-1-phenylpentyl)carbamate, which was used directly for the next step without further purification. MS (EI) calc'd for C$_{16}$H$_{25}$N$_4$O$_2$ [M+H]$^+$ 305, found 305.

Step 2: tert-Butyl (5-amino-1-phenylpentyl)carbamate

A mixture of tert-butyl (5-azido-1-phenylpentyl)carbamate (500 mg, 1.64 mmol) and Pd/C (195 mg, 1.64 mmol) (10%, dry) in MeOH (20 mL) was purged in 2~4 atm. of hydrogen and was stirred for 2 h at 25° C. under an atmosphere of hydrogen (2~4 atm.). Upon filtration and concentration under reduced pressure, the residue was purified by chromatography on SiO$_2$, eluted with DCM/MeOH (10/1) to give tert-butyl (5-amino-1-phenylpentyl)carbamate: MS (EI) calc'd for C$_{16}$H$_{27}$N$_2$O$_2$ [M+H]$^+$ 279, found 279.

Step 3: tert-Butyl 5-(5-chloro-1-ethyl-1H-pyrazolo[3,4-c]pyridin-7-ylamino)-1-phenylpentylcarbamate To a solution of tert-butyl (5-amino-1-phenylpentyl)carbamate (500 mg, 1.80 mmol) in N,N-dimethylformamide (20 mL) under nitrogen were added 5-chloro-1-ethyl-7-iodo-1H-pyrazolo[3,4-c]pyridine (552 mg, 1.80 mmol), 2-acetylcyclohexan-1-one (252 mg, 1.80 mmol), CuI (342 mg, 1.80 mmol) and Cs$_2$CO$_3$ (585 mg, 1.80 mmol). The resulting mixture was stirred for 3 h at 80° C. The reaction mixture was quenched by saturated NH$_4$Cl, extracted with EtOAc, washed with brine, dried (Na$_2$SO$_4$), filtered and concentrated under reduced pressure. The residue was purified by chromatography on SiO$_2$, eluted with petroleum ether/EtOAc (10:1) to afford tert-butyl 5-(5-chloro-1-ethyl-1H-pyrazolo[3,4-c]pyridin-7-ylamino)-1-phenylpentylcarbamate. MS (EI) calc'd for C$_{24}$H$_{33}$ClN$_5$O$_2$ [M+H]$^+$ 458, found 458.

Step 4: N1-(5-Chloro-1-ethyl-1H-pyrazolo[3,4-c]pyridin-7-yl)-5-phenylpentane-1,5-diamine This compound was synthesized by similar TFA deprotection as described in example 1 at step 4 except tert-butyl 5-(5-chloro-1-ethyl-1H-pyrazolo[3,4-c]pyridin-7-ylamino)-1-phenylpentylcarbamate was used. MS (EI) calc'd for C$_{19}$H$_{24}$ClN$_5$O [M+H]$^+$ 358, found 358.

Step 5: 1-(5-(5-Chloro-1-ethyl-1H-pyrazolo[3,4-c]pyridin-7-ylamino)-1-phenylpentyl)urea This compound was synthesized by similar urea formation as described in example 1 at step 5 except 1N-(5-chloro-1-ethyl-1H-pyrazolo[3,4-c]pyridin-7-yl)-5-phenylpentane-1,5-diamine was used. MS (EI) calc'd for C$_{20}$H$_{25}$ClN$_6$O [M+H]$^+$ 401, found 401.

Step 6: 1-Ethyl-9-phenyl-1,6,9,10,11,12,13,14-octahydro-5,15-(azeno)pyrazolo[4,3-f][1,3,9]triazacyclotetradecin-7(8H)-one This compound was synthesized by similar Buchwald coupling as described in example 1 at step 6 except 1-(5-(5-chloro-1-ethyl-1H-pyrazolo[3,4-c]pyridin-7-ylamino)-1-phenylpentyl)urea was used: MS (EI) calc'd for C$_{20}$H$_{25}$N$_6$O [M+H]$^+$ 365, found 365; $^1$H NMR (400 MHz, DMSO-d$_6$) δ 11.56 (d, J=5.6 Hz, 1 H), 8.91 (s, 1 H), 7.85 (s, 1 H), 7.32 (t, J=7.2 Hz, 2 H), 7.24 (t, J=7.2 Hz, 2 H), 7.20-7.15 (m, 2 H), 6.28 (s, 1 H), 4.90-4.89 (m, 1 H), 4.59 (q, J=7.2 Hz, 2 H), 3.64-3.59 (m, 1 H), 3.31-3.29 (m, 1 H), 2.18-2.12 (m, 1 H), 2.03-1.88 (m, 2 H), 1.72-1.68 (m, 1 H), 1.47-1.41 (m, 1 H), 1.34 (t, J=7.2 Hz, 3 H), 1.18-1.13 (m, 1 H).

Example 19

(9R)-1-Methyl-9-phenyl-1,6,9,10,11,12,13,14-octahydro-5,15-(azeno)pyrazolo[4,3-f][1,3,9]triazacyclotetradecin-7(8 H)-one This compound was synthesized by the same method as described in example 18 except 5-chloro-1-methyl-7-iodo-1H-pyrazolo[3,4-c]pyridine and (R)-tert-Butyl (5-amino-1-phenylpentyl)carbamate were used at step 3: MS (EI) calc'd for C$_{19}$H$_{22}$N$_6$O [M+H]$^+$ 351, found 351; $^1$H NMR (400 MHz, CD$_3$OD) δ 12.13 (d, J=5.6 Hz, 1 H), 7.75 (s, 1 H), 7.34-7.28 (m, 4 H), 7.21 (t, J=6.8 Hz, 1 H), 6.32 (s, 1 H), 5.03-5.02 (m, 1 H), 4.27 (s, 3 H), 3.76-3.71 (m, 1 H), 3.38-3.34 (m, 1 H), 2.30-2.23 (m, 1 H), 2.12-1.03 (m, 2 H), 1.84-1.81 (m, 1 H), 1.54-1.50 (m, 1 H), 1.35-1.30 (m, 1 H).

Example 20

1,14-Dimethyl-9-phenyl-1,6,9,10,11,12,13,14-octahydro-5,15-(azeno)pyrazolo[4,3-f][1,3,9]triazacyclotetradecin-7(8H)-one Step 1: (R)-5-((tert-butoxycarbonyl)amino)-5-phenylpentyl 4-methylbenzenesulfonate Into a solution of (R)-tert-butyl (5-hydroxy-1-phenylpentyl)carbamate (950 mg, 3.40 mmol), TEA (516 mg, 5.10 mmol) and DMAP (42 mg, 0.34 mmol) in DCM (10 ml) was added 4-methylbenzenesulfonyl chloride (972 mg, 5.10 mmol) dropwise at 0° C. in 5 min. After stirring for 16 h at 25° C., the reaction mixture was diluted with DCM (100 mL), washed with cooled saturated sodium hydrogen carbonate (10 mL), dried (Na$_2$SO$_4$), and filtered. The filtrate was evaporated under reduced pressure to give (R)-5-((tert-butoxycarbonyl)amino)-5-phenylpentyl 4-methylbenzenesulfonate, which was used directly for the next step without further purification. MS (EI) calc'd for C$_{23}$H$_{32}$NO$_5$S [M+H]$^+$ 434; found 434.

Step 2: tert-Butyl 5-(methylamino)-1-phenylpentylcarbamate

To a solution of (R)-5-((tert-butoxycarbonyl)amino)-5-phenylpentyl 4-methylbenzenesulfonate (900 mg, 2.07 mmol) in ethanol (10 ml) in a 20-ml sealed tube was added methylamine (1.29 g, 30% in methanol, 41.5 mmol) and the resulting mixture was stirred for 2 h at 60° C. The reaction mixture was cooled down to ambient temperature, and the solvent was evaporated under reduced pressure. The residue was purified by chromatography on SiO$_2$, eluted with dichloromethane/methanol (20:1) with 0.5% TEA to give (R)-tert-butyl (5-(methylamino)-1-phenylpentyl)carbamate; MS (EI) calc'd for C$_{17}$H$_{29}$N$_2$O$_2$ [M+H]$^+$ 293, found 293.

Step 3: 1,14-Dimethyl-9-phenyl-1,6,9,10,11,12,13,14-octahydro-5,15-(azeno)pyrazolo[4,3-f][1,3,9]triazacyclotetradecin-7(8H)-one This compound was synthesized by the same method as described in example 18 except 5-chloro-1-methyl-7-iodo-1H-pyrazolo[3,4-c]pyridine and tert-butyl 5-(methylamino)-1-phenylpentylcarbamate were used at step 4: MS (EI) calc'd for C$_{20}$H$_{25}$N$_6$O [M+H]$^+$ 365, found 365; $^1$H NMR (400 MHz, CDCl$_3$) δ 11.66 (br s, 1 H), 7.91 (s, 1 H), 7.67 (br s, 1 H), 7.37-7.29 (m, 4 H), 7.27 (t, J=8.4 Hz, 1 H), 6.49 (s, 1 H), 5.08-5.07 (m, 1 H), 4.24 (s, 3 H), 3.71-3.69 (m, 1 H), 3.29-3.26 (m, 1 H), 3.19 (s, 3 H), 2.22-2.18 (m, 2 H), 2.09-2.03 (m, 2 H), 1.48-1.45 (m, 2 H).

Example 21

(9S)-1-Ethyl-9-phenyl-1,6,9,10,13,14-hexahydro-12H-5,15-(azeno)pyrazolo[4,3-i][1,4,6,12]oxatriazacyclotetradecin-7(8H)-one This compound was synthesized by the same method as described in example 18 except (S)-tert-butyl 2-(2-hydroxyethoxy)-1-phenylethylcarbamate was used at step 1: MS (EI) calc'd for C$_{19}$H$_{23}$N$_6$O$_2$ [M+H]$^+$ 367, found 367; $^1$H NMR (300 MHz, DMSO-d$_6$) δ 11.21 (d, J=6.3 Hz, 1 H), 8.89 (s, 1 H), 7.84 (s, 1 H), 7.37-7.29 (m, 4 H), 7.24-7.19 (m, 1 H), 6.97 (br s, 1 H), 6.32 (s, 1 H), 4.69-4.67 (m, 1 H), 4.57 (q, J=8.4 Hz, 2 H), 3.89-3.80 (m, 3 H), 3.73-3.66 (m, 3 H), 1.31 (t, J=6.9 Hz, 3 H).

Example 22

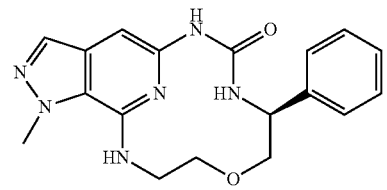

(9 S)-1-Methyl-9-phenyl-1,6,9,10,13,14-hexahydro-12H-5,15-(azeno)pyrazolo[4,3-i][1,4,6,12]oxatriazacyclotetradecin-7(8 H)-one This compound was synthesized by the same method as described in example 18 except (S)-tert-butyl 2-(2-hydroxyethoxy)-1-phenylethylcarbamate was used at step 1 and 5-chloro-1-methyl-7-iodo-1H-pyrazolo[3,4-c]pyridine was used at step 3: MS (EI) calc'd for C$_{18}$H$_{21}$N$_6$O$_2$ [M+H]$^+$ 353, found 353; $^1$H NMR (300 MHz, DMSO-d$_6$) δ 11.20 (d, J=6.0 Hz, 1 H), 8.87 (s, 1 H), 7.79 (s, 1 H), 7.37-7.31 (m, 4 H), 7.24-7.22 (m, 1 H), 7.04 (br s, 1 H), 6.30 (s, 1 H), 4.69-4.67 (m, 1 H), 4.22 (s, 3 H), 3.89-3.81 (m, 3 H), 3.72-3.62 (m, 3 H).

Synthetic Method 11

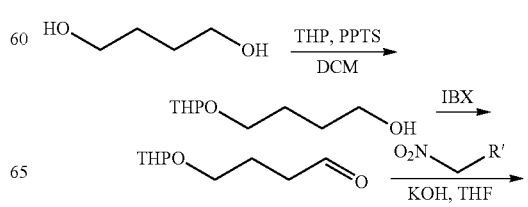

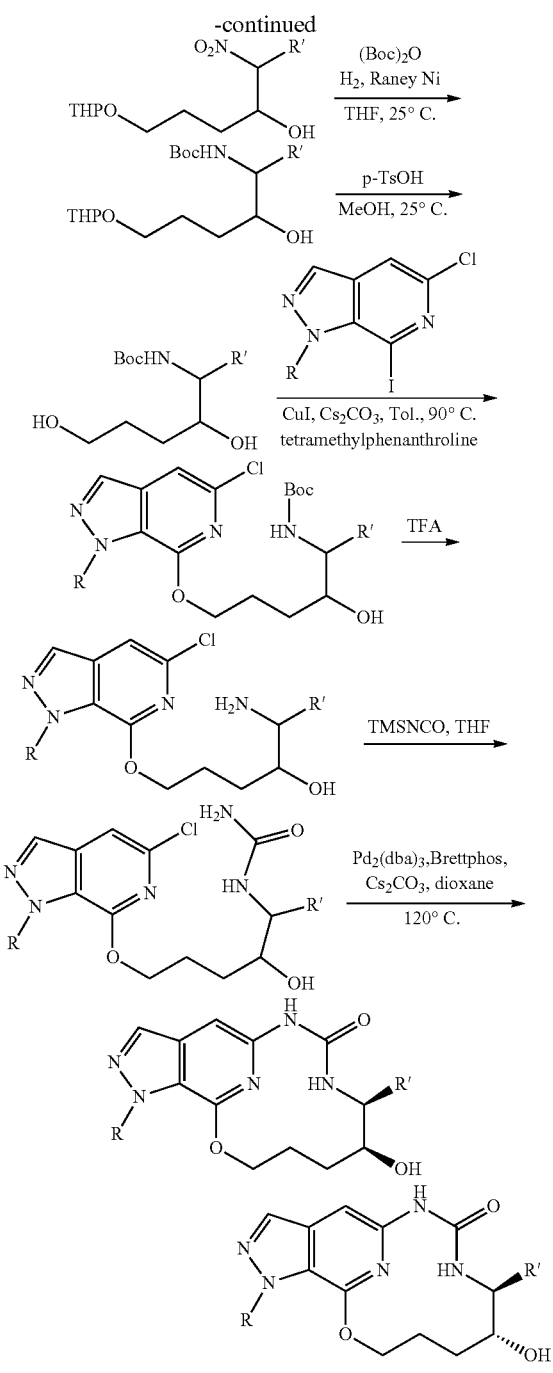

Example 23

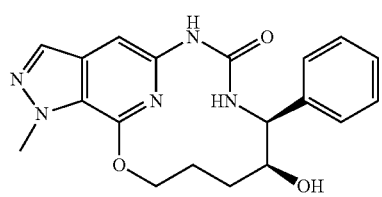 [SMILES: Cn1ncc2cc3nc(c21)OCCC[C@H](O)[C@H](c1ccccc1)NC(=O)N3]

(9S,10S)-10-Hydroxy-1-methyl-9-phenyl-1,6,8,9,10,11,12,13-octahydro-7H-5,15-(azeno)pyrazolo[3,4-c][1,7,9]oxadiazacyclotetradecin-7-one Example 24

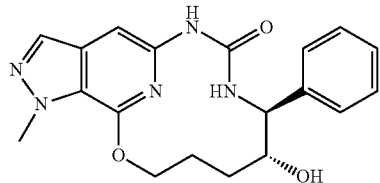 [SMILES: Cn1ncc2cc3nc(c21)OCCC[C@@H](O)[C@H](c1ccccc1)NC(=O)N3]

(9S,10R)-10-Hydroxy-1-methyl-9-phenyl-1,6,8,9,10,11,12,13-octahydro-7H-5,15-(azeno)pyrazolo[3,4-c][1,7,9]oxadiazacyclotetradecin-7-one Step 1: 4-(Tetrahydro-2H-pyran-2-yloxy)butan-1-ol Into a solution of butane-1,4-diol (30 g, 333 mmol) in THF (300 ml) at 0° C. was added 3,4-dihydro-2H-pyran (27.2 ml, 297 mmol) dropwise in 30 min, and then PPTS (3 g, 12 mmol) was added. The reaction mixture was stirred at 25° C. for 5 h, diluted with dichloromethane (200 mL), washed with saturated NaHCO₃ (500 mL), brine (3×500 mL), dried (Na₂SO₄), and filtered. After concentrated under reduced pressure, the residue was purified by chromatography on SiO₂, eluted with petroleum ether/EtOAc (10:1-5:1) to give 4-((tetrahydro-2H-pyran-2-yl)oxy)butan-1-ol (30 g); $^1$H NMR (300 MHz, DMSO-d₆) δ 4.53-4.52 (m, 2 H), 4.36 (t, J=5.1 Hz, 2 H), 3.73-3.69 (m, 2 H), 3.63-3.57 (m, 2 H), 1.71-1.41 (m, 10 H).

Step 2: 4-(Tetrahydro-2H-pyran-2-yloxy)butanal

Into a solution of 4-((tetrahydro-2H-pyran-2-yl)oxy)butan-1-ol (10.0 g, 57.4 mmol) in acetonitrile (300 mL) was added IBX (24 g, 86 mmol). The resulting mixture was stirred for 0.5 h at 80° C. The solid was filtered out. The filtrate was concentrated under vacuum to give 4-((tetrahydro-2H-pyran-2-yl)oxy)butanal. The crude 4-(tetrahydro-2H-pyran-2-yloxy)butanal was used directly for the next step without further purification.

Step 3: 1-Nitro-1-phenyl-5-(tetrahydro-2H-pyran-2-yloxy)pentan-2-ol

To a solution of (nitromethyl)benzene (14.0 g, 102 mmol) in THF (150 mL) was added a solution of KOH (0.2 g, 3.56 mmol) in MeOH (1 mL). The mixture was cooled to 0° C. and a solution of 4-((tetrahydro-2H-pyran-2-yl)oxy)butanal (9.0 g, 52.3 mmol) in THF (150 mL) was added dropwise with stirring. Then the resulting solution was stirred for 10 h at 25° C. and then concentrated under reduced pressure. The residue was diluted with EtOAc, washed with brine, dried (Na₂SO₄), filtered and concentrated. The crude product was purified by chromatography on SiO₂, eluted with petroleum ether/EtOAc (2:1) to give 1-nitro-1-phenyl-5-((tetrahydro-2H-pyran-2-yl)oxy)pentan-2-ol, which still contained some impurities and was used directly for the next step without further purification.

Step 4: tert-Butyl 2-hydroxy-1-phenyl-5-(tetrahydro-2H-pyran-2-yloxy)pentylcarbamate To a solution of 1-nitro-1-phenyl-5-((tetrahydro-2H-pyran-2-yl)oxy)pentan-2-ol (9.0 g, 29.1 mmol) in THF (200 mL) was added Raney-nickel (12 g, 0.20 mol) in portions. Then (Boc)$_2$O (12.77 g, 55.0 mmol) and TEA (4.13 mL, 29.6 mmol) were added. The resulting mixture was purged in 2~4 atm. of hydrogen and stirred for 16 h at 25° C. under an atmosphere of hydrogen (2~4 atm.). Upon filtration and concentration under reduced pressure, the residue was purified by chromatography on SiO$_2$, eluted with petroleum ether/EtOAc (5:1) to give tert-butyl (2-hydroxy-1-phenyl-5-((tetrahydro-2H-pyran-2-yl)oxy)pentyl)carbamate. MS (EI) calc'd for C$_{21}$H$_{34}$NO$_5$ [M+H]$^+$ 380, found 380.

Step 5: tert-Butyl 2,5-dihydroxy-1-phenylpentylcarbamate

Into a solution of tert-butyl (2-hydroxy-1-phenyl-5-((tetrahydro-2H-pyran-2-yl)oxy)pentyl)carbamate (2.0 g, 3.90 mmo) in MeOH (60 mL) was added pTsOH (1.2 g, 6.31 mmol) and then the reaction mixture was stirred at 25° C. for 20 min. The pH value of the solution was adjusted to 8 with saturated NaHCO$_3$. The resulting solution was diluted with ethyl acetate (150 mL), washed with brine (100 mL), dried (Na$_2$SO$_4$), and filtered. The filtrate was concentrated under reduced pressure to give tert-butyl (2,5-dihydroxy-1-phenylpentyl)carbamate. MS (EI) calc'd for C$_{16}$H$_{26}$NO$_4$ [M+H]$^+$ 296, found 296.

Step 6: tert-Butyl 5-(5-chloro-1-methyl-1H-pyrazolo[3,4-c]pyridin-7-yloxy)-2-hydroxy-1-phenylpentylcarbamate To a solution of tert-butyl (2,5-dihydroxy-1-phenylpentyl)carbamate (600 mg, 1.40 mmol) and 5-chloro-7-iodo-1-methyl-1H-pyrazolo[3,4-c]pyridine (400 mg, 1.23 mmol) in toluene (30 mL) were added cuprous iodide (18 mg, 0.095 mmol), 3,4,7,8-tetramethyl-1,10-phenanthroline (50 mg, 0.21 mmol) and Cs$_2$CO$_3$ (900 mg, 2.76 mmol). The reaction mixture was degassed by bubbling nitrogen for 3 min and then stirred at 90° C. for 6 h. The resulting mixture was diluted with water, extracted with ethyl acetate, washed with brine, dried (Na$_2$SO$_4$), filtered and concentrated under reduced pressure. The residue was purified by chromatography on SiO$_2$, eluted with petroleum ether/EtOAc (1:1) to give tert-butyl (5-((5-chloro-1-methyl-1H-pyrazolo[3,4-c]pyridin-7-yl)oxy)-2-hydroxy-1-phenylpentyl)carbamate. MS (EI) calc'd for C$_{23}$H$_{30}$ClN$_4$O$_4$ [M+H]$^+$ 461, found 461.

Step 7: 1-Amino-5-(5-chloro-1-methyl-1H-pyrazolo[3,4-c]pyridin-7-yloxy)-1-phenylpentan-2-ol This compound was synthesized by similar TFA deprotection as described in example 1 at step 4, except tert-butyl 5-(5-chloro-1-methyl-1H-pyrazolo[3,4-c]pyridin-7-yloxy)-2-hydroxy-1-phenylpentylcarbamate was used. MS (EI) calc'd for C$_{18}$H$_{22}$ClN$_4$O [M+H]$^+$ 361, found 361.

Step 8: 1-(5-(5-Chloro-1-methyl-1H-pyrazolo[3,4-c]pyridin-7-yloxy)-2-hydroxy-1-phenylpentyl)urea This compound was synthesized by similar urea formation as described in example 1 at step 5, except 1-amino-5-(5-chloro-1-methyl-1H-pyrazolo[3,4-c]pyridin-7-yloxy)-1-phenylpentan-2-ol was used. MS (EI) calc'd for C$_{19}$H$_{23}$ClN$_5$O$_3$ [M+H]$^+$ 404, found 404.

Step 9: (9S,10S)-10-Hydroxy-1-methyl-9-phenyl-1,6,8,9,10,11,12,13-octahydro-7H-5,15-(azeno)pyrazolo[3,4-c][1,7,9]oxadiazacyclotetradecin-7-one and (9S,10R)-10-Hydroxy-1-methyl-9-phenyl-1,6,8,9,10,11,12,13-octahydro-7H-5,15-(azeno)pyrazolo[3,4-c][1,7,9]oxadiazacyclotetradecin-7-one These compounds were synthesized by similar Buchwald coupling as described in example 1 at step 6, except 1-(5-(5-chloro-1-methyl-1H-pyrazolo[3,4-c]pyridin-7-yloxy)-2-hydroxy-1-phenylpentyl)urea was used. Two isomers were separated by Prep-HPLC.

(9S,10S) or (9S,10R)-10-Hydroxy-1-methyl-9-phenyl-1,6,8,9,10,11,12,13-octahydro-7H-5,15-(azeno)pyrazolo[3,4-c][1,7,9]oxadiazacyclotetradecin-7-one: MS (EI) calc'd for C$_{19}$H$_{22}$N$_5$O$_3$ [M+H]$^+$ 368, found 368; $^1$H NMR (400 MHz, DMSO-d$_6$) δ 10.24 (d, J=7.2 Hz, 1 H), 9.18 (s, 1 H), 8.02 (s, 1 H), 7.34-7.21 (m, 5 H), 6.68 (s, 1 H), 5.19-5.17 (m, 1 H), 4.93-4.88 (m, 2 H), 4.46-4.40 (m, 1 H), 4.27-4.25 (m, 1 H), 4.20 (s, 3 H), 2.18-2.15 (m, 1 H), 1.91-1.88 (m, 1 H), 1.34-1.31 (m, 2 H).

(9S,10R) or (9S,10S)-10-Hydroxy-1-methyl-9-phenyl-1,6,8,9,10,11,12,13-octahydro-7H-5,15-(azeno)pyrazolo[3,4-c][1,7,9]oxadiazacyclotetradecin-7-one: MS (EI) calc'd for C$_{19}$H$_{22}$N$_5$O$_3$ [M+H]$^+$ 368, found 368; $^1$H NMR (400 MHz, DMSO-d$_6$) δ 10.99 (d, J=5.6 Hz, 1 H), 9.20 (s, 1 H), 7.99 (s, 1 H), 7.34-7.20 (m, 5 H), 6.66 (s, 1 H), 5.34-5.33 (m, 1 H), 5.23 (br s, 1 H), 4.91 (t, J=5.2 Hz, 1 H), 4.42-4.40 (m, 1 H), 4.17 (s, 3 H), 4.10-4.08 (m, 1 H), 2.17-2.05 (m, 2 H), 1.63-1.59 (m, 1 H), 1.14-1.10 (m, 1 H).

Example 25

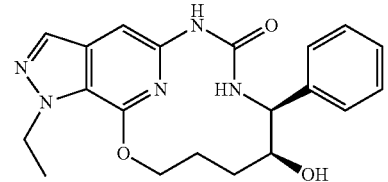 [SMILES: CCn1ncc2cc3nc(c21)OCCC[C@H](O)[C@H](c1ccccc1)NC(=O)N3]

(9S,10S)-1-Ethyl-10-hydroxy-9-phenyl-1,6,8,9,10,11,12,13-octahydro-7H-5,15-(azeno)pyrazolo[3,4-c][1,7,9]oxadiazacyclotetradecin-7-one This compound was synthesized by the same method as described in example 23 except 5-chloro-1-ethyl-7-iodo-1H-pyrazolo[3,4-c]pyridine was used at step 6: MS (EI) calc'd for C$_{20}$H$_{24}$N$_5$O$_3$ [M+H]$^+$ 382, found 382; $^1$H NMR (400 MHz, DMSO-d$_6$) δ 10.22 (d, J=7.2 Hz, 1 H), 9.18 (s, 1 H), 8.04 (s, 1 H), 7.34-7.21 (m, 5 H), 6.69 (s, 1 H), 5.17 (d, J=3.6 Hz, 1 H), 4.94-4.89 (m, 2 H), 4.56 (q, J=7.2 Hz, 2 H), 4.46-4.44 (m, 1 H), 4.27-4.25 (m, 1 H), 2.18-2.15 (m, 1 H), 1.91-1.90 (m, 1 H), 1.42 (t, J=7.2 Hz, 3 H), 1.31-1.28 (m, 2 H).

Example 26

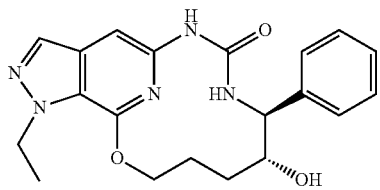 [SMILES: CCn1ncc2cc3nc(c21)OCCC[C@@H](O)[C@H](c1ccccc1)NC(=O)N3]

(9S,10R)-1-Ethyl-10-hydroxy-9-phenyl-1,6,8,9,10,11,12,13-octahydro-7H-5,15-(azeno)pyrazolo[3,4-c][1,7,9]oxadiazacyclotetradecin-7-one This compound was synthesized by the same method as described in example 23 except 5-chloro-1-ethyl-7-iodo-1H-pyrazolo[3,4-c]pyridine was used at step 6: MS (EI) calc'd for $C_{20}H_{24}N_5O_3$ [M+H]$^+$ 382, found 382; $^1$H NMR (400 MHz, DMSO-d$_6$) δ 11.02 (d, J=5.6 Hz, 1 H), 9.23 (s, 1 H), 8.04 (s, 1H), 7.36-7.24 (m, 5 H), 6.69 (s, 1 H), 5.37 (d, J=3.2 Hz, 1 H), 5.15 (br s, 1 H), 4.94 (t, J=5.2 Hz, 1 H), 4.55 (q, J=7.2 Hz, 2 H), 4.46-4.43 (m, 1 H), 4.14-4.12 (m, 1 H), 2.19-2.08 (m, 2 H), 1.63-1.59 (m, 1 H), 1.41 (t, J=7.2 Hz, 3 H), 1.17-1.15 (m, 1 H).

Synthetic Method 12

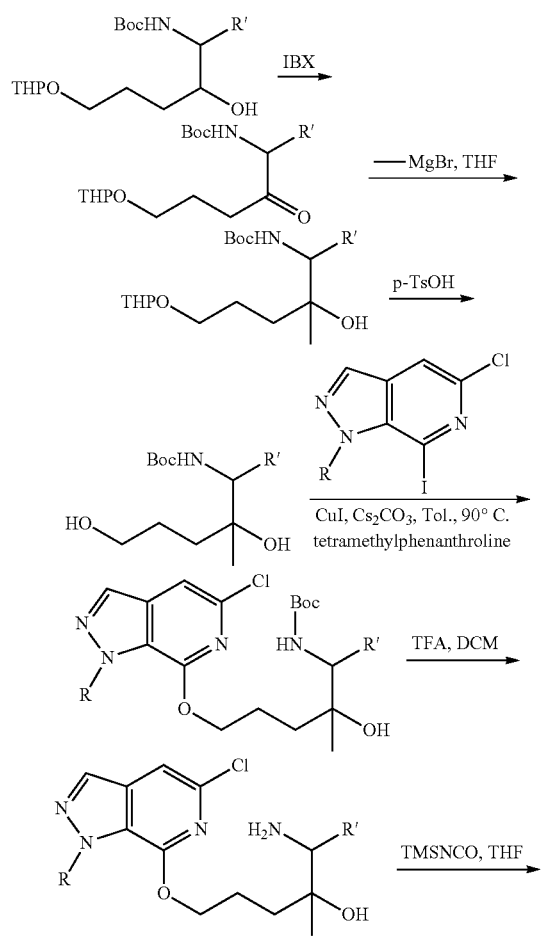

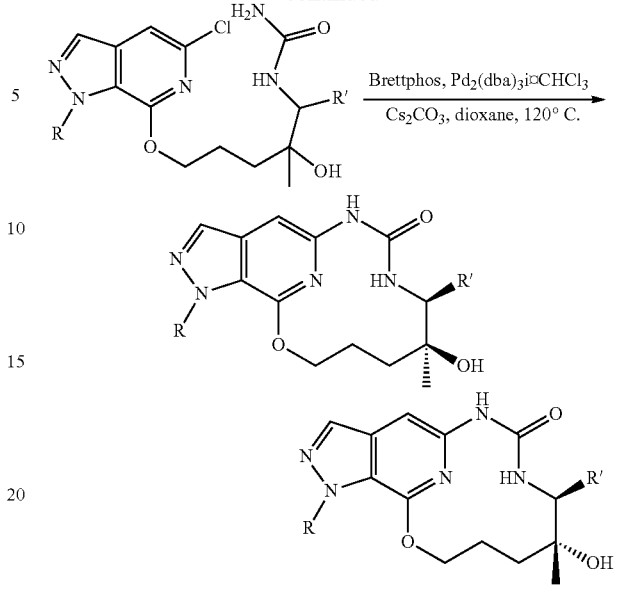

Example 27

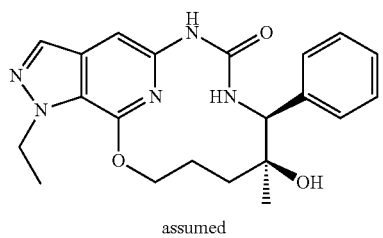 [SMILES: CCn1ncc2cc3nc(c21)OCCC[C@](C)(O)[C@H](c1ccccc1)NC(=O)N3]

assumed (9S,10S)-1-Ethyl-10-hydroxy-10-methyl-9-phenyl-1,6,8,9,10,11,12,13-octahydro-7H-5,15-(azeno)pyrazolo[3,4-c][1,7,9]oxadiazacyclotetradecin-7-one

Example 28

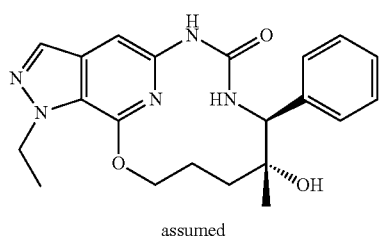 [SMILES: CCn1ncc2cc3nc(c21)OCCC[C@@](C)(O)[C@H](c1ccccc1)NC(=O)N3]

assumed (9S,10R)-1-Ethyl-10-hydroxy-10-methyl-9-phenyl-1,6,8,9,10,11,12,13-octahydro-7H-5,15-(azeno)pyrazolo[3,4-c][1,7,9]oxadiazacyclotetradecin-7-one Step 1: tert-Butyl 2-oxo-1-phenyl-5-(tetrahydro-2H-pyran-2-yloxy)pentylcarbamate Into a 250 ml round-bottom flask purged and maintained with an inert atmosphere of nitrogen, was placed a solution of tert-butyl (2-hydroxy-1-phenyl-5-((tetrahydro-2H-pyran-2-yl)oxy)pentyl)carbamate (3.0 g, 5.85 mmol) in acetonitrile (100 ml), and then IBX (2.8 g, 10.00 mmol) was added. The resulting mixture was stirred for 1 h at 80° C. The solid was filtered out. After concentrated under reduced pressure, the residue was purified by chromatography on SiO$_2$, eluted with petroleum ether/EtOAc (10:1-5:1) to give tert-butyl (2-oxo-1-phenyl-5-((tetrahydro-2H-pyran-2-yl)oxy)pentyl) carbamate; MS (EI) calc'd for C$_{21}$H$_{32}$NO$_6$ [M+H]$^+$ 378, found 378.

Step 2: tert-Butyl 2-hydroxy-2-methyl-1-phenyl-5-(tetrahydro-2H-pyran-2-yloxy)pentylcarbamate Into a solution of tert-butyl (2-oxo-1-phenyl-5-((tetrahydro-2H-pyran-2-yl)oxy)pentyl)carbamate (2.0 g, 3.92 mmol) in dry THF (25 mL) under nitrogen was added methyl magnesium bromide (10 mL, 3.0 M in diethyl ether, 30.0 mmol) dropwise at −20° C., and then the resulting mixture was allowed to warm to ambient temperature naturally. After stirring for 2 h at 25° C., the reaction mixture was quenched by saturated NH$_4$Cl (50 mL), extracted with ethyl acetate (150 mL), washed with brine (100 mL), dried over anhydrous sodium sulfate and filtered. The filtrate was concentrated under reduced pressure to give tert-butyl 2-hydroxy-2-methyl-1-phenyl-5-((tetrahydro-2H-pyran-2-yl)oxy)pentylcarbamate; MS (EI) calc'd for C$_{22}$H$_{36}$NO$_5$ [M+H]$^+$ 394, found 394.

Step 3: tert-Butyl 2,5-dihydroxy-2-methyl-1-phenylpentylcarbamate

To a stirred mixture of tert-butyl (2-hydroxy-2-methyl-1-phenyl-5-((tetrahydro-2H-pyran-2-yl)oxy)pentyl)carbamate (2.1 g, 2.77 mmol) in MeOH (30 mL) was added pTsOH (0.8 g, 4.21 mmol). The reaction mixture was stirred at 25° C. for 20 min. The pH value of the solution was adjusted to 8 with saturated NaHCO$_3$. The resulting mixture was diluted with ethyl acetate (150 mL), washed with brine (100 mL), dried (Na$_2$SO$_4$), and filtered. After concentrated under reduced pressure, the residue was purified by chromatography on SiO$_2$, eluted with dichloromethane/methanol (20:1-10:1) to give tert-butyl (2,5-dihydroxy-2-methyl-1-phenylpentyl)carbamate; MS (EI) calc'd for C$_{17}$H$_{28}$NO$_4$ [M+H]$^+$ 310, found 310.

Step 4: tert-Butyl 5-(5-chloro-1-ethyl-1H-pyrazolo[3,4-c]pyridin-7-yloxy)-2-hydroxy-2-methyl-1-phenylpentylcarbamate This compound was synthesized by the same method as described in example 23 at step 6 except tert-butyl 2,5-dihydroxy-2-methyl-1-phenylpentylcarbamate was used: MS (EI) calc'd for C$_{25}$H$_{34}$ClN$_4$O$_4$ [M+H]$^+$ 489, found 489.

Step 5: 1-Amino-5-(5-chloro-1-ethyl-1H-pyrazolo[3,4-c]pyridin-7-yloxy)-2-methyl-1-phenylpentan-2-ol This compound was synthesized by similar TFA deprotection as described in example 1 at step 4 except tert-butyl 5-(5-chloro-1-ethyl-1H-pyrazolo[3,4-c]pyridin-7-yloxy)-2-hydroxy-2-methyl-1-phenylpentylcarbamate was used: MS (EI) calc'd for C$_{20}$H$_{26}$ClN$_4$O$_2$ [M+H]$^+$ 389, found 389.

Step 6: 1-(5-(5-Chloro-1-ethyl-1H-pyrazolo[3,4-c]pyridin-7-yloxy)-2-hydroxy-2-methyl-1-phenylpentyl)urea This compound was synthesized by similar urea formation as described in example 1 at step 5 except 1-amino-5-(5-chloro-1-ethyl-1H-pyrazolo[3,4-c]pyridin-7-yloxy)-2-methyl-1-phenylpentan-2-ol was used: MS (EI) calc'd for C$_{21}$H$_{27}$ClN$_5$O$_3$ [M+H]$^+$ 432, found 432.

Step 7: (9S,10S)-1-Ethyl-10-hydroxy-10-methyl-9-phenyl-1,6,8,9,10,11,12,13-octahydro-7H-5,15-(azeno)pyrazolo[3,4-c][1,7,9]oxadiazacyclotetradecin-7-one and (9S,10R)-1-Ethyl-10-hydroxy-10-methyl-9-phenyl-1,6,8,9,10,11,12,13-octahydro-7H-5,15-(azeno)pyrazolo[3,4-c][1,7,9]oxadiazacyclotetradecin-7-one These compounds were synthesized by similar Buchwald coupling as described in example 1 at step 6 except 1-(5-(5-chloro-1-ethyl-1H-pyrazolo[3,4-c]pyridin-7-yloxy)-2-hydroxy-2-methyl-1-phenylpentyl)urea was used. The two isomers were separated by Prep-HPLC.

(9S,10S) or (9S,10R)-1-Ethyl-10-hydroxy-10-methyl-9-phenyl-1,6,8,9,10,11,12,13-octahydro-7H-5,15-(azeno)pyrazolo[3,4-c][1,7,9]oxadiazacyclotetradecin-7-one: MS (EI) calc'd for C$_{21}$H$_{26}$N$_5$O$_3$ [M+H]$^+$ 396, found 396; $^1$H NMR (400 MHz, DMSO-d$_6$) δ 10.57 (br s, 1 H), 9.16 (s, 1 H), 8.01 (s, 1 H), 7.39 (d, J=7.2 Hz, 2 H), 7.28 (t, J=7.2 Hz, 2 H), 7.21 (t, J=7.2 Hz, 1 H), 6.66 (s, 1 H), 4.73-4.71 (m, 1 H), 4.62-4.51 (m, 5 H), 2.13-2.11 (m, 2 H), 1.50-1.49 (m, 1 H), 1.39 (t, J=7.2 Hz, 3 H), 1.34-1.32 (m, 4 H).

(9S,10R) or (9S,10S)-1-Ethyl-10-hydroxy-10-methyl-9-phenyl-1,6,8,9,10, 11,12,13-octahydro-7H-5,15-(azeno)pyrazolo[3,4-c][1,7,9]oxadiazacyclotetradecin-7-one. MS (EI) calc'd for C$_{21}$H$_{26}$N$_5$O$_3$ [M+H]$^+$ 396, found 396; $^1$H NMR (400 MHz, DMSO-d$_6$) δ 11.11 (br s, 1 H), 9.09 (s, 1 H), 8.03 (s, 1 H), 7.32-7.28 (m, 4 H), 7.23 (t, J=6.4 Hz, 1 H), 6.65 (s, 1 H), 5.53 (br s, 1 H), 5.10 (s, 1 H), 4.68 (d, J=5.2 Hz, 1 H), 4.57 (q, J=7.2 Hz, 2 H), 4.43-4.41 (m, 1 H), 2.53-2.51 (m, 1 H), 2.11-2.09 (m, 1 H), 1.44-1.41 (m, 5 H), 1.12 (s, 3 H).

Synthetic Method 13

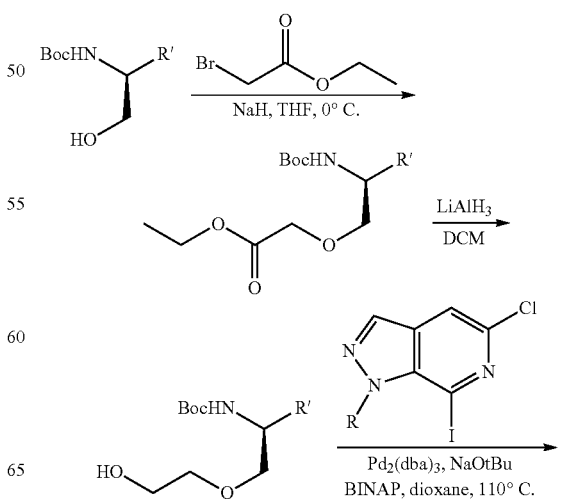

85

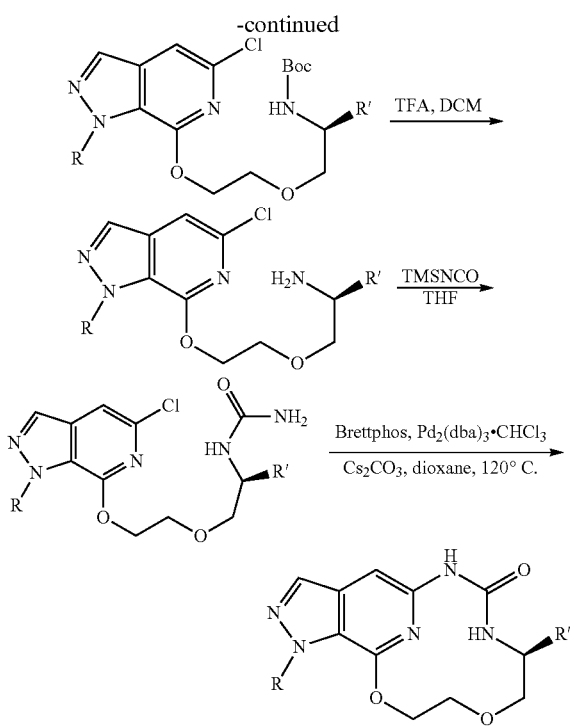

Example 29

(9S)-1-methyl-9-phenyl-1,6,9,10,12,13-hexahydro-5, 15-(azeno)pyrazolo[4,3-i][1,12,4,6]dioxadiazacyclo-tetradecin-7(8H)-one Step 1: (S)-Ethyl 2-(2-((tert-butoxycarbonyl) amino)-2-phenylethoxy)acetate (S)-Ethyl 2-(2-((tert-butoxycarbonyl)amino)-2-phenylethoxy)acetate was synthesized by similar alkylation procedure as described in example 1 at step 1, except ethyl 2-bromoacetate was used. MS (EI) calc'd for $C_{17}H_{26}NO_5$ [M+H]$^+$ 324, found 324.

Step 2: (S)-tert-Butyl (2-(2-hydroxyethoxy)-1-phenylethyl)carbamate

To a solution of (S)-ethyl 2-(2-((tert-butoxycarbonyl) amino)-2-phenylethoxy)acetate (5.0 g, 15.5 mmol) in DCM (100 mL) was added LiAlH$_4$ (1.2 g, 30.9 mmol) in portions at 0° C. The reaction mixture was warmed slowly to 25° C. and stirred for 1 h. The reaction was quenched by saturated Na$_2$SO$_4$ (10 mL) and then filtered. The filtrate was evaporated under reduced pressure. The residue was purified by chromatography on SiO$_2$, eluted with petroleum ether/

86

EtOAc (1:1) to give (S)-tert-butyl (2-(2-hydroxyethoxy)-1-phenylethyl)-carbamate. MS (EI) calc'd for $C_{15}H_{24}NO_4$ [M+H]$^+$ 282, found 282.

Step 3: (S)-tert-Butyl 2-(2-(5-chloro-1-methyl-1H-pyrazolo[3,4-c]pyridin-7-yloxy)ethoxy)-1-phenyl-ethylcarbamate Into a 50-mL round-bottom flask, was placed a mixture of sodium tert-butoxide (524 mg, 5.45 mmol), 2,2'-bis(diphenylphosphino)-1,1'-binaphthalene (170 mg, 0.273 mmol), Pd(OAc)$_2$ (250 mg, 0.273 mmol), 5-chloro-7-iodo-1-methyl-1H-pyrazolo[3,4-c]pyridine (800 mg, 2.73 mmol), (S)-tert-butyl (2-(2-hydroxyethoxy)-1-phenylethyl)carbamate (844 mg, 3.00 mmol) in toluene (20 mL) under a nitrogen atmosphere. After stirring for 10 h at 90° C., the resulting mixture was cooled down to ambient temperature, quenched with water, and extracted with ethyl acetate (3×50 mL). The combined organic layers was dried (Na$_2$SO$_4$), and filtered. After concentrated under reduced pressure, the residue was purified by chromatography on SiO$_2$, eluted with petroleum ether/ethyl acetate (1:5) to give (R)-tert-butyl (2-(2-((5-chloro-1-methyl-1H-pyrazolo[3,4-c]pyridin-7-yl)oxy) ethoxy)-1-phenylethyl)carbamate; MS (EI) calc'd for $C_{22}H_{28}ClN_4O_4$ [M+H]$^+$ 447, found 447.

Step 4: (S)-2-(2-(5-Chloro-1-methyl-1H-pyrazolo[3, 4-c]pyridin-7-yloxy)ethoxy)-1-phenylethanamine This compound was synthesized by similar TFA deprotection as described in example 1 at step 4 except (S)-tert-butyl 2-(2-(5-chloro-1-methyl-1H-pyrazolo[3,4-c]pyridin-7-yloxy)ethoxy)-1-phenylethylcarbamate was used. MS (EI) calc'd for $C_{17}H_{20}ClN_4O_2$ [M+H]$^+$ 347, found 347.

Step 5: (S)-1-(2-(2-(5-Chloro-1-methyl-1H-pyrazolo [3,4-c]pyridin-7-yloxy)ethoxy)-1-phenylethyl)urea This compound was synthesized by similar urea formation as described in example 1 at step 5 except (S)-2-(2-(5-chloro-1-methyl-1H-pyrazolo[3,4-c]pyridin-7-yloxy) ethoxy)-1-phenylethanamine was used. MS (EI) calc'd for $C_{18}H_{21}ClN_5O_3$ [M+H]$^+$ 390, found 390.

Step 6: (9S)-1-Methyl-9-phenyl-1,6,9,10,12,13-hexahydro-5,15-(azeno)pyrazolo [4,3-i][1,12,4,6] dioxadiazacyclotetradecin-7(8H)-one This compound was synthesized by the similar Buchwald coupling as described in example 1 at step 6 except (S)-1-(2-(2-(5-chloro-1-methyl-1H-pyrazolo[3,4-c]pyridin-7-yloxy)ethoxy)-1-phenylethyl)urea was used. MS (EI) calc'd for $C_{18}H_{20}N_5O_3$ [M+H]$^+$ 354, found 354; $^1$H NMR (300 MHz, DMSO-d$_6$) δ 10.12 (d, J=5.4 Hz, 1 H), 9.12 (s, 1 H), 7.99 (s, 1 H), 7.38-7.20 (m, 5 H), 6.71 (s, 1 H), 4.89-4.86 (m, 1H), 4.72-4.64 (m, 2 H), 4.18 (s, 3 H), 4.01-3.85 (m, 3 H), 3.73-3.68 (m, 1 H).

Synthetic Method 14

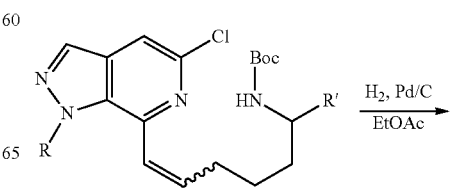

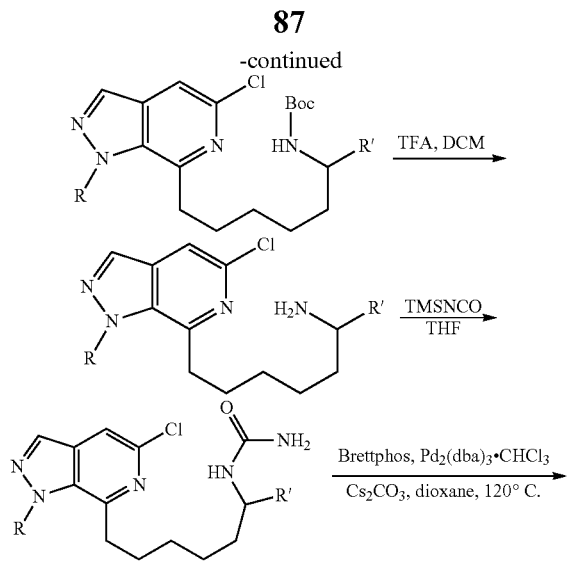

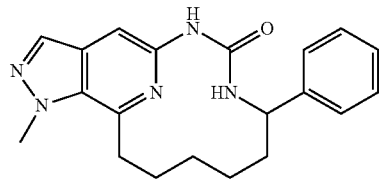 [SMILES: Cn1ncc2cc3nc(c21)CCCCCC(c1ccccc1)NC(=O)N3]

Example 30

1-Methyl-9-phenyl-1,6,9,10,11,12,13,14-octahydro-5,15-(azeno)pyrazolo[4,3-f][1,3]diazacyclotetradecin-7(8H)-one Step 1: tert-Butyl (6-(5-chloro-1-methyl-1H-pyrazolo[3,4-c]pyridin-7-yl)-1-phenylhexyl)carbamate This compound was synthesized by similar hydrogenation as described in example 1 at step 3 except tert-butyl (6-(5-chloro-1-methyl-1H-pyrazolo[3,4-c]pyridin-7-yl)-1-phenylhex-5-en-1-yl)carbamate was used. MS (EI) calc'd for $C_{24}H_{32}ClN_4O_2$ [M+H]$^+$ 443, found 443.

Step 2: 6-(5-Chloro-1-methyl-1H-pyrazolo[3,4-c]pyridin-7-yl)-1-phenylhexan-1-amine This compound was synthesized by similar TFA deprotection as described in example 1 at step 4 except tert-butyl 6-(5-chloro-1-methyl-1H-pyrazolo[3,4-c]pyridin-7-yl)-1-phenylhexylcarbamate was used. MS (EI) calc'd for $C_{19}H_{24}ClN_4$ [M+H]$^+$ 343, found 343.

Step 3: 1-(6-(5-Chloro-1-methyl-1H-pyrazolo[3,4-c]pyridin-7-yl)-1-phenylhexyl)urea This compound was synthesized by similar urea formation as described in example 1 at step 5 except 6-(5-chloro-1-methyl-1H-pyrazolo[3,4-c]pyridin-7-yl)-1-phenylhexan-1-amine was used. MS (EI) calc'd for $C_{20}H_{25}ClN_5O$ [M+H]$^+$ 386, found 386.

Step 4: 1-Methyl-9-phenyl-1,6,9,10,11,12,13,14-octahydro-5,15-(azeno)pyrazolo[4,3-f][1,3]diazacyclotetradecin-7(8H)-one This compound was synthesized by similar Buchwald coupling as described in example 1 at step 6 except 1-(6-(5-chloro-1-methyl-1H-pyrazolo[3,4-c]pyridin-7-yl)-1-phenylhexyl)urea was used. MS (EI) calc'd for $C_{20}H_{24}N_5O$ [M+H]$^+$ 350, found 350; $^1$H NMR (400 MHz, DMSO-d$_6$) δ 11.34 (d, J=5.4 Hz, 1 H), 9.21 (s, 1 H), 8.04 (s, 1 H), 7.33-7.29 (m, 2 H), 7.23-7.18 (m, 3 H), 6.98 (s, 1 H), 4.90 (br s, 1 H), 4.30 (s, 3 H), 3.65-3.59 (m, 1 H), 3.45-3.40 (m, 1 H), 2.19-2.11 (m, 2 H), 2.02-2.00 (m, 1 H), 1.84-1.79 (m, 2 H), 1.59-1.58 (m, 1 H), 1.44-1.42 (m, 1 H), 1.25-1.17 (m, 1 H).

Synthetic Method 15

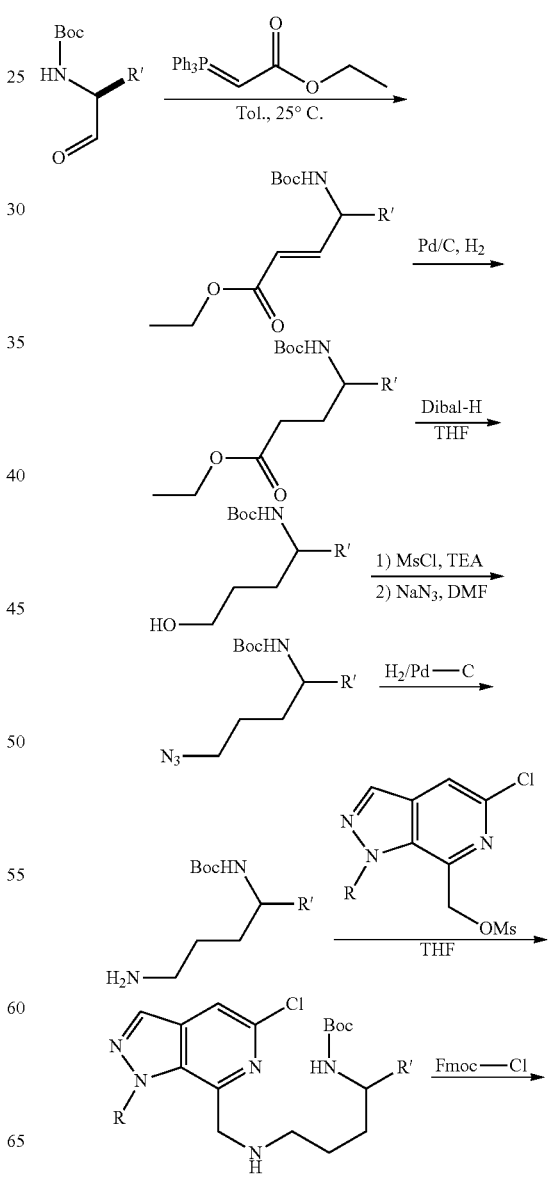

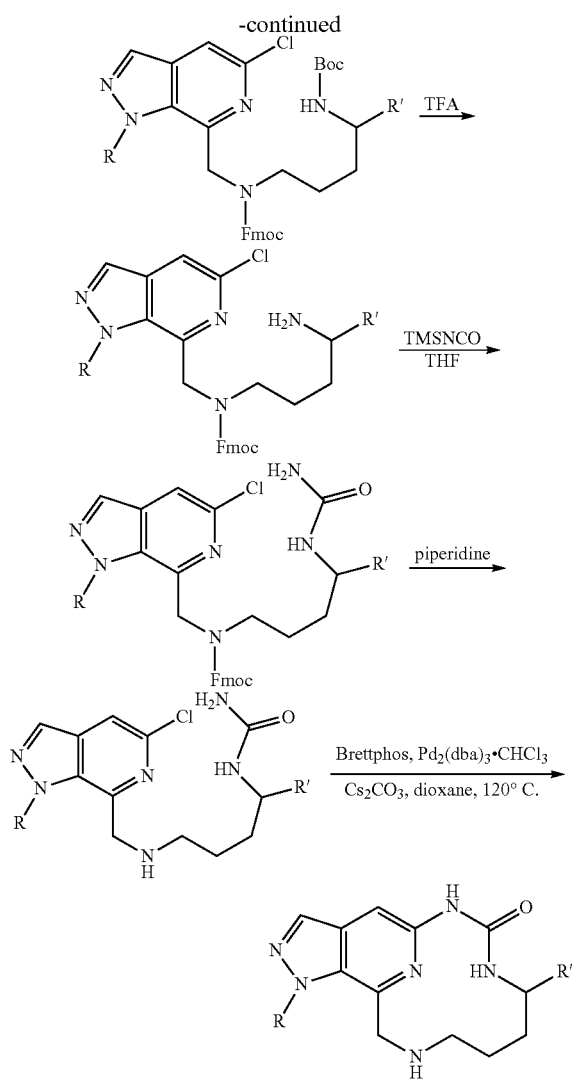

Example 31

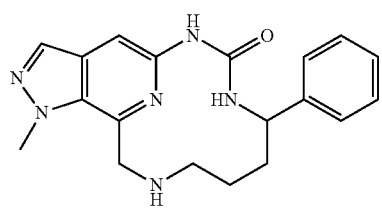 [SMILES: Cn1ncc2cc3nc(c21)CNCCCC(c1ccccc1)NC(=O)N3]

1-Methyl-9-phenyl-1,6,9,10,11,12,13,14-octahydro-5,15-(azeno)pyrazolo[3,4-k][1,3,8]triazacyclotetradecin-7(8H)-one Step 1: (E)-Ethyl 4-(tert-butoxycarbonylamino)-4-phenylbut-2-enoate (S)-Tert-butyl(2-oxo-1-phenylethyl)carbamate (35.0 g, 149 mmol) and ethyl 2-(triphenylPhosphoranylidene)acetate (51.8 g, 149 mmol) were dissolved in toluene (500 mL) and the mixture was stirred at 25° C. for 18 h. The solvent was evaporated under reduced pressure. The residue was purified by chromatography on $SiO_2$, eluted with petroleum ether/EtOAc (20:1) to give (E)-ethyl 4-(tert-butoxycarbonylamino)-4-phenylbut-2-enoate. MS (EI) calc'd for $C_{16}H_{22}NO_4$ $[M+H]^+$ 292, found 292.

Step 2: Ethyl 4-(tert-butoxycarbonylamino)-4-phenylbutanoate

This compound was synthesized by similar hydrogenation as described in example 1 at step 3 except (E)-ethyl 4-(tert-butoxycarbonylamino)-4-phenylbut-2-enoate was used. MS (EI) calc'd for $C_{16}H_{24}NO_4$ $[M+H]^+$ 294, found 294.

Step 3: tert-Butyl (4-hydroxy-1-phenylbutyl)carbamate

Diisobutyl aluminium hydride (228 mL, 228 mmol) was added to a stirred, cooled (−10° C.) mixture of ethyl 4-(tert-butoxycarbonylamino)-4-phenylbutanoate (35.0 g, 114 mmol) in DCM (500 mL) and the mixture was stirred at 0° C. for 2 h. Then reaction was quenched by saturated aqueous sodium potassium tartrate (200 mL). The resulting mixture was extracted with DCM, washed with brine, dried ($Na_2SO_4$), filtered and concentrated under reduced pressure. The residue was purified by chromatography on $SiO_2$, eluted with petroleum ether/EtOAc (1:1) to give tert-butyl (4-hydroxy-1-phenylbutyl)carbamate as a colorless solid. MS (EI) calc'd for $C_{15}H_{24}NO_3$ $[M+H]^+$ 266, found 266.

Step 4: tert-Butyl (4-azido-1-phenylbutyl)carbamate

Sodium azide (0.625 g, 9.61 mmol) was added to a stirred mixture of 4-((tert-butoxycarbonyl)amino)-4-phenylbutyl methanesulfonate (1.1 g, 3.20 mmol, prepared from the corresponding hydroxy compound from step 3) in DMF (20 mL). The resulting mixture was stirred at 70° C. for 3 h and then cooled down to ambient temperature. Saturated ammonium chloride (10 mL) was added and the reaction mixture was extracted with ethyl acetate (3×20 mL). The combined organic layers was washed with brine (2×20 mL), dried ($Na_2SO_4$), and filtered. The filtratet was evaporated under reduced pressure to give in tert-butyl (4-azido-1-phenylbutyl)carbamate; MS (EI) calc'd for $C_{15}H_{23}N_4O_2$ $[M+H]^+$ 291, found 291.

Step 5: tert-Butyl (4-amino-1-phenylbutyl)carbamate

A mixture of t tert-butyl (4-azido-1-phenylbutyl)carbamate (810 mg, 2.79 mmol and Pd/C (148 mg, 1.40 mmol) (10%, dry) in MeOH (20 mL) was purged in 3 atm hydrogen and stirred for 12 h at 25° C. under an atmosphere of hydrogen (3 atm). Filtration and concentration under reduced pressure afforded tert-butyl (4-amino-1-phenylbutyl)carbamate; MS (EI) calc'd for $C_{15}H_{25}N_2O_2$ $[M+H]^+$ 265, found 265.

Step 6: tert-Butyl 4-((5-chloro-1-methyl-1H-pyrazolo[3,4-c]pyridin-7-yl)methylamino)-1-phenylbutylcarbamate (5-chloro-1-methyl-1H-pyrazolo[3,4-c]pyridin-7-yl) methyl methanesulfonate (600 mg, 2.17 mmol) was added to a stirred mixture of tert-butyl (4-amino-1-phenylbutyl)carbamate (575 mg, 2.17 mmol) and TEA (438 mg, 600 uL, 4.34 mmol) in THF (20 mL) and the mixture was stirred at ambient temperature for 3 h. The reaction mixture was concentrated under reduced pressure. The residue was purified by chromatography on SiO$_2$, eluted with DCM/MeOH (20:1) to give tert-butyl 4-((5-chloro-1-methyl-1H-pyrazolo [3,4-c]pyridin-7-yl)methylamino)-1-phenylbutylcarbamate. MS (EI) calc'd for C$_{23}$H$_{31}$ClN$_5$O$_2$ [M+H]$^+$ 444, found 444.

Step 7: (9H-Fluoren-9-yl)methyl (4-((tert-butoxycarbonyl)amino)-4-phenylbutyl)((5-chloro-1-methyl-1H-pyrazolo[3,4-c]pyridin-7-yl)methyl)carbamate To a stirred mixture of 9-fluorenylmethyl chloroformate (287 mg, 1.11 mmol) and tert-butyl (4-((5-chloro-1-methyl-1H-pyrazolo[3,4-c]pyridin-7-yl)methyl)amino)-1-phenylbutylcarbamate (410 mg, 0.92 mmol) in dioxane (15 mL) and water (15 mL) was added NaHCO$_3$ (116 mg, 1.38 mmol). The mixture was stirred at 25° C. for 3 h and then diluted with EtOAc, washed with brine, dried (Na$_2$SO$_4$), filtered and concentrated under reduced pressure.

The residue was purified by chromatography on SiO$_2$, eluted with DCM/MeOH (20:1) to give (9H-fluoren-9-yl) methyl (4-((tert-butoxycarbonyl)amino)-4-phenylbutyl)((5-chloro-1-methyl-1H-pyrazolo[3,4-c]pyridin-7-yl)methyl) carbamate. MS (EI) calc'd for C$_{38}$H$_{41}$ClN$_5$O$_4$ [M+H]$^+$ 666, found 666.

Step 8: (9H-Fluoren-9-yl) methyl (4-amino-4-phenylbutyl) ((5-chloro-1-methyl-1H-pyrazolo[3, 4-c] pyridin-7-yl)methyl)carbamate This compound was synthesized by similar TFA deprotection as described in example 1 at step 4 except (9H-fluoren-9-yl)methyl (4-((tert-butoxycarbonyl)amino)-4-phenylbutyl)((5-chloro-1-methyl-1H-pyrazolo[3,4-c]pyridin-7-yl)methyl)carbamate was used. MS (EI) calc'd for C$_{33}$H$_{33}$ClN$_5$O$_2$ [M+H]$^+$ 566, found 566.

Step 9: (9H-Fluoren-9-yl) methyl ((5-chloro-1-methyl-1H-pyrazolo [3,4-c]pyridin-7-yl)methyl)(4-phenyl-4-ureidobutyl)carbamate This compound was synthesized by similar urea formation as described in example 1 at step 5 except (9H-fluoren-9-yl) methyl (4-amino-4-phenylbutyl) ((5-chloro-1-methyl-1H-pyrazolo[3, 4-c]pyridin-7-yl)methyl)carbamate was used. MS (EI) calc'd for C$_{34}$H$_{34}$ClN$_6$O$_3$ [M+H]$^+$ 609, found 609.

Step 10: 1-(4-(((5-Chloro-1-methyl-1H-pyrazolo [3,4-c]pyridin-7-yl)methyl)amino)-1-phenylbutyl) urea To a mixture of (9H-fluoren-9-yl) methyl ((5-chloro-1-methyl-1H-pyrazolo[3,4-c]pyridin-7-yl)methyl)(4-phenyl-4-ureidobutyl)carbamate (150 mg, 0.25 mmol) in MeOH (5 mL) was added piperidine (1 mL, 40.9 mmol). The mixture was stirred for 1 h at 25° C. and then concentrated under reduced pressure. The residue was diluted with EtOAc, washed with brine, dried (Na$_2$SO$_4$) and concentrated under reduced pressure to give 1-(4-(((5-chloro-1-methyl-1H-pyrazolo [3, 4-c] pyridin-7-yl)methyl)amino)-1-phenylbutyl)urea. MS (EI) calc'd for C$_{19}$H$_{23}$ClN$_6$O [M+H]$^+$ 387, found 387.

Step 11: 1-Methyl-9-phenyl-1,6,9,10,11,12,13,14-octahydro-5,15-(azeno)pyrazolo[3,4-k][1,3,8]triazacyclotetradecin-7(8H)-one This compound was synthesized by similar Buchwald coupling as described in example 1 at step 6 except 1-(4-(((5-chloro-1-methyl-1H-pyrazolo [3, 4-c] pyridin-7-yl)methyl)amino)-1-phenylbutyl)urea was used. MS (EI) calc'd for C$_{19}$H$_{23}$N$_6$O [M+H]$^+$ 351, found 351; $^1$H NMR (400 MHz, DMSO-d$_6$) δ 12.01 (br s, 1 H), 9.14 (s, 1 H), 8.04 (s, 1 H), 7.33-7.29 (m, 2 H), 7.25-7.18 (m, 3 H), 6.94 (s, 1 H), 4.79 (br s, 1 H), 4.55 (m, 2 H), 4.26 (s, 3 H), 2.93-2.83 (m, 2 H), 2.47 (br s, 1 H), 2.16-2.12 (m, 1 H), 2.06-2.02 (m, 1 H), 1.66-1.62 (m, 1 H), 1.36-1.31 (m, 1 H).

Synthetic Method 16

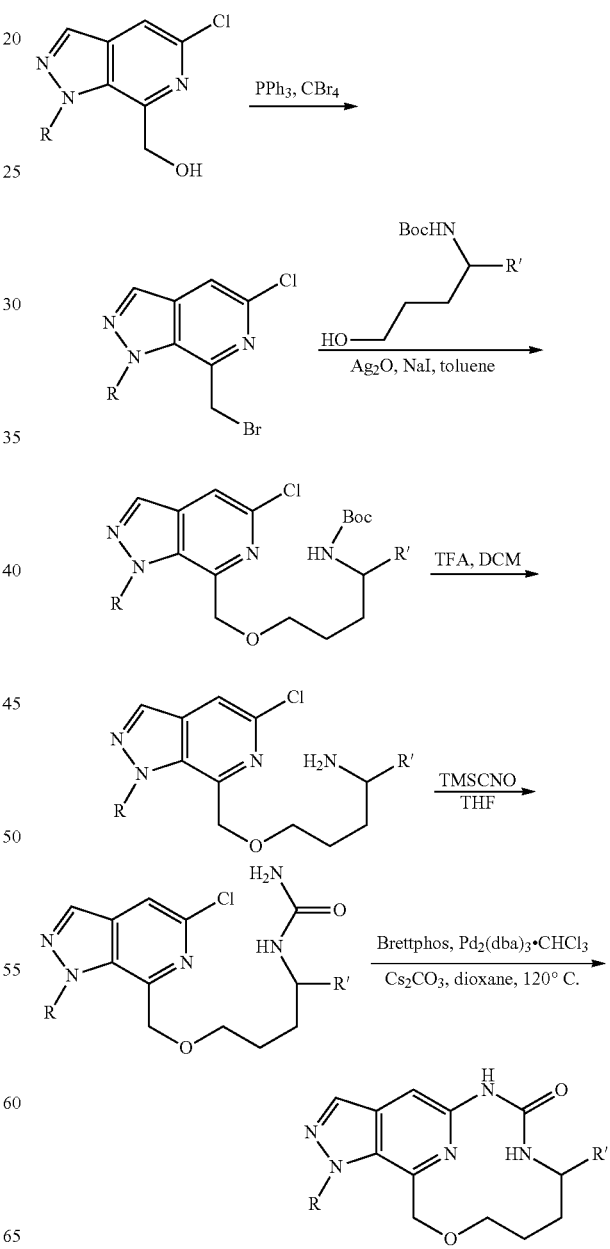

Example 32

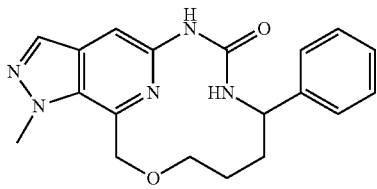 [SMILES: Cn1ncc2cc3nc(c21)COCCCC(c1ccccc1)NC(=O)N3]

1-Methyl-9-phenyl-1,6,9,10,11,12-hexahydro-5,15-(azeno)pyrazolo[4,3-k][1,6,8]oxadiazacyclotetradecin-7(8H,14H)-one

Step 1: 7-(Bromomethyl)-5-chloro-1-methyl-1H-pyrazolo [3, 4-c]pyridine

To a solution of (5-chloro-1-methyl-1H-pyrazolo[3,4-c]pyridin-7-yl)methanol (1.5 g, 7.59 mmol) in MeCN (30 mL) were added CBr$_4$ (5.0 g, 15.2 mmol), 2,6-lutidine (0.81 g, 7.59 mmol), triphenylphosphine (4.0 g, 15.2 mmol). The resulting solution was stirred for 2 h at 25° C. The reaction was quenched by saturated NaHCO$_3$ (20 mL) and then, extracted with EtOAc, washed with brine, dried (Na$_2$SO$_4$), filtered. The filtrate was concentrated under vacuum. The residue was purified by chromatography on SiO$_2$, eluted with petroleum ether/EtOAc (10:1) to give 7-(bromomethyl)-5-chloro-1-methyl-1H-pyrazolo [3, 4-c] pyridine. MS (EI) calc'd for C$_8$H$_7$BrClN$_3$ [M+H]$^+$ 260, 262, found 260, 262.

Step 2: tert-Butyl (4-((5-chloro-1-methyl-1H-pyrazol[3,4-c]pyridin-7-yl)methoxy)-1-phenylbutyl)carbamate To a solution of tert-butyl (4-hydroxy-1-phenylbutyl)carbamate (1.0 g, 4.03 mmol) and 7-(bromomethyl)-5-chloro-1-methyl-1H-pyrazolo[3,4-c]pyridine (0.70 g, 2.69 mmol) in toluene (30 mL) were added silver oxide (3.1 g, 13.4 mmol) and sodium iodide (0.81 g, 5.37 mmol). The mixture was purged with nitrogen and stirred for 10 h at 25° C. The resulting mixture was filtered and the filtrate was concentrated under reduced pressure. The residue was diluted with EtOAc, washed with brine, dried (Na$_2$SO$_4$), filtered and concentrated under reduced pressure. The residue was purified by chromatography on SiO$_2$, eluted with petroleum ether/EtOAc (5:1) to give tert-butyl (4-((5-chloro-1-methyl-1H-pyrazolo[3,4-c]pyridin-7-yl)methoxy)-1-phenylbutyl)carbamate. MS (EI) calc'd for C$_{23}$H$_{30}$ClN$_4$O$_3$ [M+H]$^+$ 445, found 445.

Step 3: 4-((5-Chloro-1-methyl-1H-pyrazolo[3, 4-c]pyridin-7-yl)methoxy)-1-phenylbutan-1-amine This compound was synthesized by similar TFA deprotection as described in example 1 at step 4 except tert-butyl (4-((5-chloro-1-methyl-1H-pyrazolo[3,4-c]pyridin-7-yl)methoxy)-1-phenylbutyl)carbamate was used. MS (EI) calc'd for C$_{18}$H$_{22}$ClN$_4$O [M+H]$^+$ 345, found 345.

Step 4: 1-(4-((5-Chloro-1-methyl-1H-pyrazolo [3,4-c]pyridin-7-yl)methoxy)-1-phenylbutyl)urea This compound was synthesized by using similar urea formation as described in example 1 at step 5 except 4-((5-chloro-1-methyl-1H-pyrazolo[3,4-c]pyridin-7-yl)methoxy)-1-phenylbutan-1-amine was used. MS (EI) calc'd for C$_{19}$H$_{23}$ClN$_5$O$_2$ [M+H]$^+$ 388, found 388.

Step 5: 1-Methyl-9-phenyl-1,6,9,10,11,12-hexahydro-5,15-(azeno)pyrazolo[4,3-k][1,6,8]oxadiazacyclotetradecin-7(8H,14H)-one This compound was synthesized by similar Buchwald coupling as described in example 1 at step 6 except 1-(4-((5-Chloro-1-methyl-1H-pyrazolo[3,4-c]pyridin-7-yl)methoxy)-1-phenylbutyl)urea was used. MS (EI) calc'd for C$_{19}$H$_{22}$N$_5$O$_2$ [M+H]$^+$ 351, found 351; $^1$H NMR (400 MHz, DMSO-d$_6$) δ 9.24 (br s, 1 H), 8.07 (s, 1 H), 7.34-7.30 (m, 2 H), 7.26-7.19 (m, 3 H), 7.00 (s, 1 H), 6.07 (br s, 1 H), 5.38 (m, 2 H), 4.81 (br s, 1 H), 4.21 (s, 3 H), 3.92-3.88 (m, 1 H), 3.80-3.76 (m, 1 H), 213-1.96 (m, 2 H), 1.82-1.80 (m, 1 H), 1.42-1.38 (m, 1 H).

Synthetic Method 17

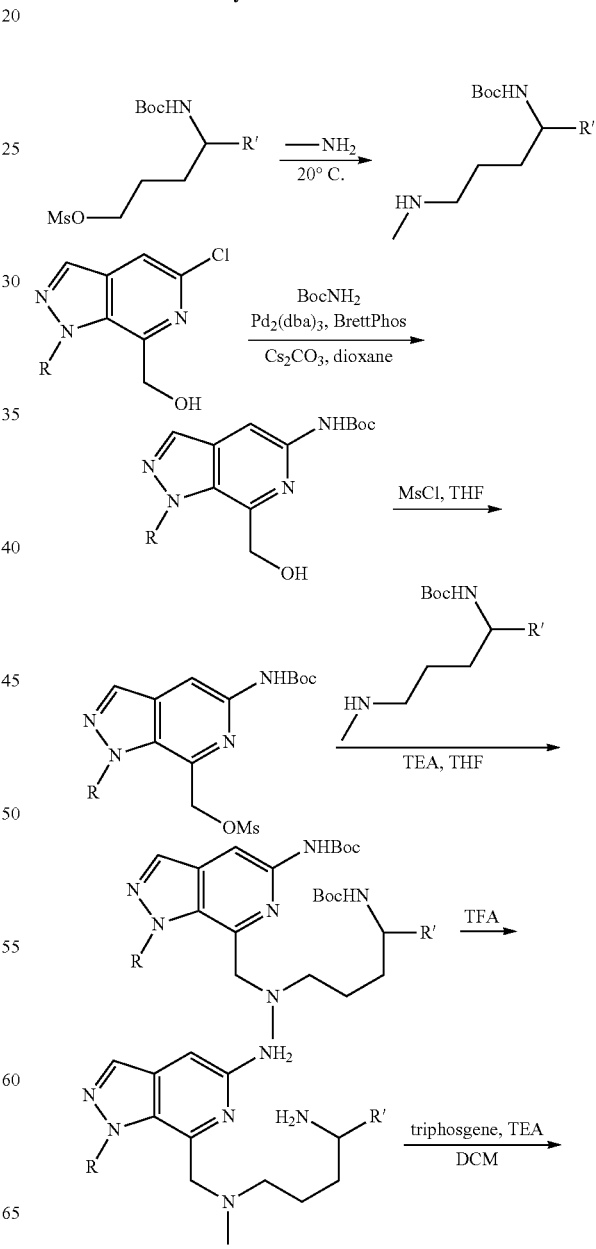

-continued

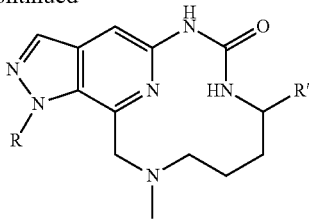

Example 33

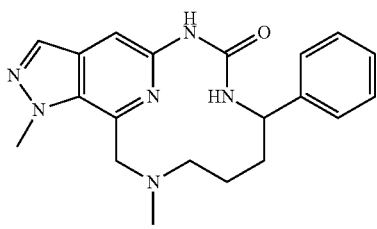 [SMILES: CN1CCCC(c2ccccc2)NC(=O)Nc2cc3cnn(C)c3c(n2)C1]

1,13-Dimethyl-9-phenyl-1,6,9,10,11,12,13,14-octahydro-5,15-(azeno)pyrazolo[3,4-k][1,3,8]triazacyclotetradecin-7(8H)-one

Step 1: tert-Butyl (4-(methylamino)-1-phenylbutyl)carbamate

Methylamine (723 mg, 30% in methanol, 23.29 mmol) was added to a mixture of (R)-4-((tert-butoxycarbonyl)amino)-4-phenylbutyl methanesulfonate (800 mg, 2.33 mmol) in MeOH (10 mL). After stirring for 3 h at 60° C., The reaction mixture was evaporated under reduced pressure. The residue was purified by chromatography on SiO$_2$, eluted with dichloromethane/methanol (5:1) to give (R)-tert-butyl (4-(methylamino)-1-phenylbutyl)carbamate; MS (EI) calc'd for $C_{16}H_{27}N_2O_2$ [M+H]$^+$ 279, found 279.

Step 2: tert-Butyl (7-(hydroxymethyl)-1-methyl-1H-pyrazolo[3,4-c]pyridin-5-yl)carbamate Into a mixture of (5-chloro-1-methyl-1H-pyrazolo[3,4-c]pyridin-7-yl)methanol (1.0 g, 5.06 mmol). tert-butyl carbamate (0.8 g, 6.83 mmol), 2-(dicyclohexylphosphino)3,6-dimethoxy-2',4',6'-triisopropyl-1,1'-biphenyl (300 mg, 0.559 mmol), and Cs$_2$CO$_3$ (3.2 g, 9.82 mmol)) in dioxane (30 mL),) was added Pd$_2$(dba)$_3$ (500 mg, 0.546 mmol). The resulting mixture was stirred for 3 h at 120° C. and cooled down to ambient temperature. The reaction mixture was diluted with water (100 mL), and extracted with ethyl acetate (3×100 mL). The combined organic layers were washed with brine, dried (Na$_2$SO$_4$), and filtered. The filtrate was evaporated under reduced pressure. The residue was purified by chromatography on SiO$_2$, eluted with petroleum ether/ethyl acetate (4:1-1:1) to give tert-butyl (7-(hydroxymethyl)-1-methyl-1H-pyrazolo[3,4-c]pyridin-5-yl)carbamate. MS (EI) calc'd for $C_{13}H_{19}N_4O_3$ [M+H]$^+$ 279, found 279.

Step 3: (5-((tert-Butoxycarbonyl)amino)-1-methyl-1H-pyrazolo[3,4-c]pyridin-7-yl)methyl methanesulfonate To a mixture of tert-butyl (7-(hydroxymethyl)-1-methyl-1H-pyrazolo[3,4-c]pyridin-5-yl)carbamate (1.0 g, 3.59 mmol), TEA (0.751 ml, 5.39 mmol) in tetrahydrofuran (30 mL) was added methanesulfonyl chloride (0.336 mL, 4.31 mmol) at 0° C. After stirring for 2 h at 25° C., saturated sodium hydrogen carbonate (10 mL) was added and the mixture was extracted with ethyl acetate (3×20 mL). The combined organic phases were washed with brine (3×20 mL), dried (Na$_2$SO$_4$), and filtered. The filtrate was evaporated under reduced pressure to give (5-((tert-butoxycarbonyl)amino)-1-methyl-1H-pyrazolo[3,4-c]pyridin-7-yl) methyl methanesulfonate. MS (EI) calc'd for $C_{14}H_{21}N_4O_5S$ [M+H]$^+$ 357, found 357.

Step 4: tert-Butyl 4-(((5-tert-butoxycarbonylamino-1-methyl-1H-pyrazolo[3,4-c]pyridin-7-yl)methyl)(methyl)amino)-1-phenylbutylcarbamate TEA (0.18 mL, 1.26 mmol) was added to a mixture of tert-butyl (4-(methylamino)-1-phenylbutyl)carbamate (352 mg, 1.26 mmol) and (5-((tert-butoxycarbonyl)amino)-1-methyl-1H-pyrazolo[3,4-c]pyridin-7-yl)methyl methanesulfonate (450 mg, 1.26 mmol) in THF (15 mL). The resulting mixture was stirred at 25° C. for 12 h and concentrated under reduced pressure. The residue was purified by Prep-TLC (DCM/MeOH=20:1) to give tert-butyl 4-(((5-tert-butoxycarbonylamino-1-methyl-1H-pyrazolo[3,4-c]pyridin-7-yl)methyl)(methyl)amino)-1-phenylbutylcarbamate. MS (EI) calc'd for $C_{29}H_{43}N_6O_4$ [M+H]$^+$ 539, found 539.

Step 5: N1-((5-Amino-1-methyl-1H-pyrazolo[3,4-c]pyridin-7-yl)methyl)-N1-methyl-4-phenylbutane-1,4-diamine To a mixture of tert-butyl 4-(((5-tert-butoxycarbonylamino-1-methyl-1H-pyrazolo[3,4-c]pyridin-7-yl)methyl)(methyl)amino)-1-phenylbutylcarbamate (350 mg, 0.65 mmol) in dichloromethane (3 mL) was added TFA (1.01 mL, 12.99 mmol). After stirring for 2 h at 25° C., the reaction mixture was diluted with dichloromethane (50 mL), washed with aqueous sodium hydroxide (5%, 15 mL), dried (Na$_2$SO$_4$) and filtered. The filtrate was evaporated under reduced pressure to give N1-((5-amino-1-methyl-1H-pyrazolo[3,4-c]pyridin-7-yl)methyl)-N1-methyl-4-phenylbutane-1,4-diamine; MS (EI) calc'd for $C_{19}H_{27}N_6$[M+H]$^+$ 339, found 339.

Step 6: 1,13-Dimethyl-9-phenyl-1,6,9,10,11,12,13,14-octahydro-5,15-(azeno)pyrazolo[3,4-k][1,3,8]triazacyclotetradecin-7(8H)-one This compound was synthesized by the same method as described in example 15 at step 8 except N1-((5-amino-1-methyl-1H-pyrazolo[3,4-c]pyridin-7-yl)methyl)-N1-methyl-4-phenylbutane-1,4-diamine was used. MS (EI) calc'd for $C_{20}H_{25}N_6O$ [M+H]$^+$ 365, found 365; $^1$H NMR (400 MHz, CD$_3$OD) δ 8.09 (s, 1 H), 7.34-7.24 (m, 6 H), 5.36-5.30 (m, 2 H), 5.01-4.99 (m, 1 H), 4.35 (s, 3 H), 3.89-3.86 (m, 1 H), 3.08-3.25 (m, 1 H), 3.17 (s, 3 H), 2.29-2.23 (m, 2 H), 2.01-1.97 (m, 1 H), 1.66-1.64 (m, 1 H).

Synthetic Method 18

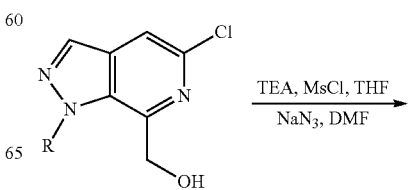

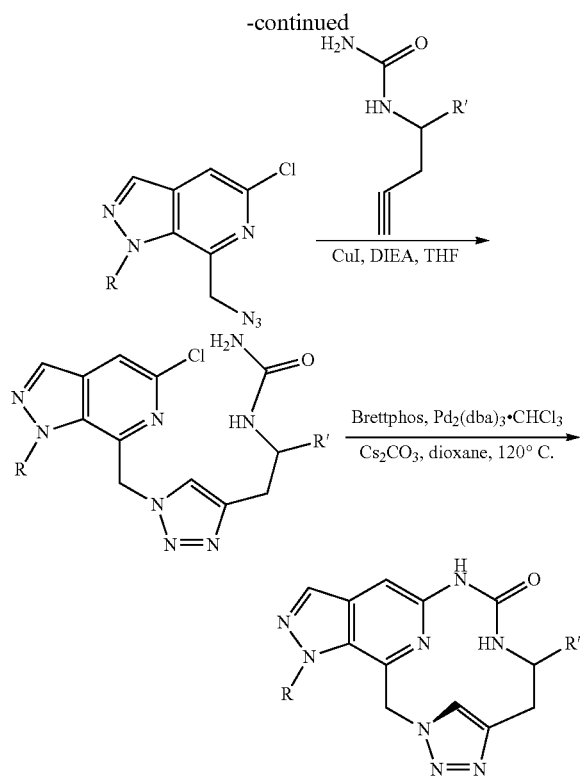

Example 34

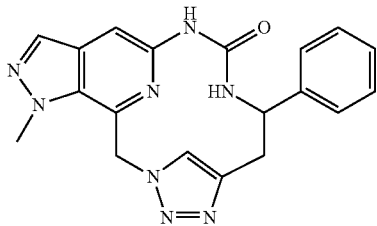 [SMILES: Cn1ncc2cc3nc(c21)Cn1cc(nn1)CC(c1ccccc1)NC(=O)N3]

1-methyl-9-phenyl-1,6,9,10-tetrahydro-5,16-(azeno)-14,11-(metheno)pyrazolo[4,3-l][1,2,3,7,9]pentaazacyclopentadecin-7(8H,15H)-one Step 1: 1-(4-Fluorophenyl)-1H-pyrazolo[3,4-c]pyridin-5-amine To a solution of [5-chloro-1-methyl-1H-pyrazolo[3,4-c]pyridin-7-yl]methanol (550 mg, 2.78 mmol) and TEA (564 mg, 5.57 mmol) in THF (50 mL) was added methanesulfonylchloride (450 mg, 3.92 mmol) dropwise at 0° C. during 5 min. The resulting solution was stirred at 25° C. for 2 h and then quenched by saturated NaHCO₃ (10 mL). The mixture was extracted with EtOAc, washed with brine, dried (Na₂SO₄), and filtered. The filtrate was concentrated under reduced pressure to give [5-chloro-1-methyl-1H-pyrazolo[3,4-c]pyridin-7-yl]methyl methanesulfonate (500 mg) as a solid, which was dissolved in DMF (20 mL). Then sodium azide (354.5 mg, 5.45 mmol) was added. After stirred at 25° C. for 2 h, the resulting mixture was diluted with water, extracted with EtOAc, washed with brine, dried (Na₂SO₄), and filtered. The filtrate was concentrated under reduced pressure to give 7-(azidomethyl)-5-chloro-1-methyl-1H-pyrazolo[3,4-c]pyridine, which was used directly for the next step without further purification. MS (EI) calc'd for $C_8H_8ClN_6$ $[M+H]^+$ 223, found 223.

Step 2: [2-[1-([5-Chloro-1-methyl-1H-pyrazolo[3,4-c]pyridin-7-yl]methyl)-1H-1,2,3-triazol-4-yl]-1-phenylethyl]urea To a solution of 7-(azidomethyl)-5-chloro-1-methyl-1H-pyrazolo[3,4-c]pyridine (225 mg, 1.01 mmol) in THF (10 mL) were added (1-phenylbut-3-yn-1-yl)urea (190 mg, 1.01 mmol), CuI (192 mg, 1.01 mmol) and DIEA (0.88 mL, 5.05 mmol). The resulting mixture was stirred for 2 h at 25° C. under nitrogen. The solids were filtered out. The filtrate was concentrated under vacuum. The residue was purified by chromatography on SiO₂, eluted with petroleum ether/EtOAc (1:1) to give [2-[1-([5-chloro-1-methyl-1H-pyrazolo[3,4-c]pyridin-7-yl]methyl)-1H-1,2,3-triazol-4-yl]-1-phenylethyl]urea. MS (EI) calc'd for $C_{19}H_{20}ClN_8O$ $[M+H]^+$ 411, found 411.

Step 3: 1-Methyl-9-phenyl-1,6,9,10-tetrahydro-5,16-(azeno)-14,11-(metheno)pyrazolo [4,3-l][1,2,3,7,9]pentaazacyclopentadecin-7(8H,15H)-one To a mixture of [2-[1-([5-chloro-1-methyl-1H-pyrazolo[3,4-c]pyridin-7-yl]methyl)-1H-1,2,3-triazol-4-yl]-1-phenylethyl]urea (43.3 mg, 0.11 mmol) in dioxane (5 mL) was added Pd₂(dba)₃·CHCl₃ (5.5 mg, 0.01 mmol), Brettphos (4.2 mg, 0.01 mmol), Cs₂CO₃ (69 mg, 0.21 mmol). The resulting mixture was purged by bubbling nitrogen for 3 min and then heated to 120° C. After stirred for 15 h, the mixture was concentrated under reduced pressure. The residue was purified by Prep-HPLC with the following conditions: Column, SunFire Prep C18 OBD Column, 5 μm, 19×50 mm; Mobile phase, H₂O (0.05% TFA)/CH₃CN (20%~44% in 10 min); Detector, 254 nm, and 220 nm. The desired fraction afforded 3.3 mg 1-methyl-9-phenyl-1,6,9,10-tetrahydro-5,16-(azeno)-14,11-(metheno)pyrazolo [4,3-l][1,2,3,7,9]pentaazacyclopentadecin-7(8H,15H)-one. MS (EI) calc'd for $C_{19}H_{19}N_8O$ $[M+H]^+$ 375, found 375; ¹H NMR (400 MHz, DMSO-d₆) δ 9.17 (s, 1 H), 8.34 (s, 1 H), 8.28 (d, J=7.2 Hz, 1H), 8.10 (s, 1 H), 7.30 (t, J=7.2 Hz, 2 H), 7.21 (t, J=7.2 Hz, 1 H), 7.09-7.06 (m, 3 H), 6.73 (d, J=17.2 Hz, 1 H), 6.49 (d, J=17.2 Hz, 1 H), 5.16 (t, J=7.6 Hz, 1 H), 4.43 (s, 3 H), 3.61 (m, 1 H), 3.10 (d, J=14.0 Hz, 1 H).

Example 35

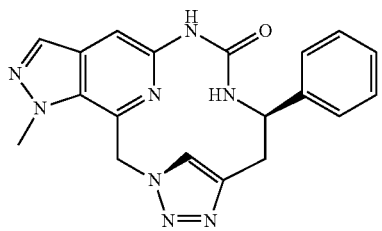

(9R)-1-Methyl-9-phenyl-1,6,9,10-tetrahydro-5,16-(azeno)-14,11-(metheno)pyrazolo[4,3-l][1,2,3,7,9]pentaazacyclopentadecin-7(8H,15H)-one This compound was obtained by the chiral separation of 1-methyl-9-phenyl-1,6,9,10-tetrahydro-5,16-(azeno)-14,11-(metheno)pyrazolo[4,3-l][1,2,3,7,9]pentaazacyclopentadecin-7(8H,15H)-one: MS (EI) calc'd for $C_{19}H_{19}N_8O$ [M+H]$^+$ 375, found 375; $^1$H NMR (400 MHz, $CD_3OD$) δ 8.73 (d, J=7.6 Hz, 1 H), 8.33 (s, 1 H), 8.02 (s, 1 H), 7.32 (t, J=7.2 Hz, 2 H), 7.23 (t, J=7.2 Hz, 1 H), 7.12-7.08 (m, 3 H), 6.75 (d, J=17.2 Hz, 1 H), 6.45 (d, J=17.2 Hz, 1 H), 5.33-5.30 (m, 1 H), 4.48 (s, 3 H), 3.75-3.71 (m, 1 H), 3.33-3.26 (m, 1 H).

Example 36

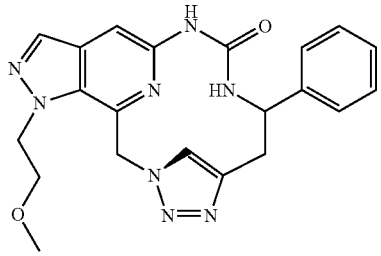

1-(2-Methoxyethyl)-9-phenyl-1,6,9,10-tetrahydro-5,16-(azeno)-14,11-(metheno)pyrazolo[4,3-l][1,2,3,7,9]pentaazacyclopentadecin-7(8H,15H)-one This compound was synthesized by the same method as described in example 34 except 2-bromoethyl methyl ether was used: MS (EI) calc'd for $C_{21}H_{23}N_8O_2$[M+H]$^+$ 419, found 419; $^1$H NMR (400 MHz, DMSO-$d_6$) δ 9.19 (s, 1 H), 8.41 (s, 1 H), 8.23 (s, 1 H), 8.21 (s, 1 H), 7.30 (t, J=7.2 Hz, 2 H), 7.21 (t, J=7.2 Hz, 1 H), 7.08 (t, J=3.4 Hz, 3 H), 6.69 (d, J=17.2 Hz, 1 H), 6.34 (d, J=17.2 Hz, 1 H), 5.16 (t, J=7.6 Hz, 1 H), 4.86 (t, J=4.8 Hz, 2 H), 3.86-3.76 (m, 2 H), 3.61 (m, 1 H), 3.27 (s, 3 H), 3.11(d, J=14.4 Hz, 1 H).

Example 37

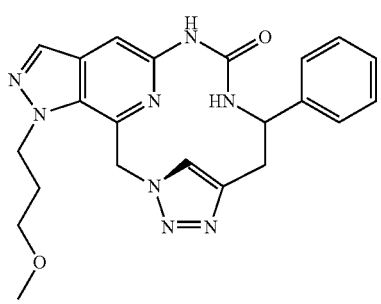

1-(3-Methoxypropyl)-9-phenyl-1,6,9,10-tetrahydro-5,16-(azeno)-14,11-(metheno)pyrazolo[4,3-l][1,2,3,7,9]pentaazacyclopentadecin-7(8H,15H)-one This compound was synthesized by the same method as described in example 34 except 1-chloro-3-methoxypropane was used: MS (EI) calc'd for $C_{22}H_{25}N_8O_2$[M+H]$^+$ 433, found 433; $^1$H NMR (400 MHz, DMSO-$d_6$) δ 9.19 (s, 1 H), 8.38 (s, 1 H), 8.22 (s, 1 H), 8.20 (s, 1 H), 7.30 (t, J=7.2 Hz, 2 H), 7.21 (t, J=7.2 Hz, 1 H), 7.07 (d, J=7.6 Hz, 3 H), 6.61 (d, J=17.2 Hz, 1 H), 6.37 (d, J=17.2 Hz, 1 H), 5.16 (t, J=7.6 Hz, 1 H), 4.75-4.69 (m, 2 H), 3.62-3.58 (m, 1 H), 3.37-3.33 (m, 2 H), 3.29 (s, 3 H), 3.14-3.09 (m, 1 H), 2.14-2.21 (m, 2 H).

Example 38

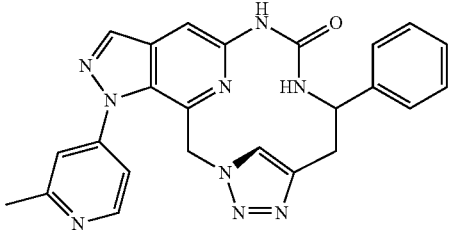

1-(2-Methylpyridin-4-yl)-9-phenyl-1,6,9,10-tetrahydro-5,16-(azeno)-14,11-(metheno)pyrazolo[4,3-l][1,2,3,7,9]pentaazacyclopentadecin-7(8H,15H)-one

Example 39

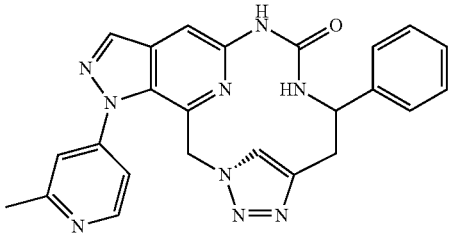

1-(2-Methylpyridin-4-yl)-9-phenyl-1,6,9,10-tetrahydro-5,16-(azeno)-14,11-(metheno)pyrazolo[4,3-l][1,2,3,7,9]pentaazacyclopentadecin-7(8H,15H)-one Step 1: 7-(Azidomethyl)-5-chloro-1-(2-methylpyridin-4-yl)-1H-pyrazolo[3,4-c]pyridine This compound was synthesized by the same method as described in example 34 at step 1 except (5-chloro-1-(2-methylpyridin-4-yl)-1H-pyrazolo[3,4-c]pyridin-7-yl)methanol was used. MS (EI) calc'd for $C_{13}H_{11}ClN_7$ [M+H]$^+$ 300, found 300.

Step 2: 1-(2-(1-((5-Chloro-1-(2-methylpyridin-4-yl)-1H-pyrazolo[3,4-c]pyridin-7-yl)methyl)-1H-1,2,3-triazol-4-yl)-1-phenylethyl)urea This compound was synthesized by the same method as described in example 34 at step 2 except 7-(azidomethyl)-5-chloro-1-(2-methylpyridin-4-yl)-1H-pyrazolo[3,4-c]pyridine was used. MS (EI) calc'd for $C_{24}H_{23}ClN_9O$ [M+H]$^+$ 488, found 488.

Step 3: 1-(2-Methylpyridin-4-yl)-9-phenyl-1,6,9,10-tetrahydro-5,16-(azeno)-14,11-(metheno)pyrazolo[4,3-l][1,2,3,7,9]pentaazacyclopentadecin-7(8H,15H)-one This compound was synthesized by the same method as described in example 34 at step 3 except 1-(2-(1-((5-chloro-1-(2-methylpyridin-4-yl)-1H-pyrazolo[3,4-c]pyridin-7-yl)methyl)-1H-1,2,3-triazol-4-yl)-1-phenylethyl)urea was used. The two atropisomers were separated by Prep-HPLC. 1-(2-Methylpyridin-4-yl)-9-phenyl-1,6,9,10-tetrahydro-5,16-(azeno)-14,11-(metheno)pyrazolo[4,3-l][1,2,3,7,9]pentaazacyclopentadecin-7(8H,15H)-one: MS (EI) calc'd for $C_{24}H_{22}N_9O$ [M+H]$^+$ 452, found 452; $^1$H NMR (400 MHz, DMSO-$d_6$) δ 9.38 (s, 1 H), 8.77 (d, J=5.2 Hz, 1 H), 8.58 (s, 1 H), 8.26 (s, 1 H), 8.14 (d, J=7.6 Hz, 1 H), 7.68 (t, J=10.8 Hz, 2 H), 7.32-7.21 (m, 4 H), 7.06 (d, J=7.6 Hz, 2 H), 5.84 (d, J=7.6 Hz, 2 H), 5.17 (t, J=7.6 Hz, 1 H), 3.63-3.58 (m, 1 H), 3.09 (d, J=13.6 Hz, 1 H), 2.68 (s, 3 H).
1-(2-Methylpyridin-4-yl)-9-phenyl-1,6,9,10-tetrahydro-5,16-(azeno)-14,11-(metheno)pyrazolo[4,3-l][1,2,3,7,9]pentaazacyclopentadecin-7(8H,15H)-one: MS (EI) calc'd for $C_{24}H_{22}N_9O$ [M+H]$^+$ 452, found 452; $^1$H NMR (400 MHz, DMSO-$d_6$) δ 9.16 (s, 1 H), 8.75 (d, J=5.2 Hz, 1 H), 8.55 (s, 1 H), 8.28 (s, 1 H), 7.71 (s, 1 H), 7.65 (d, J=5.2 Hz, 1 H), 7.48-7.35 (m, 5 H), 7.26 (t, J=6.8 Hz, 1 H), 7.16 (s, 1 H), 5.93 (d, J=17.2 Hz, 1 H), 5.75 (d, J=17.2 Hz, 1 H), 4.62 (t, J=7.4 Hz, 1 H), 3.48-3.43 (m, 1 H), 2.90-2.84 (m, 1 H), 2.68 (s, 3 H).

Synthetic Method 19

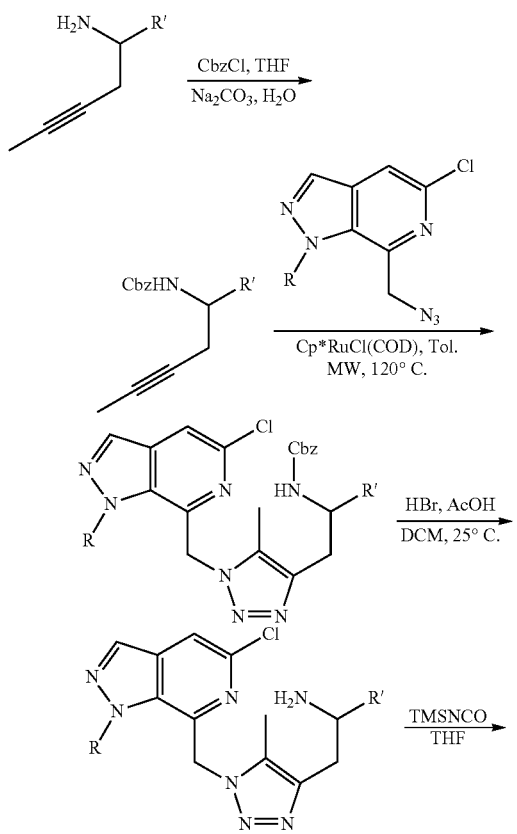

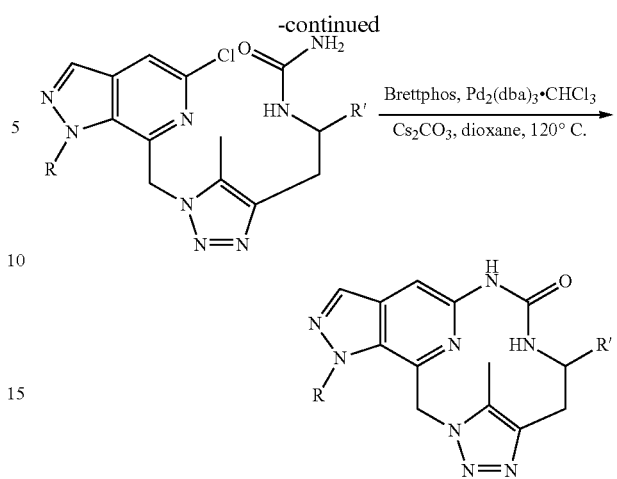

Example 40

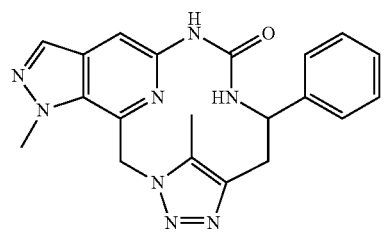 [SMILES: Cc1c2nnn1Cc1nc(cc3cnn(C)c13)NC(=O)NC(c1ccccc1)C2]

1,18-Dimethyl-9-phenyl-1,6,9,10-tetrahydro-5,16-(azeno)-14,11-(metheno)pyrazolo[4,3-l][1,2,3,7,9]pentaazacyclopentadecin-7(8H,15H)-one

Step 1: Benzyl (1-phenylpent-3-yn-1-yl)carbamate

To a solution of 1-phenylpent-3-yn-1-amine (prepared according to the procedure in *J. Organomet. Chem.* 1991, 420, 155.) (1.16 g, 7.29 mmol) in THF (10 mL) was added a solution of $K_2CO_3$ (1.21 g, 8.74 mmol)) in water (3.3 mL), and followed by the addition of benzyl chloroformate (1.25 mL, 8.74 mmol) dropwise with stirring at 0° C. After stirred for 12 h at 20° C., the resulting mixture was diluted with water, extracted with EtOAc, washed with brine, dried ($Na_2SO_4$), filtered and concentrated under reduced pressure. The residue was purified by chromatography on $SiO_2$, eluted with petroleum ether/EtOAc (2:1) to give benzyl (1-phenylpent-3-yn-1-yl)carbamate. MS (EI) calc'd for $C_{19}H_{20}NO_2$ [M+H]$^+$ 294, found 294.

Step 2: Benzyl (2-(1-((5-chloro-1-methyl-1H-pyrazolo[3,4-c]pyridin-7-yl)methyl)-5-methyl-1H-1,2,3-triazol-4-yl)-1-phenylethyl)carbamate A mixture of 7-(azidomethyl)-5-chloro-1-methyl-1H-pyrazolo[3,4-c]pyridine (637 mg, 2.86 mmol), benzyl (1-phenylpent-3-yn-1-yl)carbamate (700 mg, 2.39 mmol) and chloro(1,5-cyclooctadiene)(pentamethylcyclopentadienyl)ruthenium(II) (91 mg, 0.24 mmol) in toluene (10 mL) was purged by bubbling nitrogen for 3 min. The resulting mixture was stirred for 1 h at 120° C. under microwave irradiation and then concentrated under vacuum. The residue was purified by chromatography on SiO$_2$, eluted with petroleum ether/EtOAc (1:1) to give benzyl (2-(1-((5-chloro-1-methyl-1H-pyrazolo[3,4-c]pyridin-7-yl)methyl)-5-methyl-1H-1,2,3-triazol-4-yl)-1-phenylethyl)carbamate. MS (EI) calc'd for C$_{27}$H$_{27}$ClN$_7$O$_2$ [M+H]$^+$ 516, found 516.

Step 3: 2-(1-((5-Chloro-1-methyl-1H-pyrazolo[3,4-c]pyridin-7-yl)methyl)-5-methyl-1H-1,2,3-triazol-4-yl)-1-phenylethanamine To a solution of benzyl (2-(1-((5-chloro-1-methyl-1H-pyrazolo[3,4-c]pyridin-7-yl)methyl)-5-methyl-1H-1,2,3-triazol-4-yl)-1-phenylethyl)carbamate (190 mg, 0.37 mmol) in acetic acid (2 mL) was added aqueous HBr (0.30 mL, 1.84 mmol, 33%). The resulting solution was stirred for 4 h at 20° C. and then concentrated under vacuum. The residue was diluted with saturated NaHCO$_3$, extracted with DCM, washed with brine, dried (Na$_2$SO$_4$) and filtered. The filtrate was concentrated under reduced pressure The residue was purified by chromatography on SiO$_2$, eluted with DCM/MeOH (20:1) to give 2-(1-((5-chloro-1-methyl-1H-pyrazolo[3,4-c]pyridin-7-yl)methyl)-5-methyl-1H-1,2,3-triazol-4-yl)-1-phenylethanamine. MS (EI) calc'd for C$_{19}$H$_{21}$ClN$_7$ [M+H]$^+$ 382, found 382.

Step 4: 1-(2-(1-((5-Chloro-1-methyl-1H-pyrazolo[3,4-c]pyridin-7-yl)methyl)-5-methyl-1H-1,2,3-triazol-4-yl)-1-phenylethyl)urea This compound was synthesized by similar urea formation as described in example 1 at step 5 except 2-(1-((5-chloro-1-methyl-1H-pyrazolo[3,4-c]pyridin-7-yl)methyl)-5-methyl-1H-1,2,3-triazol-4-yl)-1-phenylethanamine was used. MS (EI) calc'd for C$_{20}$H$_{22}$ClN$_8$O [M+H]$^+$ 425, found 425.

Step 5: 1,18-Dimethyl-9-phenyl-1,6,9,10-tetrahydro-5,16-(azeno)-14,11-(metheno)pyrazolo [4,3-l][1,2,3,7,9]pentaazacyclopentadecin-7(8H,15H)-one This compound was synthesized by similar Buchwald coupling as described in example 1, step 6 except 1-(2-(1-((5-chloro-1-methyl-1H-pyrazolo[3,4-c]pyridin-7-yl)methyl)-5-methyl-1H-1,2,3-triazol-4-yl)-1-phenylethyl)urea was used: MS (EI) calc'd for C$_{20}$H$_{21}$N$_8$O [M+H]$^+$ 389, found 389; $^1$H NMR (400 MHz, DMSO-d$_6$) δ 8.87 (br s, 1 H), 8.12 (s, 1 H), 7.39-7.26 (m, 6 H), 7.04 (s, 1 H), 6.57 (d, J=16.4 Hz, 1 H), 5.87 (d, J=16.4 Hz, 1 H), 4.47-4.46 (m, 4 H), 3.48-3.46 (m, 1 H), 3.04-3.00 (m, 1 H), 2.53 (s, 3 H).

Synthetic Method 20

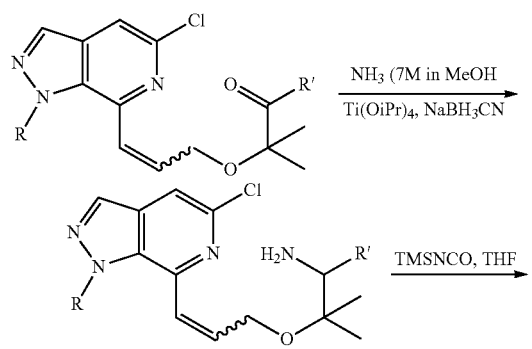

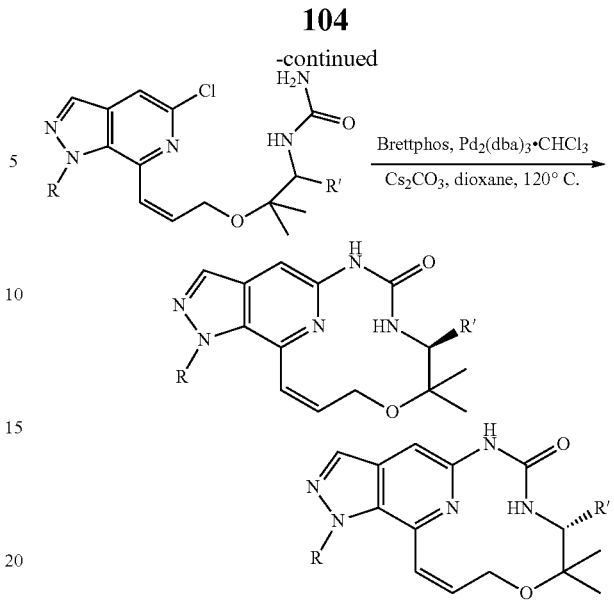

Example 41

(9S,13Z)-1-Ethyl-10,10-dimethyl-9-phenyl-1,6,9,10-tetrahydro-12H-5,15-(azeno)pyrazolo [4,3-i][1,4,6]oxadiazacyclotetradecin-7(8H)-one Example 42

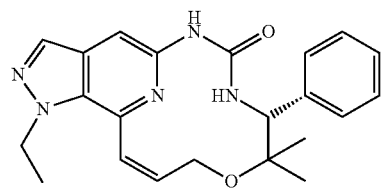

(9R,13Z)-1-Ethyl-10,10-dimethyl-9-phenyl-1,6,9,10-tetrahydro-12H-5,15-(azeno)pyrazolo [4,3-i][1,4,6]oxadiazacyclotetradecin-7(8H)-one Step 1: 2-((3-(5-Chloro-1-ethyl-1H-pyrazolo[3,4-c]pyridin-7-yl)allyl)oxy)-2-methyl-1-phenylpropan-1-amine To a mixture of 2-((3-(5-chloro-1-ethyl-1H-pyrazolo[3,4-c]pyridin-7-yl)allyl)oxy)-2-methyl-1-phenylpropan-1-one (1 g, 2.61 mmol) in EtOH (15 mL) were added a solution of ammonia in MeOH (7 M, 1.86 mL, 13.0 mmol) and tetraisopropoxytitanium (1.48 g, 5.21 mmol). After stirring for 15 h at 80° C., the resulting mixture was cooled down to ambient temperature. Then sodium cyanotrihydroborate (246 mg, 3.91 mmol) was added and stirred for 2 h at 25° C. The reaction mixture was quenched by water and concentrated under reduced pressure. The residue was diluted with water, extracted with EtOAc, washed with brine, dried (Na$_2$SO$_4$), filtered and concentrated under reduced pressure. The crude product was purified by chromatography on SiO$_2$, eluted with dichloromethane/methanol (20:1) to give 2-(3-(5-chloro-1-ethyl-1H-pyrazolo [3, 4-c] pyridin-7-yl)propoxy)-2-methyl-1-phenylpropan-1-amine. MS (EI) calc'd for C$_{21}$H$_{26}$ClN$_4$O [M+H]$^+$ 385, found 385.

Step 2: (Z)-1-(2-((3-(5-Chloro-1-ethyl-1H-pyrazolo [3,4-c]pyridin-7-yl)allyl)oxy)-2-methyl-1-phenylpropyl)urea Trimethylsilylisocyanate (554 mg, 4.81 mmol) was added to a stirred mixture of 2-((3-(5-chloro-1-ethyl-1H-pyrazolo [3,4-c]pyridin-7-yl)allyl)oxy)-2-methyl-1-phenylpropan-1-amine (370 mg, 0.96 mmol) in THF (10 mL). After stirring at 70° C. for 15 h, the resulting mixture was concentrated under reduced pressure. The residue was purified by Prep-TLC (dichloromethane/methanol=10:1) to give two isomers. (Z)-1-(2-((3-(5-chloro-1-ethyl-1H-pyrazolo[3,4-c]pyridin-7-yl)allyl)oxy)-2-methyl-1-phenylpropyl)urea; MS (EI) calc'd for C$_{22}$H$_{27}$ClN$_5$O$_2$ [M+H]$^+$ 428, found 428.
(E)-1-(2-((3-(5-chloro-1-ethyl-1H-pyrazolo[3,4-c]pyridin-7-yl)allyl)oxy)-2-methyl-1-phenylpropyl)urea as a colorless gum. MS (EI) calc'd for C$_{22}$H$_{27}$ClN$_5$O$_2$ [M+H]$^+$ 428, found 428.

Step 3: (9S,13Z)-1-Ethyl-10,10-dimethyl-9-phenyl-1,6,9,10-tetrahydro-12H-5,15-(azeno)pyrazolo[4,3-i][1,4,6]oxadiazacyclotetradecin-7(8H)-one and (9R,13Z)-1-ethyl-10,10-dimethyl-9-phenyl-1,6,9,10-tetrahydro-12H-5,15-(azeno)pyrazolo [4,3-i][1,4,6]oxadiazacyclotetradecin-7(8H)-one To a mixture of (Z)-1-(2-((3-(5-chloro-1-ethyl-1H-pyrazolo[3,4-c]pyridin-7-yl)allyl)oxy)-2-methyl-1-phenylpropyl)urea (30 mg, 0.07 mmol) in dioxane (3 mL) were added Pd$_2$(dba)$_3$.CHCl$_3$(6.42 mg, 7.01 μmol), Brettphos (3.76 mg, 7.01 μmol), and Cs$_2$CO$_3$ (45.7 mg, 0.14 mmol). The resulting mixture was purged by bubbling nitrogen for 3 min, heated to 110° C. and stirred for 4 h. The reaction mixture was concentrated under reduced pressure. The residue was purified by Prep-TLC (dichloromethane/methanol=20:1) and then further purified by chiral HPLC with conditions: Column, Chiralpak IC2*25 cm, 5 μm Chiral-P(IC) 001IC00CJ-LD016; Mobile phase, Hex/EtOH (20% in 60 min); Detector, 254 nm, and 220 nm. The desired fraction afforded two isomers:
Isomer 1: MS (EI) calc'd for C$_{22}$H$_{26}$N$_5$O$_2$ [M+H]$^+$ 392, found 392; $^1$H NMR (300 MHz, DMSO-d$_6$) δ 12.42 (d, J=8.7 Hz, 1 H), 9.10 (s, 1 H), 8.10 (s, 1 H), 7.48-7.45 (m, 2 H), 7.38-7.21 (m, 4 H), 7.02 (s, 1H), 6.38 (m, 1 H), 4.90-4.85 (m, 1 H), 4.71-4.62 (m, 2 H), 4.11-4.03 (m, 1 H), 3.76-3.68 (m, 1 H), 1.45 (t, J=7.2 Hz, 3 H), 1.13 (s, 3 H), 1.01 (s, 3 H).
Isomer 2: MS (EI) calc'd for C$_{22}$H$_{26}$N$_5$O$_2$ [M+H]$^+$ 392, found 392; $^1$H NMR (300 MHz, DMSO-d$_6$) δ 12.43 (d, J=8.7 Hz, 1H), 9.10 (s, 1 H), 8.10 (s, 1 H), 7.48-7.45 (m, 2 H), 7.38-7.25 (m, 4 H), 7.02 (s, 1H), 6.38 (m, 1 H), 4.89-4.87 (m, 1 H), 4.68-4.59 (m, 2 H), 4.11-4.03 (m, 1 H), 3.76-3.69 (m, 1 H), 1.45 (t, J=7.2 Hz, 3 H), 1.13 (s, 3 H), 1.01 (s, 3 H).

Example 43

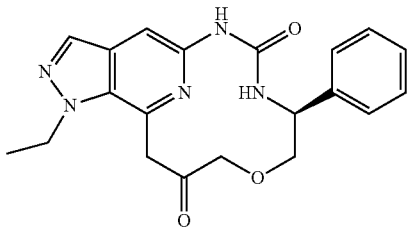 [SMILES: CCn1ncc2cc3nc(c21)CC(=O)COC[C@H](c1ccccc1)NC(=O)N3]

(9 S)-1-Ethyl-9-phenyl-1,6,9,10-tetrahydro-12H-5, 15-(azeno)pyrazolo [4,3-i][1,4,6]oxadiazacyclotetradecine-7,13(8H,14H)-dione 2-Iodoxybenzoic acid (30 mg, 0.11 mmol) was added to a stirred mixture of (9S,13R)-1-Ethyl-13-hydroxy-9-phenyl-1,6,9,10,13,14-hexahydro-12H-5,15-(azeno)pyrazolo[4,3-i][1,4,6]oxadiazacyclotetradecin-7(8H)-one (20 mg, 0.05 mmol) in acetonitrile (5 mL) and the reaction mixture was stirred at 80° C. for 1 h. The resulting mixture was filtered, and the filtrate was concentrated under reduced pressure. The residue was purified by Prep-TLC (dichloromethane/methanol=10:1) and then further purified by Prep-HPLC with conditions: Column, XBridge Prep Shield RP18, 5 μm, 19×150 mm; Mobile phase, H$_2$O (0.05% NH$_4$HCO$_3$)/CH$_3$CN (20~50% in 10 min); Detector, 254 nm, and 220 nm. The desired fraction afforded (9S)-1-ethyl-9-phenyl-1,6,9, 10,14-pentahydro-12H-5,15-(azeno)pyrazolo[4,3-i][1,4,6] oxadiazacyclotetradecin-7(8H),13-dione: MS (EI) calc'd for C$_{20}$H$_{22}$N$_5$O$_3$ [M+H]$^+$ 380, found 380; $^1$H NMR (400 MHz, DMSO-d$_6$): δ 10.36 (d, J=7.6 Hz, 1 H), 9.32 (s, 1 H), 8.14 (s, 1 H), 7.44-7.42 (m, 2 H), 7.35-7.31 (m, 2 H), 7.26-7.22 (m, 1 H), 7.08 (s, 1 H), 4.80-4.74 (m, 1 H), 4.70 (s, 1 H), 4.65 (s, 1 H), 4.60-4.54 (m, 3 H), 4.25 (d, J=15.6 Hz, 1 H), 4.10-4.06 (m, 1 H), 3.88-3.84 (m, 1 H), 1.42 (t, J=7.2 Hz, 3 H).

Example 44

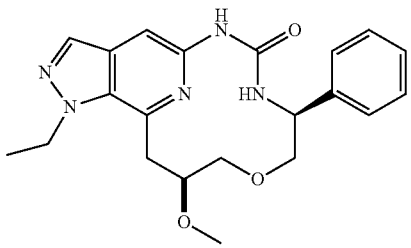 [SMILES: CCn1ncc2cc3nc(c21)C[C@H](OC)COC[C@H](c1ccccc1)NC(=O)N3]

(9R,13R)-1-Ethyl-13-methoxy-9-phenyl-1,6,9,10,13, 14-hexahydro-12H-5,15-(azeno)pyrazolo[4,3-i][1,4, 6]oxadiazacyclotetradecin-7(8H)-one To a mixture of (9R,13R)-1-ethyl-13-hydroxy-9-phenyl-1,6,9,10,13,14-hexahydro-12H-5,15-(azeno)pyrazolo[4,3-i]

[1,4,6]oxadiazacyclotetradecin-7(8H)-one (15 mg, 0.038 mmol) in dichloromethane (10 mL) were added 4 Å molecular sieve, trimethyloxonium tetrafluoroborate (10 mg, 0.068 mmol) and 1,8-bis(dimethylamino)naphthalene (15 mg, 0.07 mmol) under nitrogen. After stirring for 16 h at ambient temperature, the reaction mixture was filtered. The filtrate was concentrated under reduced pressure. The residue was purified by Prep-TLC (dichloromethane/methanol=15:1) and then further purified by Prep-HPLC with conditions: Column, SunFire Prep C18 OBD, 19×150 mm; Mobile phase, $H_2O$ (0.05% TFA)/$CH_3CN$ (15~65% in 8 min); Detector, 254 nm, and 220 nm. The desired fraction afforded (9R,13R)-1-ethyl-13-methoxy-9-phenyl-1,6,9,10,13,14-hexahydro-12H-5,15-(azeno)pyrazolo[4,3-i][1,4,6]oxadiazacyclotetradecin-7(8H)-one. MS (EI) calc'd for $C_{21}H_{26}N_5O_3$ $[M+H]^+$ 396, found 396; $^1H$ NMR (400 MHz, DMSO-$d_6$): δ 11.29 (d, J=6.0 Hz, 1 H), 9.19 (s, 1 H), 8.13 (s, 1 H), 7.38-7.32 (m, 4 H), 7.26-7.22 (m, 1 H), 7.07 (s, 1 H), 4.80-4.78 (m, 1 H), 4.66-4.58 (m, 2 H), 3.88-3.81 (m, 2 H), 3.73-3.71 (m, 1 H), 3.64-3.57 (m, 2 H), 3.50-3.40 (m, 5 H), 1.46 (t, J=7.0 Hz, 3 H).

Example 45

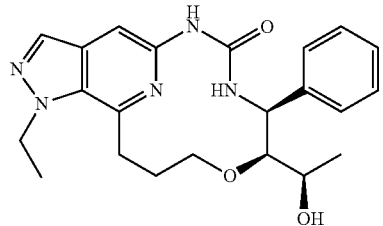 [SMILES: CCn1ncc2cc3nc(c21)CCCO[C@H]([C@@H](C)O)[C@H](c1ccccc1)NC(=O)N3]

(9 S,10 S)-1-Ethyl-10-[(1R)-1-hydroxyethyl]-9-phenyl-1,6,9,10,13,14-hexahydro-12H-5,15-(azeno)pyrazolo[4,3-i][1,4,6]oxadiazacyclotetradecin-7(8H)-one Example 46

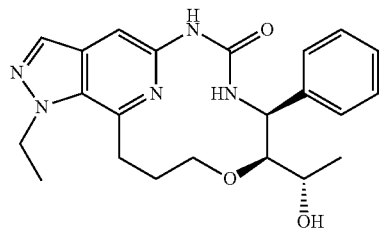 [SMILES: CCn1ncc2cc3nc(c21)CCCO[C@H]([C@H](C)O)[C@H](c1ccccc1)NC(=O)N3]

(9 S,10 S)-1-Ethyl-10-[(1 S)-1-hydroxyethyl]-9-phenyl-1,6,9,10,13,14-hexahydro-12H-5,15-(azeno)pyrazolo[4,3-i][1,4,6]oxadiazacyclotetradecin-7(8H)-one Example 47

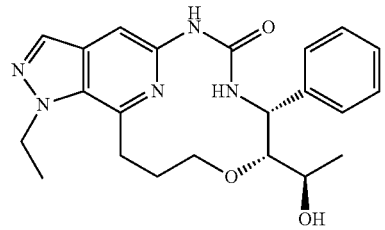 [SMILES: CCn1ncc2cc3nc(c21)CCCO[C@@H]([C@@H](C)O)[C@@H](c1ccccc1)NC(=O)N3]

(9R,10R)-1-Ethyl-10-[(1R)-1-hydroxyethyl]-9-phenyl-1,6,9,10,13,14-hexahydro-12H-5,15-(azeno)pyrazolo[4,3-i][1,4,6]oxadiazacyclotetradecin-7(8H)-one Example 48

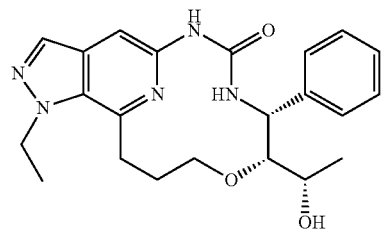 [SMILES: CCn1ncc2cc3nc(c21)CCCO[C@@H]([C@H](C)O)[C@@H](c1ccccc1)NC(=O)N3]

(9R,10R)-1-Ethyl-10-[(1S)-1-hydroxyethyl]-9-phenyl-1,6,9,10,13,14-hexahydro-12H-5,15-(azeno)pyrazolo[4,3-i][1,4,6]oxadiazacyclotetradecin-7(8H)-one To a stirred mixture of (9R,10R)-1-ethyl-10-(hydroxymethyl)-9-phenyl-1,6,9,10,13,14-hexahydro-12H-5,15-(azeno)pyrazolo[4,3-i][1,4,6]oxadiazacyclotetradecin-7(8H)-one and (9S,10S)-1-ethyl-10-(hydroxymethyl)-9-phenyl-1,6,9,10,13,14-hexahydro-12H-5,15-(azeno)pyrazolo[4,3-i][1,4,6]oxadiazacyclotetradecin-7(8H)-one (100 mg, 0.25 mmol) in DMSO (10 mL) was added 2-iodoxybenzoic acid (283 mg, 1.01 mmol). After stirring for 2 h at 25° C., the resulting mixture was quenched with water, extracted with EtOAc, then washed with brine, dried ($Na_2SO_4$) and filtered. The filtrate was concentrated under reduced pressure. The residue was dissolved in dry THF (10 mL) and methylmagnesium bromide (2.03 mL, 1 M in THF, 2.03 mmol) was added dropwise at 0° C. under nitrogen. The reaction mixture was stirred for 2 h at 0° C. and then quenched by water, extracted with EtOAc, washed with brine, dried ($Na_2SO_4$), filtered and concentrated under reduced pressure. The residue was purified by Prep-HPLC and chiral HPLC conditions: Column, Chiralpak IC2*25 cm, 5 μm Chiral-P(IC)001IC00CJ-LD016; Mobile phase, Hex/EtOH (40% in 35 min); Detector, 254 nm, and 220 nm. The desired fraction afforded four isomers:

Isomer 1; MS (EI) calc'd for $C_{22}H_{28}N_5O_3$ [M+H]$^+$ 410, found 410; $^1$H NMR (400 MHz, DMSO-d$_6$): δ 11.66 (d, J=8.4 Hz, 1 H), 9.13 (s, 1 H), 8.09 (s, 1 H), 7.50-7.48 (m, 2 H), 7.35-7.31 (m, 2 H), 7.27-7.24 (m, 1 H), 7.01 (s, 1 H), 4.69-4.59 (m, 4 H), 4.15-4.13 (m, 1 H), 3.46-3.41 (m, 3 H), 3.19-3.16 (m, 1 H), 3.03-3.01 (m, 1 H), 2.46-2.43 (m, 1 H), 2.12-2.10 (m, 1 H), 1.43 (t, J=7.2 Hz, 3 H), 1.03 (d, J=5.6 Hz, 3 H).

Isomer 2; MS (EI) calc'd for $C_{22}H_{28}N_5O_3$ [M+H]$^+$ 410, found 410; $^1$H NMR (400 MHz, DMSO-d$_6$): δ 11.66 (d, J=8.4 Hz, 1 H), 9.13 (s, 1 H), 8.09 (s, 1 H), 7.50-7.48 (m, 2 H), 7.34-7.31 (m, 2 H), 7.27-7.24 (m, 1 H), 7.01 (s, 1 H), 4.69-4.57 (m, 4 H), 4.15-4.13 (m, 1 H), 3.46-3.41 (m, 3 H), 3.19-3.16 (m, 1 H), 3.05-3.03 (m, 1 H), 2.51-2.49 (m, 1 H), 2.11-2.09 (m, 1 H), 1.43 (t, J=7.2 Hz, 3 H), 1.03 (d, J=5.6 Hz, 3 H).

Isomer 3: MS (EI) calc'd for $C_{22}H_{28}N_5O_3$ [M+H]$^+$ 410, found 410; $^1$H NMR (400 MHz, DMSO-d$_6$): δ 11.47 (d, J=9.2 Hz, 1 H), 9.16 (s, 1 H), 8.10 (s, 1 H), 7.47-7.45 (m, 2 H), 7.32-7.29 (m, 2 H), 7.25-7.21 (m, 1 H), 7.03 (s, 1 H), 5.05 (d, J=9.2 Hz, 1 H), 4.72 (d, J=5.6 Hz, 1 H), 4.58 (q, J=7.2 Hz, 2 H), 4.02-3.98 (m, 1 H), 3.61-3.59 (m, 1 H), 3.47-3.43 (m, 1 H), 3.32-3.28 (m, 1 H), 3.19-3.17 (m, 1 H), 2.97-2.95 (m, 1 H), 2.35-2.32 (m, 1 H), 2.20-2.18 (m, 1 H), 1.42 (t, J=7.2 Hz, 3 H), 1.06 (d, J=5.6 Hz, 3 H).

Isomer 4: MS (EI) calc'd for $C_{22}H_{28}N_5O_3$ [M+H]$^+$ 410, found 410; $^1$H NMR (400 MHz, DMSO-d$_6$): δ 11.47 (m, J=9.2 Hz, 1 H), 9.16 (s, 1 H), 8.09 (s, 1 H), 7.47-7.45 (m, 2 H), 7.32-7.28 (m, 2 H), 7.25-7.21 (m, 1 H), 7.02 (s, 1 H), 5.06-5.04 (d, J=9.2 Hz, 1 H), 4.72 (d, J=5.6 Hz, 1 H), 4.59 (q, J=7.2 Hz, 2 H), 4.00-3.98 (m, 1 H), 3.61-3.59 (m, 1 H), 3.48-3.42 (m, 1 H), 3.32-3.27 (m, 1 H), 3.19-3.17 (m, 1 H), 2.96-2.94 (m, 1 H), 2.44-2.42 (m, 1 H), 2.19-2.17 (m, 1 H), 1.43 (t, J=7.2 Hz, 3 H), 1.03 (d, J=5.6 Hz, 3 H).

Synthetic Method 21

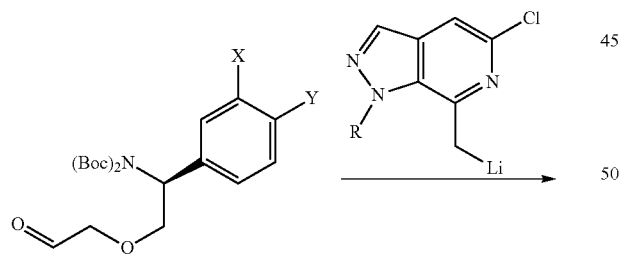

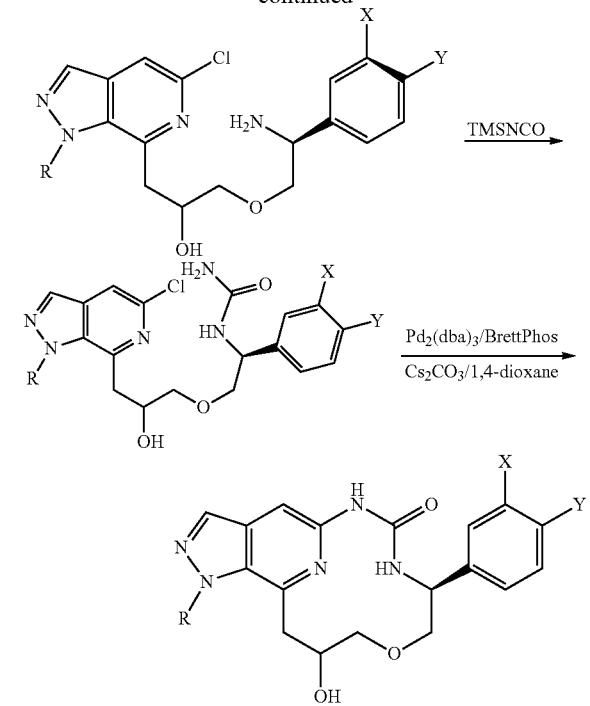

X = H or halogen
Y is H or —OCH$_3$

Example 49

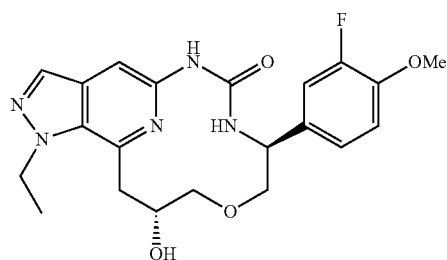 [SMILES: CCn1ncc2cc3nc(c21)C[C@@H](O)COC[C@H](c1ccc(OC)c(F)c1)NC(=O)N3]

(9S,13R)-1-Ethyl-9-(3-fluoro-4-methoxyphenyl)-13-hydroxy-1,6,9,10,13,14-hexahydro-12H-5,15-(azeno)pyrazolo[4,3-i][1,4,6]oxadiazacyclotetradecin-7(8H)-one Example 50

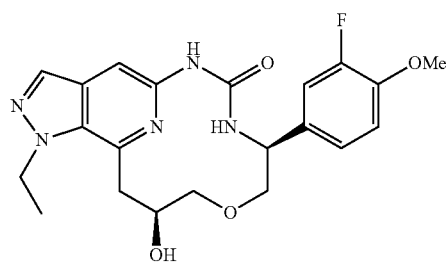 [SMILES: CCn1ncc2cc3nc(c21)C[C@H](O)COC[C@H](c1ccc(OC)c(F)c1)NC(=O)N3]

(9S,13S)-1-Ethyl-9-(3-fluoro-4-methoxyphenyl)-13-hydroxy-1,6,9,10,13,14-hexahydro-12H-5,15-(azeno)pyrazolo[4,3-i][1,4,6]oxadiazacyclotetradecin-7(8H)-one

Step 1. tert-Butyl N-[(tert-butoxy)carbonyl]-N-[(1S)-2-(3-{5-chloro-1-ethyl-1H-pyrazolo[3,4-c]pyridin-7-yl}-2-hydroxypropoxy)-1-(3-fluoro-4-methoxyphenyl)ethyl]carbamate To a solution of diisopropylamine (199 mg, 1.97 mmol) in THF (20 mL) was added n-BuLi (0.79 mL, 1.97 mmol) dropwise at −78° C. under $N_2$. The resulting mixture was stirred for 30 min at −78° C. and then a solution of 5-chloro-1-ethyl-7-methyl-1H-pyrazolo[3,4-c]pyridine (256 mg, 1.31 mmol) in THF (20 mL) was added dropwise during 20 min. After stirring for 30 min at −78° C., tert-butyl N-[(tert-butoxy)carbonyl]-N-[(1S)-1-(3-fluoro-4-methoxyphenyl)-2-(2-oxoethoxy)ethyl]carbamate (560 mg, 1.31 mmol) in THF (20 mL) was added dropwise at −78° C. The resulting mixture was stirred for 30 min at −78° C. and for 2 h at ambient temperature. The reaction mixture was quenched with water (20 mL) and extracted with ethyl acetate (3×100 mL). The combined organic layers were washed with brine (50 mL), dried over anhydrous sodium sulfate and filtered. The filtrate was concentrated under reduced pressure, the residue was purified by chromatography on $SiO_2$, eluted with petroleum ether/EtOAc (1:1) to give tert-butyl N-[(tert-butoxy)carbonyl]-N-[(1S)-2-(3-{5-chloro-1-ethyl-1H-pyrazolo[3,4-c]pyridin-7-yl}-2-hydroxypropoxy)-1-(3-fluoro-4-methoxyphenyl)ethyl]carbamate. MS (EI) calc'd for $C_{30}H_{41}ClFN_4O_7$ [M+H]$^+$ 623, found 623.

Step 2. 1-((S)-2-Amino-2-(3-fluoro-4-methoxyphenyl)ethoxy)-3-(5-chloro-1-ethyl-1H-pyrazolo[3,4-c]pyridin-7-yl)propan-2-ol To tert-butyl N-[(tert-butoxy)carbonyl]-N-[(1S)-2-(3-{5-chloro-1-ethyl-1H-pyrazolo[3,4-c]pyridin-7-yl}-2-hydroxypropoxy)-1-(3-fluoro-4-methoxyphenyl)ethyl]carbamate (500 mg, 0.802 mmol) in DCM (10.00 mL) was added TFA (10 mL). After stirring for 1 h at 25° C., the resulting mixture was concentrated under reduced pressure, diluted with water (20 mL), adjusted to PH=8 with $K_2CO_3$ powder and extracted with ethyl acetate (3×100 mL). The combined organic layers were washed with brine (50 mL), dried over anhydrous sodium sulfate and filtered. The filtrate was concentrated under reduced pressure to give 1-((S)-2-amino-2-(3-fluoro-4-methoxyphenyl)ethoxy)-3-(5-chloro-1-ethyl-1H-pyrazolo[3,4-c]pyridin-7-yl)propan-2-ol (400 mg), which was used directly for next step without further purification. MS (EI) calc'd for $C_{20}H_{25}ClFN_4O_3$ [M+H]$^+$ 423, found 423.

Step 3. 1-((S)-2-(3-(5-chloro-1-ethyl-1H-pyrazolo[3,4-c]pyridin-7-yl)-2-hydroxypropoxy)-1-(3-fluoro-4-methoxyphenyl)ethyl)urea To a mixture of 1-((S)-2-amino-2-(3-fluoro-4-methoxyphenyl)ethoxy)-3-(5-chloro-1-ethyl-1H-pyrazolo[3,4-c]pyridin-7-yl)propan-2-ol (400 mg, 0.948 mmol) in THF (20 mL) was added trimethylsilyl isocyanate (109 mg, 0.948 mmol). After stirring for 12 h at 60° C., the reaction mixture was quenched with water (20 mL) and extracted with ethyl acetate (3×50 mL). The combined organic layers were washed with brine (50 mL), dried over anhydrous sodium sulfate and filtered. The filtrate was concentrated under reduced pressure, the residue was purified by chromatography on $SiO_2$, eluted with dichloromethane/methanol (20:1) to give 1-((1S)-2-(3-(5-chloro-1-ethyl-1H-pyrazolo[3,4-c]pyridin-7-yl)-2-hydroxypropoxy)-1-(3-fluoro-4-methoxyphenyl)ethyl)urea. MS (EI) calc'd for $C_{21}H_{26}ClFN_5O_4$ [M+H]$^+$ 466, found 466.

Step 4. (9S,13R)-1-Ethyl-9-(3-fluoro-4-methoxyphenyl)-13-hydroxy-1,6,9,10,13,14-hexahydro-12H-5,15-(azeno)pyrazolo[4,3-i][1,4,6]oxadiazacyclotetradecin-7(8H)-one trifluoroacetic acid and (9S,13S)-1-ethyl-9-(3-fluoro-4-methoxyphenyl)-13-hydroxy-1,6,9,10,13,14-hexahydro-12H-5,15-(azeno)pyrazolo[4,3-i][1,4,6]oxadiazacyclotetradecin-7(8H)-on trifluoroacetic acid To a mixture of 1-((1S)-2-(3-(5-chloro-1-ethyl-1H-pyrazolo[3,4-c]pyridin-7-yl)-2-hydroxypropoxy)-1-(3-fluoro-4-methoxyphenyl)ethyl)urea (350 mg, 0.751 mmol) in dioxane (20 mL) were added BrettPhos (40.3 mg, 0.075 mmol), $Cs_2CO_3$ (490 mg, 1.502 mmol), $Pd_2(dba)_3$ $CHCl_3$ (78 mg, 0.075 mmol) under $N_2$. The resulting mixture was stirred for 3 h at 120° C. After cooling down to ambient temperature, the reaction mixture was quenched with water (20 mL). The solid was filtered out and the filtrate was extracted with ethyl acetate (3×50 mL). The combined organic layers were washed with brine (50 mL), dried over anhydrous sodium sulfate and filtered. The filtrate was concentrated under reduced pressure, the residue was purified by chromatography on $SiO_2$, eluted with dichloromethane/methanol (20:1) and then prep-HPLC with conditions: Column, XBridge Prep Shield RP18, 5 μm, 19×150 mm; Mobile phase, $H_2O$ (0.05% TFA)/$CH_3CN$ (20~50% in 10 min); Detector, 254 nm, and 220 nm. The desired fraction afforded two isomers.

Isomer A: (9S,13R) or (9S,13S)-1-Ethyl-9-(3-fluoro-4-methoxyphenyl)-13-hydroxy-1,6,9,10,13,14-hexahydro-12H-5,15-(azeno)pyrazolo[4,3-i][1,4,6]oxadiazacyclotetradecin-7(8H)-one trifluoroacetic acid: MS (EI) calc'd for $C_{21}H_{25}FN_5O_4$ [M+H]$^+$ 430, found 430; $^1$H NMR (300 MHz, $CD_3OD$): δ:7.99 (s, 1 H), 7.21-7.11 (m, 2 H), 7.05-7.00 (m, 2 H), 4.69-4.61 (m, 2 H), 4.11-4.06 (m, 1 H), 3.99-3.97 (m, 1 H), 3.83 (s, 3 H), 3.76-3.71 (m, 1 H), 3.59-3.51 (m, 3 H), 3.37-3.32 (m, 2 H), 1.51 (t, J=7.2 Hz, 3 H).

Isomer B: (9S,13S) or (9S,13R)-1-ethyl-9-(3-fluoro-4-methoxyphenyl)-13-hydroxy-1,6,9,10,13,14-hexahydro-12H-5,15-(azeno)pyrazolo[4,3-i][1,4,6]oxadiazacyclotetradecin-7(8H)-on trifluoroacetic acid: MS (EI) calc'd for $C_{21}H_{25}FN_5O_4$ [M+H]$^+$ 430, found 430; $^1$H NMR (300 MHz, $CD_3OD$): δ: 7.98 (s, 1 H), 7.19-7.15 (m, 2 H), 7.06-7.00 (m, 2 H), 4.69-4.60 (m, 1 H), 4.57-4.51 (m, 1 H), 4.12-4.08 (m, 1 H), 3.83 (s, 3 H), 3.76-3.71 (m, 1 H), 3.64-3.48 (m, 4 H), 3.29-3.27 (m, 2 H), 1.46 (t, J=7.2 Hz, 3 H).

The following examples were made by following similar procedures to example 49 and 50.

Example 51

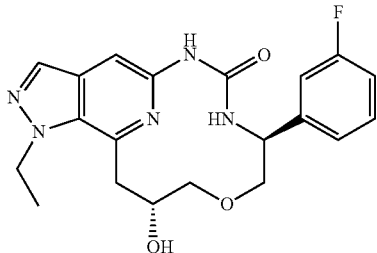 [SMILES: CCn1ncc2cc3nc(c21)C[C@@H](O)COC[C@H](c1cccc(F)c1)NC(=O)N3]

(9S,13R)-1-Ethyl-9-(3-fluorophenyl)-13-hydroxy-1,6,9,10,13,14-hexahydro-12H-5,15-(azeno)pyrazolo[4,3-i][1,4,6]oxadiazacyclotetradecin-7(8H)-one

Example 52

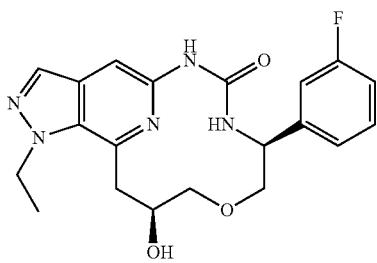 [SMILES: CCn1ncc2cc3nc(c21)C[C@H](O)COC[C@H](c1cccc(F)c1)NC(=O)N3]

(9S,13S)-1-Ethyl-9-(3-fluorophenyl)-13-hydroxy-1,6,9,10,13,14-hexahydro-12H-5,15-(azeno)pyrazolo[4,3-i][1,4,6]oxadiazacyclotetradecin-7(8H)-one

Example 53

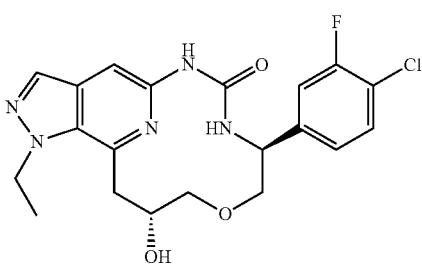 [SMILES: CCn1ncc2cc3nc(c21)C[C@@H](O)COC[C@H](c1ccc(Cl)c(F)c1)NC(=O)N3]

(9S,13R)-1-Ethyl-9-(4-chloro-3-fluorophenyl)-13-hydroxy-1,6,9,10,13,14-hexahydro-12H-5,15-(azeno)pyrazolo[4,3-i][1,4,6]oxadiazacyclotetradecin-7(8H)-one

Example 54

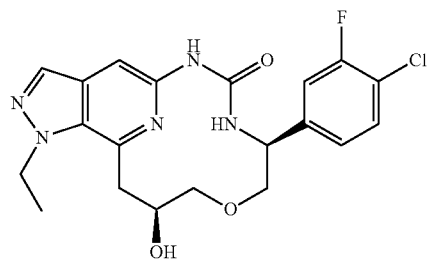 [SMILES: CCn1ncc2cc3nc(c21)C[C@H](O)COC[C@H](c1ccc(Cl)c(F)c1)NC(=O)N3]

(9S,13S)-1-Ethyl-9-(4-chloro-3-fluorophenyl)-13-hydroxy-1,6,9,10,13,14-hexahydro-12H-5,15-(azeno)pyrazolo[4,3-i][1,4,6]oxadiazacyclotetradecin-7(8H)-one Into a 40-mL vial purged and maintained with an inert atmosphere of nitrogen, were placed 1-((1S)-2-(3-(5-chloro-1-ethyl-1H-pyrazolo[3,4-c]pyridin-7-yl)-2-hydroxy-propoxy)-1-(4-chloro-3-fluorophenyl)ethyl)-urea (100 mg, 0.213 mmol), Pd$_2$(dba)$_3$ (20 mg, 0.021 mmol), Cs$_2$CO$_3$ (139 mg, 0.425 mmol), and BrettPhos (11.41 mg, 0.021 mmol) in 1,4-dioxane (20 mL). The resulting mixture was stirred for 10 h at 90° C. After cooling down to ambient temperature, the reaction mixture was diluted with water (50 mL) and extracted with ethyl acetate (3×50 mL). The combined organic layers were washed with brine (2×30 mL), dried over anhydrous sodium sulfate and filtered. The filtrate was concentrated under vacuum. The residue was purified by prep-TLC (DCM/MeOH=20:1) and then prep-HPLC with conditions: Column, XBridge Prep Shield RP18, 5 μm, 19×150 mm; Mobile phase, H$_2$O (0.05% NH$_4$HCO$_3$)/CH$_3$CN (20~50% in 10 min); Detector, 254 nm, and 220 nm. The desired fraction afforded four products.

Product A: (9S,13R) or (9S,13S)-1-Ethyl-9-(3-fluorophenyl)-13-hydroxy-1,6,9,10,13,14-hexahydro-12H-5,15-(azeno)pyrazolo[4,3-i][1,4,6]oxadiazacyclotetradecin-7(8H)-one: MS (EI) calc'd for C$_{20}$H$_{23}$FN$_5$O$_3$ [M+H]$^+$ 400, found 400; $^1$H-NMR (300 MHz, DMSO): δ 11.72 (d, J=6.9 Hz, 1 H), 9.21 (s, 1 H), 8.12 (s, 1 H), 7.41-7.06 (m, 5 H), 5.29 (d, J=4.8 Hz, 1 H), 4.84-4.80 (m, 1 H), 4.64-4.57 (m, 2 H), 4.05-4.02 (m, 1 H), 3.87-3.82 (m, 1 H), 3.65-3.24 (m, 5 H), 1.44 (t, J=7.1 Hz, 3 H).

Product B: (9S,13S) or (9S,13R)-1-Ethyl-9-(3-fluorophenyl)-13-hydroxy-1,6,9,10,13,14-hexahydro-12H-5,15-(azeno)pyrazolo[4,3-i][1,4,6]oxadiazacyclotetradecin-7(8H)-one, MS (EI) calc'd for C$_{20}$H$_{23}$FN$_5$O$_3$ [M+H]$^+$ 400, found 400; $^1$H-NMR (300 MHz, DMSO): δ 11.55 (d, J=7.8 Hz, 1 H), 9.27 (s, 1 H), 8.01 (s, 1 H), 7.41-7.05 (m, 5 H), 5.23 (d, J=4.8 Hz, 1 H), 4.86-4.40 (m, 4 H), 4.04-4.01 (m, 1 H), 3.64-3.31 (m, 5 H), 1.41 (t, J=7.1 Hz, 3H).

Product C: (9S,13R) or (9S,13S)-1-Ethyl-9-(4-chloro-3-fluorophenyl)-13-hydroxy-1,6,9,10,13,14-hexahydro-12H-5,15-(azeno)pyrazolo[4,3-i][1,4,6]oxadiazacyclotetradecin-7(8H)-one: MS (EI) calc'd for C$_{20}$H$_{22}$ClFN$_5$O$_3$ [M+H]$^+$ 434, found 434; $^1$H-NMR (300 MHz, MeOD): δ 7.98 (s, 1

H), 7.49-7.24 (m, 3 H), 7.04 (s, 1 H), 4.82-4.52 (m, 4 H), 4.14-4.11 (m, 1 H), 3.78-3.61 (m, 5 H), 1.47 (t, J=7.0 Hz, 3 H).

Product D: (9S,13S) or (9S,13R)-1-Ethyl-9-(4-chloro-3-fluorophenyl)-13-hydroxy-1,6,9,10,13,14-hexahydro-12H-5,15-(azeno)pyrazolo[4,3-i][1,4,6]oxadiazacyclotetradecin-7(8H)-one: MS (EI) calc'd for $C_{20}H_{22}ClFN_5O_3$ [M+H]$^+$ 434, found 434; $^1$H-NMR (300 MHz, MeOD): δ 8.00 (s, 1 H), 7.44-7.28 (m, 3 H), 7.06 (s, 1 H), 4.72-4.63 (m, 4 H), 4.10-4.02 (m, 1 H), 3.76-3.54 (m, 4 H), 3.12-3.04 (m, 1 H), 1.51 (t, J=7.0 Hz, 3 H).

Example 55

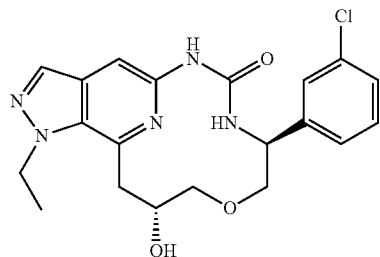 [SMILES: CCn1ncc2cc3nc(c21)C[C@@H](O)COC[C@H](c1cccc(Cl)c1)NC(=O)N3]

(9S,13R)-9-(3-chlorophenyl)-1-ethyl-13-hydroxy-1,6,9,10,13,14-hexahydro-12H-5,15-(azeno)pyrazolo[4,3-i][1,4,6]oxadiazacyclotetradecin-7(8H)-one Example 56

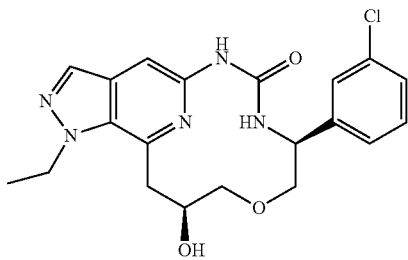 [SMILES: CCn1ncc2cc3nc(c21)C[C@H](O)COC[C@H](c1cccc(Cl)c1)NC(=O)N3]

(9S,13S)-9-(3-chlorophenyl)-1-ethyl-13-hydroxy-1,6,9,10,13,14-hexahydro-12H-5,15-(azeno)pyrazolo[4,3-i][1,4,6]oxadiazacyclotetradecin-7(8H)-one Isomer A: (9S,13R) or (9S,13S)-9-(3-chlorophenyl)-1-ethyl-13-hydroxy-1,6,9,10,13,14-hexahydro-12H-5,15-(azeno)pyrazolo[4,3-i][1,4,6]oxadiazacyclotetradecin-7(8H)-one: MS (EI) calc'd for $C_{20}H_{23}ClN_5O_3$ [M+H]$^+$ 416, found 416; $^1$H-NMR (300 MHz, DMSO-d$_6$): δ ppm 12.71 (d, J=6.0 Hz, 1 H), 9.22 (s, 1 H), 8.12 (s, 1 H), 7.37 (m, 4 H), 7.06 (s, 1 H), 5.29 (d, J=4.8 Hz, 1 H), 4.83 (t, J=3.0 Hz, 1 H), 4.62 (m, 2 H), 4.05 (s, 1 H), 3.84 (m, 1 H), 3.64 (m, 1 H), 3.44 (m, 3 H), 2.72 (m, 1 H), 1.45 (t, J=7.2 Hz 3 H)

Isomer B: (9S,13S) or (9S,13R)-9-(3-chlorophenyl)-1-ethyl-13-hydroxy-1,6,9,10,13,14-hexahydro-12H-5,15-(azeno)pyrazolo[4,3-i][1,4,6]oxadiazacyclotetradecin-7(8H)-one: MS (EI) calc'd for $C_{20}H_{23}ClN_5O_3$ [M+H]$^+$ 416, found 416; $^1$H-NMR (300 MHz, DMSO-d$_6$): δ ppm 12.52 (d, J=6.0 Hz, 1 H), 9.28 (s, 1 H), 8.10 (s, 1 H), 7.24 (m, 4 H), 7.05 (s, 1 H), 5.24 (d, J=4.8 Hz, 1 H), 4.86 (m, 1 H), 4.75 (m, 1 H), 4.61 (m, 1 H), 4.39 (s, 1 H), 4.03 (m, 1 H), 3.56 (m, 4 H), 3.34 (m, 1 H), 1.41 (t, J=7.2 Hz, 3 H).

Example 57

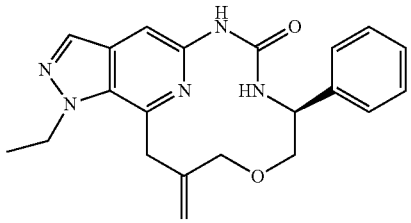 [SMILES: C=C1COC[C@H](c2ccccc2)NC(=O)Nc2cc3cnn(CC)c3c(n2)C1]

(9 S)-1-ethyl-13-methylidene-9-phenyl-1,6,9,10,13,14-hexahydro-12H-5,15-(azeno)pyrazolo[4,3-i][1,4,6]oxadiazacyclotetradecin-7(8H)-one To a suspension of methyl triphenylphosphonium bromide (0.50 g, 1.81 mmol) in dry THF (5 mL) at −70° C. was added N-butyllithium (0.79 mL, 2.5 M in hexane, 1.98 mmol) under a nitrogen atmosphere. After stirring for 20 min, a solution of (9S)-1-ethyl-9-phenyl-1,6,9,10-tetrahydro-12H-5,15-(azeno)pyrazolo[4,3-i][1,4,6]oxadiazacyclotetradecine-7,13(8H,14H)-dione (90 mg, 0.24 mmol), example 43, in dry THF (5 mL) was added dropwise during 5 min at −70° C. The resulting mixture was allowed to warm to 0° C., and then stirred for 1 h at 0° C. and for 1 h ambient temperature. The reaction mixture was then quenched by saturated ammonium chloride (50 mL), extracted with ethyl acetate (50 mL), and washed with brine (50 mL). The organic layer was dried over anhydrous sodium sulfate, and filtered. The filtrate was evaporated under reduced pressure, the residue was purified by Prep-TLC (petroleum ether/ethyl acetate=20:1) to give the desired product (90 mg). The product was further purified by Prep-HPLC with conditions: Column, Sunfire C 18, 19×150 mm; Mobile phase, H$_2$O (0.05% NH$_4$HCO$_3$)/CH$_3$CN (38~58% in 8 min, up to 95% in 2 min; down to 38% in 2 min); Detector, 254 nm, and 220 nm; The desired fraction afforded (9S)-1-ethyl-13-methylidene-9-phenyl-1,6,9,10,13,14-hexahydro-12H-5,15-(azeno)pyrazolo[4,3-i][1,4,6]oxadiazacyclotetradecin-7(8H)-one. MS (EI) calc'd for $C_{21}H_{24}N_5O_2$ [M+H]$^+$ 378, found 378; $^1$H NMR (400 MHz, DMSO-d$_6$): δ 11.22 (d, J=8.4 Hz, 1 H), 9.24 (s, 1 H), 8.11 (s, 1 H), 7.40-7.22 (m, 5 H), 7.03 (s, 1 H), 5.22 (s, 2 H), 4.86 (d, J=7.6 Hz, 1 H), 4.64-4.58 (m, 2 H), 4.31 (d, J=14.0 Hz, 1 H), 4.15-4.00 (m, 4 H), 3.77-3.73 (m, 1 H), 1.42 (t, J=7.0 Hz, 3 H).

Example 58

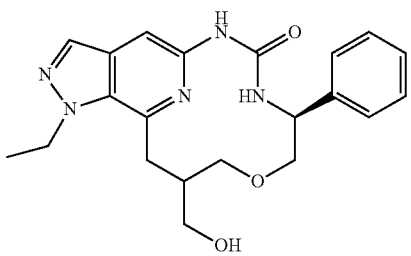 [SMILES: CCn1ncc2cc3nc(c21)CC(CO)COC[C@H](c1ccccc1)NC(=O)N3]

(9 S)-1-ethyl-13-(hydroxymethyl)-9-phenyl-1,6,9,10,13,14-hexahydro-12H-5,15-(azeno)pyrazolo[4,3-i][1,4,6]oxadiazacyclotetradecin-7(8H)-one To a solution of (9S)-1-ethyl-13-methylidene-9-phenyl-1,6,9,10,13,14-hexahydro-12H-5,15-(azeno)pyrazolo[4,3-i][1,4,6]oxadiazacyclotetradecin-7(8H)-one, example 57, (35 mg, 0.037 mmol) in anhydrous THF (10 mL) was added borane-tetrahydrofuran complex (0.4 mL, 1 M in THF, 0.400 mmol) under a nitrogen atmosphere. After stirring at 65° C. for 1 h, the reaction mixture was cooled to 25° C. Water (0.1 mL) was added and followed by aqueous NaOH (0.4 mL, 3 M, 1.200 mmol) and 30% $H_2O_2$ (0.4 mL, 4.57 mmol). The resulting mixture was stirred at 25° C. for 1 h, diluted with brine (30 mL), and extracted with ethyl acetate (30 mL). The organic layer was washed with brine (2×20 mL), dried over anhydrous sodium sulfate, and filtered. The filtrate was evaporated under reduced pressure. The residue was purified by Prep-TLC (DCM/MeOH=20:1) and then by Prep-HPLC with conditions: Column, Sunfire C 18, 19×150 mm; Mobile phase, $H_2O$ (0.05% TFA)/$CH_3CN$ (33~33% in 8 min, up to 95% in 2 min; down to 33% in 2 min); Detector, 254 nm, and 220 nm; The desired fraction afforded (9S)-1-ethyl-13-(hydroxymethyl)-9-phenyl-1,6,9,10,13,14-hexahydro-12H-5,15-(azeno)pyrazolo[4,3-i][1,4,6]oxadiazacyclotetradecin-7(8H)-one. MS (EI) calc'd for $C_{21}H_{26}N_5O_3$ [M+H]$^+$ 396, found 396; $^1$H NMR (400 MHz, DMSO-$d_6$): δ 11.71 (d, J=7.2 Hz, 1 H), 9.16 (s, 1 H), 8.11 (s, 1 H), 7.40-7.23 (m, 5 H), 7.05 (s, 1 H), 4.80 (t, J=3.2 Hz, 1 H), 4.62-4.56 (m, 2 H), 3.80-3.77 (m, 1 H), 3.62-3.51 (m, 3 H), 3.48-3.40 (m, 3 H), 3.25-3.22 (m, 1 H), 3.05-2.99 (m, 1 H), 2.13 (br, 1 H), 1.45 (t, J=7.0 Hz, 3 H).

The ERK2 IC$_{50}$ in nanomolar (nM) for the compounds of the invention, measured according to the assay "Active human ERK2 (hERK2) Activity Assay" described below, is shown in the Example next to the structure or compound name.

Examples 1-58 are another embodiment of the invention.

TABLE

| Structure | IUPAC Name | Exact Mass [M + H]+ |
| --- | --- | --- |
| 3 | (9S,13S)-1-ethyl-13-hydroxy-9-phenyl-1,6,9,10,13,14-hexahydro-12H-5,15-(azeno)pyrazolo[4,3-i][1,4,6]oxadiazacyclotetradecin-7(8H)-one 13.62 nM | Calc'd 382, found 382 |
| 4 | (9S,13R)-1-ethyl-13-hydroxy-9-phenyl-1,6,9,10,13,14-hexahydro-12H-5,15-(azeno)pyrazolo[4,3-i][1,4,6]oxadiazacyclotetradecin-7(8H)-one 3.535 nM | Calc'd 382, found 382 |
| 13 | (9R,10R)-1-ethyl-10-(hydroxymethyl)-9-phenyl-1,6,9,10,13,14-hexahydro-12H-5,15-(azeno)pyrazolo[4,3-i][1,4,6]oxadiazacyclotetradecin-7(8H)-one 757.3 nM | Calc'd 396, found 396 |
| 14 | (9S,10S)-1-ethyl-10-(hydroxymethyl)-9-phenyl-1,6,9,10,13,14-hexahydro-12H-5,15-(azeno)pyrazolo[4,3-i][1,4,6]oxadiazacyclotetradecin-7(8H)-one 3.443 nM | Calc'd 396, found 396 |

TABLE-continued

| | Structure | IUPAC Name | Exact Mass [M + H]+ |
|---|---|---|---|
| 11 | 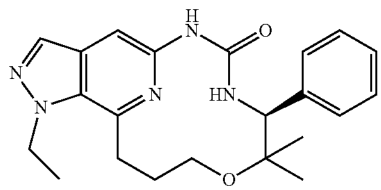 [SMILES: CCn1ncc2cc3nc(c21)CCCOC(C)(C)[C@H](c1ccccc1)NC(=O)N3] | (9S)-1-ethyl-10,10-dimethyl-9-phenyl-1,6,9,10,13,14-hexahydro-12H-5,15-(azeno)pyrazolo[4,3-i][1,4,6]oxadiazacyclotetradecin-7(8H)-one 16.22 nM | Calc'd 394, found 394 |
| 12 | 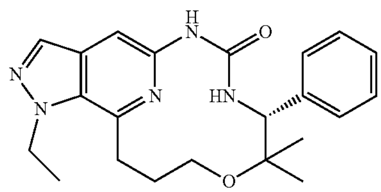 [SMILES: CCn1ncc2cc3nc(c21)CCCOC(C)(C)[C@@H](c1ccccc1)NC(=O)N3] | (9R)-1-ethyl-10,10-dimethyl-9-phenyl-1,6,9,10,13,14-hexahydro-12H-5,15-(azeno)pyrazolo[4,3-i][1,4,6]oxadiazacyclotetradecin-7(8H)-one 733.9 nM | Calc'd 394, found 394 |
| 5 | 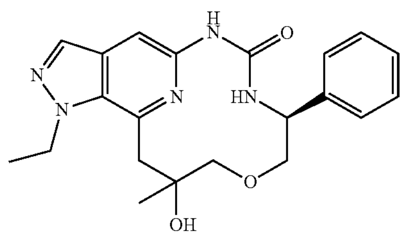 [SMILES: CCn1ncc2cc3nc(c21)CC(C)(O)COC[C@H](c1ccccc1)NC(=O)N3] | (9S)-1-ethyl-13-hydroxy-13-methyl-9-phenyl-1,6,9,10,13,14-hexahydro-12H-5,15-(azeno)pyrazolo[4,3-i][1,4,6]oxadiazacyclotetradecin-7(8H)-one 114.3 nM | Calc'd 396, found 396 |
| 7 | 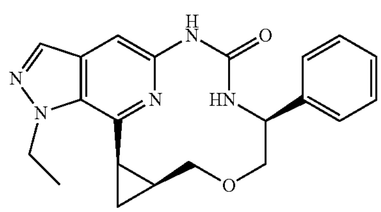 [SMILES: CCn1ncc2cc3nc(c21)[C@@H]1C[C@@H]1COC[C@H](c1ccccc1)NC(=O)N3] | (9S,12aS,13aR)-1-ethyl-9-phenyl-1,6,9,10,12,12a,13,13a-octahydro-5,14-(azeno)cyclopropa[1]pyrazolo[4,3-i][1,4,6]oxadiazacyclotetradecin-7(8H)-one 11.56 nM | Calc'd 378, found 378 |
| 8 | 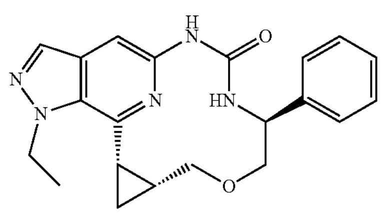 [SMILES: CCn1ncc2cc3nc(c21)[C@H]1C[C@H]1COC[C@H](c1ccccc1)NC(=O)N3] | (9S,12aR,13aS)-1-ethyl-9-phenyl-1,6,9,10,12,12a,13,13a-octahydro-5,14-(azeno)cyclopropa[1]pyrazolo[4,3-i][1,4,6]oxadiazacyclotetradecin-7(8H)-one 49.74 nM | Calc'd 378, found 378 |
| 9 | 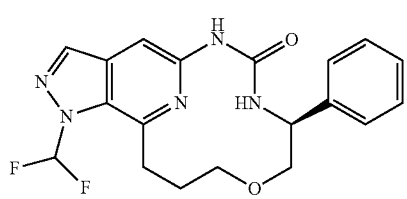 [SMILES: O=C1Nc2cc3cnn(C(F)F)c3c(n2)CCCOC[C@H](c2ccccc2)N1] | (9S)-1-(difluoromethyl)-9-phenyl-1,6,9,10,13,14-hexahydro-12H-5,15-(azeno)pyrazolo[4,3-i][1,4,6]oxadiazacyclotetradecin-7(8H)-one 12.47 nM | Calc'd 388, found 388 |
| 10 | 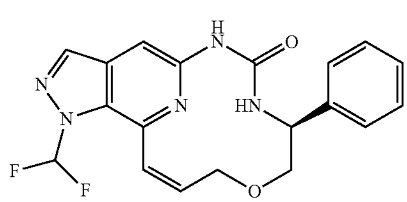 [SMILES: O=C1Nc2cc3cnn(C(F)F)c3c(n2)/C=C\COC[C@H](c2ccccc2)N1] | (9S,13Z)-1-(difluoromethyl)-9-phenyl-1,6,9,10-tetrahydro-12H-5,15-(azeno)pyrazolo[4,3-i][1,4,6]oxadiazacyclotetradecin-7(8H)-one 4.163 nM | Calc'd 386, found 386 |

TABLE-continued

| Structure | IUPAC Name | Exact Mass [M + H]+ |
|---|---|---|
| 22 | (9S)-1-methyl-9-phenyl-1,6,9,10,13,14-hexahydro-12H-5,15-(azeno)pyrazolo[4,3-i][1,4,6,12]oxatriazacyclotetradecin-7(8H)-one 7.913 nM | Calc'd 353, found 353 |
| 1 | (9S)-1-ethyl-9-phenyl-1,6,9,10,13,14-hexahydro-12H-5,15-(azeno)pyrazolo[4,3-i][1,4,6]oxadiazacyclotetradecin-7(8H)-one 8.791 nM | Calc'd 366, found 366 |
| 20 | 1,14-dimethyl-9-phenyl-1,6,9,10,11,12,13,14-octahydro-5,15-(azeno)pyrazolo[4,3-i][1,3,9]triazacyclotetradecin-7(8H)-one 85.72 nM | Calc'd 365, found 365 |
| 23 | (9S,10S)-10-hydroxy-1-methyl-9-phenyl-1,6,8,9,10,11,12,13-octahydro-7H-5,15-(azeno)pyrazolo[3,4-c][1,7,9]oxadiazacyclotetradecin-7-one 45.09 nM | Calc'd 368, found 368 |
| 24 | (9S,10R)-10-hydroxy-1-methyl-9-phenyl-1,6,8,9,10,11,12,13-octahydro-7H-5,15-(azeno)pyrazolo[3,4-c][1,7,9]oxadiazacyclotetradecin-7-one 190.3 nM | Calc'd 368, found 368 |
| 18 | 1-ethyl-9-phenyl-1,6,9,10,11,12,13,14-octahydro-5,15-(azeno)pyrazolo[4,3-f][1,3,9]triazacyclotetradecin-7(8H)-one 15.74 nM | Calc'd 365, found 365 |
| 25 | (9S,10S)-1-ethyl-10-hydroxy-9-phenyl-1,6,8,9,10,11,12,13-octahydro-7H-5,15-(azeno)pyrazolo[3,4-c][1,7,9]oxadiazacyclotetradecin-7-one 24.3 nM | Calc'd 382, found 382 |
| 26 | (9S,10R)-1-ethyl-10-hydroxy-9-phenyl-1,6,8,9,10,11,12,13-octahydro-7H-5,15-(azeno)pyrazolo[3,4-c][1,7,9]oxadiazacyclotetradecin-7-one 118.2 nM | Calc'd 382, found 382 |

| | Structure | IUPAC Name | Exact Mass [M + H]+ |
|---|---|---|---|
| 15 | 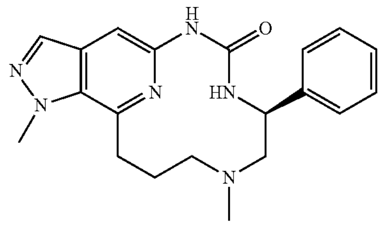 [SMILES: CN1CCCc2nc(cc3cnn(C)c23)NC(=O)N[C@@H](c2ccccc2)C1] | (9S)-1,11-dimethyl-9-phenyl-1,6,9,10,11,12,13,14-octahydro-5,15-(azeno)pyrazolo[3,4-k][1,3,6]triazacyclotetradecin-7(8H)-one 56.84 nM | Calc'd 365, found 365 |
| 28 | 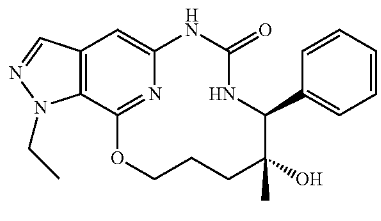 [SMILES: CCn1ncc2cc3nc(c21)OCCC[C@@](C)(O)[C@H](c1ccccc1)NC(=O)N3] | (9S,10R)-1-ethyl-10-hydroxy-10-methyl-9-phenyl-1,6,8,9,10,11,12,13-octahydro-7H-5,15-(azeno)pyrazolo[3,4-c][1,7,9]oxadiazacyclotetradecin-7-one 144.5 nM | Calc'd 396, found 396 |
| 6 | 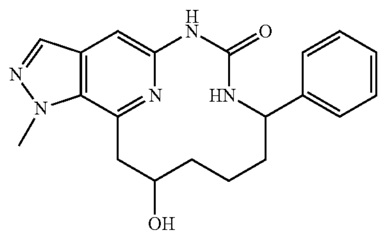 [SMILES: Cn1ncc2cc3nc(c21)CC(O)CCCC(c1ccccc1)NC(=O)N3] | 13-hydroxy-1-methyl-9-phenyl-1,6,9,10,11,12,13,14-octahydro-5,15-(azeno)pyrazolo[4,3-f][1,3]diazacyclotetradecin-7(8H)-one | Calc'd 366, found 366 |
| 21 | 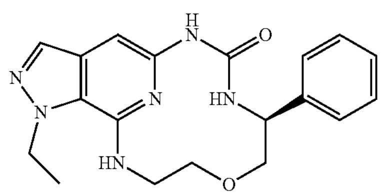 [SMILES: CCn1ncc2cc3nc(c21)NCCOC[C@H](c1ccccc1)NC(=O)N3] | (9S)-1-ethyl-9-phenyl-1,6,9,10,13,14-hexahydro-12H-5,15-(azeno)pyrazolo[4,3-i][1,4,6,12]oxatriazacyclotetradecin-7(8H)-one 5.014 nM | Calc'd 367, found 367 |
| 27 | 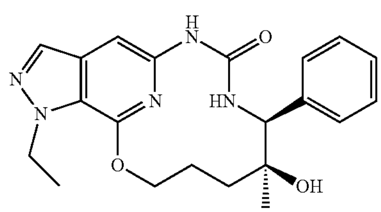 [SMILES: CCn1ncc2cc3nc(c21)OCCC[C@](C)(O)[C@H](c1ccccc1)NC(=O)N3] | (9S,10S)-1-ethyl-10-hydroxy-10-methyl-9-phenyl-1,6,8,9,10,11,12,13-octahydro-7H-5,15-(azeno)pyrazolo[3,4-c][1,7,9]oxadiazacyclotetradecin-7-one 147.7 nM | Calc'd 396, found 396 |
| 32 | 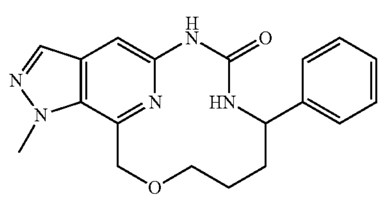 [SMILES: Cn1ncc2cc3nc(c21)COCCCC(c1ccccc1)NC(=O)N3] | 1-methyl-9-phenyl-1,6,9,10,11,12-hexahydro-5,15-(azeno)pyrazolo[4,3-k][1,6,8]oxadiazacyclotetradecin-7(8H,14H)-one 50.87 nM | Calc'd 352, found 352 |
| 16 | 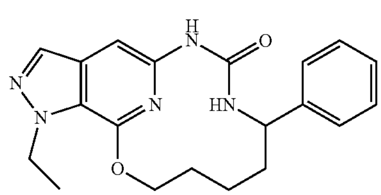 [SMILES: CCn1ncc2cc3nc(c21)OCCCCC(c1ccccc1)NC(=O)N3] | 1-ethyl-9-phenyl-1,6,8,9,10,11,12,13-octahydro-7H-5,15-(azeno)pyrazolo[3,4-c][1,7,9]oxadiazacyclotetradecin-7-one 85.41 nM | Calc'd 366, found 366 |

| Structure | IUPAC Name | Exact Mass [M + H]+ |
|---|---|---|
| 33 | 1,13-dimethyl-9-phenyl-1,6,9,10,11,12,13,14-octahydro-5,15-(azeno)pyrazolo[3,4-k][1,3,8]triazacyclotetradecin-7(8H)-one 275.7 nM | Calc'd 365, found 365 |
| 2 | (9S)-1-methyl-9-phenyl-1,6,9,10,13,14-hexahydro-12H-5,15-(azeno)pyrazolo[4,3-i][1,4,6]oxadiazacyclotetradecin-7(8H)-one 10.22 nM | Calc'd 352, found 352 |
| 19 | (9R)-1-methyl-9-phenyl-1,6,9,10,11,12,13,14-octahydro-5,15-(azeno)pyrazolo[4,3-f][1,3,9]triazacyclotetradecin-7(8H)-one 9.324 nM | Calc'd 351, found 351 |
| 29 | (9S)-1-methyl-9-phenyl-1,6,9,10,12,13-hexahydro-5,15-(azeno)pyrazolo[4,3-i][1,12,4,6]dioxadiazacyclotetradecin-7(8H)-one 49.23 nM | Calc'd 354, found 354 |
| 37 | 1-(3-methoxypropyl)-9-phenyl-1,6,9,10-tetrahydro-5,16-(azeno)-14,11-(metheno)pyrazolo[4,3-l][1,2,3,7,9]pentaazacyclopentadecin-7(8H,15H)-one 240.6 nM | Calc'd 433, found 433 |
| 17 | (9R)-1-methyl-9-phenyl-1,6,8,9,10,11,12,13-octahydro-7H-5,15-(azeno)pyrazolo[3,4-c][1,7,9]oxadiazacyclotetradecin-7-one 58.87 nM | Calc'd 352, found 352 |
| 30 | 1-methyl-9-phenyl-1,6,9,10,11,12,13,14-octahydro-5,15-(azeno)pyrazolo[4,3-f][1,3]diazacyclotetradecin-7(8H)-one 230.2 nM | Calc'd 350, found 350 |

| | Structure | IUPAC Name | Exact Mass [M + H]+ |
|---|---|---|---|
| 36 | | 1-(2-methoxyethyl)-9-phenyl-1,6,9,10-tetrahydro-5,16-(azeno)-14,11-(metheno)pyrazolo[4,3-1][1,2,3,7,9]pentaazacyclopentadecin-7(8H,15H)-one 415.8 nM | Calc'd 419, found 419 |
| 38 | | 1-(2-methylpyridin-4-yl)-9-phenyl-1,6,9,10-tetrahydro-5,16-(azeno)-14,11-(metheno)pyrazolo[4,3-1][1,2,3,7,9]pentaazacyclopentadecin-7(8H,15H)-one 87.31 nM | Calc'd 452, found 452 |
| 39 | | 1-(2-methylpyridin-4-yl)-9-phenyl-1,6,9,10-tetrahydro-5,16-(azeno)-14,11-(metheno)pyrazolo[4,3-1][1,2,3,7,9]pentaazacyclopentadecin-7(8H,15H)-one 232.8 nM | Calc'd 452, found 452 |
| 40 | | 1,18-dimethyl-9-phenyl-1,6,9,10-tetrahydro-5,16-(azeno)-14,11-(metheno)pyrazolo[4,3-1][1,2,3,7,9]pentaazacyclopentadecin-7(8H,15H)-one 1954 nM | Calc'd 389, found 389 |
| 31 | | 1-methyl-9-phenyl-1,6,9,10,11,12,13,14-octahydro-5,15-(azeno)pyrazolo[3,4-k][1,3,8]triazacyclotetradecin-7(8H)-one 832.2 nM | Calc'd 351, found 351 |
| 35 | | (9R)-1-methyl-9-phenyl-1,6,9,10-tetrahydro-5,16-(azeno)-14,11-(metheno)pyrazolo[4,3-1][1,2,3,7,9]pentaazacyclopentadecin-7(8H,15H)-one 69.4 nM | Calc'd 375, found 375 |

TABLE-continued

| | Structure | IUPAC Name | Exact Mass [M + H]+ |
|---|---|---|---|
| 34 | 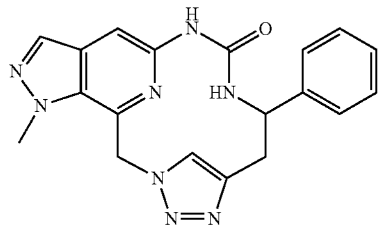 [SMILES: Cn1ncc2cc3nc(c21)Cn1cc(nn1)CC(c1ccccc1)NC(=O)N3] | 1-methyl-9-phenyl-1,6,9,10-tetrahydro-5,16-(azeno)-14,11-(metheno)pyrazolo[4,3-1][1,2,3,7,9]pentaazacyclopentadecin-7(8H,15H)-one 89.89 nM | Calc'd 375, found 375 |
| 41 | 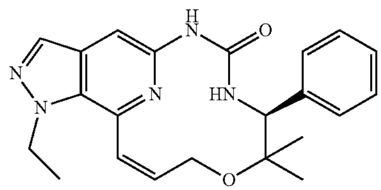 [SMILES: CCn1ncc2cc3nc(c21)/C=C\COC(C)(C)[C@H](c1ccccc1)NC(=O)N3] | (9S,13Z)-1-Ethyl-10,10-dimethyl-9-phenyl-1,6,9,10-tetrahydro-12H-5,15-(azeno)pyrazolo[4,3-i][1,4,6]oxadiazacyclotetradecin-7(8H)-one 633.5 nM | Calc'd 392, found 392 |
| 42 | 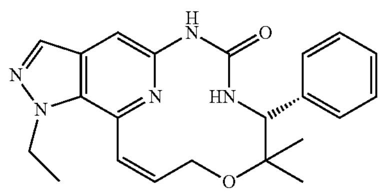 | (9R,13Z)-1-Ethyl-10,10-dimethyl-9-phenyl-1,6,9,10-tetrahydro-12H-5,15-(azeno)pyrazolo[4,3-i][1,4,6]oxadiazacyclotetradecin-7(8H)-one 230.2 nM | Calc'd 392, found 392 |
| 43 | 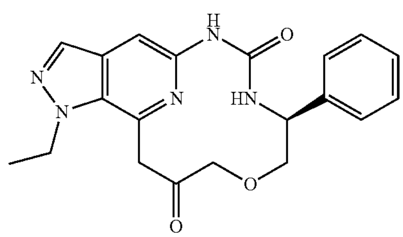 [SMILES: CCn1ncc2cc3nc(c21)CC(=O)COC[C@H](c1ccccc1)NC(=O)N3] | 9S)-1-ethyl-9-phenyl-1,6,9,10-tetrahydro-12H-5,15-(azeno)pyrazolo[4,3-i][1,4,6]oxadiazacyclotetradecine-7,13(8H,14H)-dione 11.21 nM | Calc'd 380, found 380 |
| 44 | 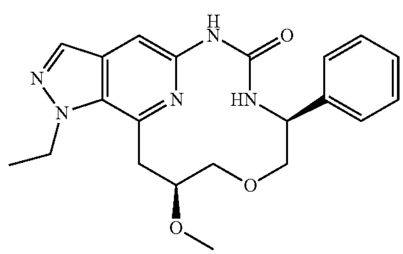 [SMILES: CCn1ncc2cc3nc(c21)C[C@H](OC)COC[C@H](c1ccccc1)NC(=O)N3] | (9R,13R)-1-Ethyl-13-methoxy-9-phenyl-1,6,9,10,13,14-hexahydro-12H-5,15-(azeno)pyrazolo[4,3-i][1,4,6]oxadiazacyclotetradecin-7(8H)-one 32.78 nM | Calc'd 396, found 396; |
| 45 | 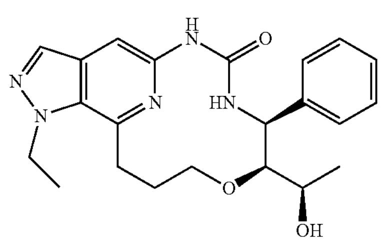 [SMILES: CCn1ncc2cc3nc(c21)CCCO[C@H]([C@@H](C)O)[C@H](c1ccccc1)NC(=O)N3] | (9S,10S)-1-ethyl-10-[(1R)-1-hydroxyethyl]-9-phenyl-1,6,9,10,13,14-hexahydro-12H-5,15-(azeno)pyrazolo[4,3-i][1,4,6]oxadiazacyclotetradecin-7(8H)-one 287.4 nM | Calc'd 410, found 410 |
| 46 | 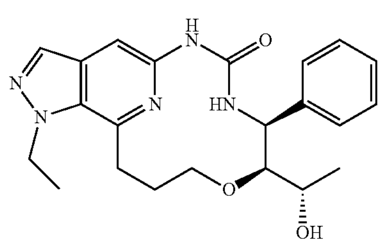 [SMILES: CCn1ncc2cc3nc(c21)CCCO[C@H]([C@H](C)O)[C@H](c1ccccc1)NC(=O)N3] | (9S,10S)-1-ethyl-10-[(1S)-1-hydroxyethyl]-9-phenyl-1,6,9,10,13,14-hexahydro-12H-5,15-(azeno)pyrazolo[4,3-i][1,4,6]oxadiazacyclotetradecin-7(8H)-one 48.45 nM | Calc'd 410, found 410 |

TABLE-continued

| Structure | IUPAC Name | Exact Mass [M + H]+ |
|---|---|---|
| 47 | (9R,10R)-1-ethyl-10-[(1R)-1-hydroxyethyl]-9-phenyl-1,6,9,10,13,14-hexahydro-12H-5,15-(azeno)pyrazolo[4,3-i][1,4,6]oxadiazacyclotetradecin-7(8H)-one 687.3 nM | Calc'd 410, found 410 |
| 48 | (9R,10R)-1-ethyl-10-[(1S)-1-hydroxyethyl]-9-phenyl-1,6,9,10,13,14-hexahydro-12H-5,15-(azeno)pyrazolo[4,3-i][1,4,6]oxadiazacyclotetradecin-7(8H)-one 4.107 nM | Calc'd 410, found 410 |
| 55 | (9S,13R)-9-(3-chlorophenyl)-1-ethyl-13-hydroxy-1,6,9,10,13,14-hexahydro-12H-5,15-(azeno)pyrazolo[4,3-i][1,4,6]oxadiazacyclotetradecin-7(8H)-one 3.835 nM | Calc'd 416, found 416 |
| 56 | (9S,13S)-9-(3-chlorophenyl)-1-ethyl-13-hydroxy-1,6,9,10,13,14-hexahydro-12H-5,15-(azeno)pyrazolo[4,3-i][1,4,6]oxadiazacyclotetradecin-7(8H)-one 0.9958 nM | Calc'd 416, found 416 |
| 52 | (9S,13S)-1-ethyl-9-(3-fluorophenyl)-13-hydroxy-1,6,9,10,13,14-hexahydro-12H-5,15-(azeno)pyrazolo[4,3-i][1,4,6]oxadiazacyclotetradecin-7(8H)-one 14.49 nM | Calc'd 400, found 400 |
| 51 | (9S,13R)-1-ethyl-9-(3-fluorophenyl)-13-hydroxy-1,6,9,10,13,14-hexahydro-12H-5,15-(azeno)pyrazolo[4,3-i][1,4,6]oxadiazacyclotetradecin-7(8H)-one 3.907 | Calc'd 400, found 400 |

TABLE-continued

| | Structure | IUPAC Name | Exact Mass [M + H]+ |
|---|---|---|---|
| 50 | 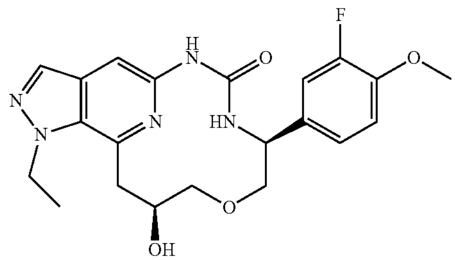 [SMILES: CCn1ncc2cc3nc(c21)C[C@H](O)COC[C@H](c1ccc(OC)c(F)c1)NC(=O)N3] | (9S,13S)-1-ethyl-9-(3-fluoro-4-methoxyphenyl)-13-hydroxy-1,6,9,10,13,14-hexahydro-12H-5,15-(azeno)pyrazolo[4,3-i][1,4,6]oxadiazacyclotetradecin-7(8H)-one 6.284 nM | Calc'd 430, found 430 |
| 49 | 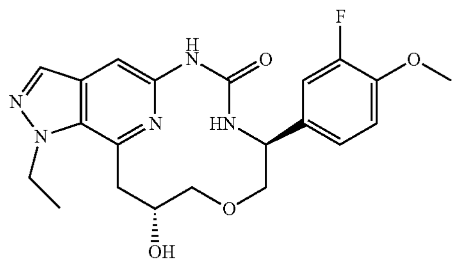 [SMILES: CCn1ncc2cc3nc(c21)C[C@@H](O)COC[C@H](c1ccc(OC)c(F)c1)NC(=O)N3] | (9S,13R)-1-ethyl-9-(3-fluoro-4-methoxyphenyl)-13-hydroxy-1,6,9,10,13,14-hexahydro-12H-5,15-(azeno)pyrazolo[4,3-i][1,4,6]oxadiazacyclotetradecin-7(8H)-one 3.4 nM | Calc'd 430, found 430 |
| 58 | 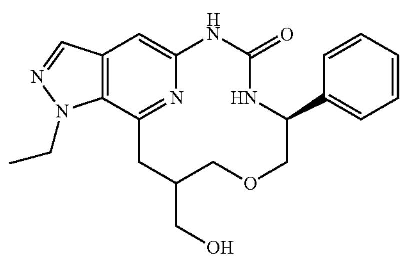 [SMILES: CCn1ncc2cc3nc(c21)CC(CO)COC[C@H](c1ccccc1)NC(=O)N3] | (9S)-1-ethyl-13-(hydroxymethyl)-9-phenyl-1,6,9,10,13,14-hexahydro-12H-5,15-(azeno)pyrazolo[4,3-i][1,4,6]oxadiazacyclotetradecin-7(8H)-one 5.088 nM | Calc'd 396, found 396 |
| 57 | 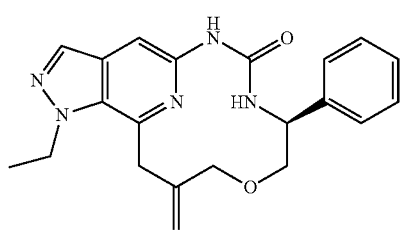 [SMILES: C=C1COC[C@H](c2ccccc2)NC(=O)Nc2cc3cnn(CC)c3c(n2)C1] | (9S)-1-ethyl-13-methylidene-9-phenyl-1,6,9,10,13,14-hexahydro-12H-5,15-(azeno)pyrazolo[4,3-i][1,4,6]oxadiazacyclotetradecin-7(8H)-one 5.172 nM | Calc'd 378, found 378 |
| 54 | 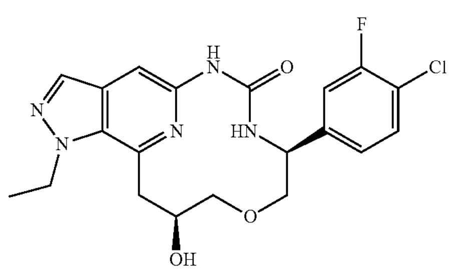 [SMILES: CCn1ncc2cc3nc(c21)C[C@H](O)COC[C@H](c1ccc(Cl)c(F)c1)NC(=O)N3] | (9S,13S)-1-ethyl-9-(4-chloro-3-fluorophenyl)-13-hydroxy-1,6,9,10,13,14-hexahydro-12H-5,15-(azeno)pyrazolo[4,3-i][1,4,6]oxadiazacyclotetradecin-7(8H)-one 5.088 nM | Calc'd 396, found 396 |
| 53 | 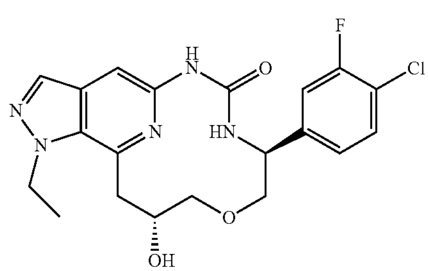 [SMILES: CCn1ncc2cc3nc(c21)C[C@@H](O)COC[C@H](c1ccc(Cl)c(F)c1)NC(=O)N3] | (9S,13R)-1-ethyl-9-(4-chloro-3-fluorophenyl)-13-hydroxy-1,6,9,10,13,14-hexahydro-12H-5,15-(azeno)pyrazolo[4,3-i][1,4,6]oxadiazacyclotetradecin-7(8H)-one 3.907 nM | Calc'd 400, found 400 |

Assays

Active human ERK2 (hERK2) Activity Assay:

Activated ERK2 activity was determined in an IMAP-FP assay (Molecular Devices). Using this assay format, the potency ($IC_{50}$) of each compound was determined from a 10 point (1:3 serial dilution, 3 µM starting compound concentration) titration curve using the following outlined procedure. To each well of a black Corning 384-well plate (Corning Catalog #3575), 7.5 nL of compound (3333 fold dilution in final assay volume of 25 µL) was dispensed, followed by the addition of 15 µL of kinase buffer (tween containing kinase buffer, Molecular Devices) containing 0.0364 ng/mL (0.833 nM) of phosphorylated active hERK2 enzyme. Following a 15 minute compound & enzyme incubation, each reaction was initiated by the addition of 10 µL kinase buffer containing 2.45 µM ERK2 IMAP substrate peptides and 75 µM ATP. The final reaction in each well of 25 µL consists of 0.5 nM hERK2, 900 nM unlabeled peptide, 80 nM labeled-peptide, and 30 µM ATP. Phosphorylation reactions were allowed to proceed for 60 minutes and were immediately quenched by the addition of 60 µL IMAP detection beads (1:1000 dilutions) in IMAP binding buffer (Molecular Devices) with 24 mM NaCl. Plates were read on EnVision reader after 60 minutes binding equilibration using Fluorescence Polarization protocol (Perkin Elmer). The ERK2 $IC_{50}$ in nanomolar (nM) for the compounds of the invention is shown in the examples next to the structure name.

While the present invention has been described in conjunction with the specific examples set forth above, many alternatives, modifications and variations thereof will be apparent to those of ordinary skill in the art. All such alternatives, modifications and variations are intended to fall within the spirit and scope of the present invention.

What is claimed is:
1. A compound of formula I

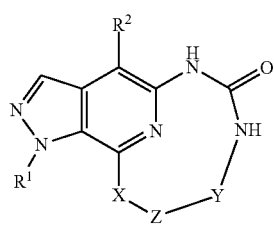

I or a pharmaceutically acceptable salt thereof, wherein
$R^1$ is
1) —$C_{1-4}$alkyl, unsubstituted or substituted with $R^{1'}$, wherein $R^{1'}$ is independently selected from halogen and $OC_{1-4}$ alkyl,
2) 6-membered unsaturated heterocycle having 1 N atom, wherein the heterocycle is unsubstituted or substituted on any ring atom with $C_{1-4}$ alkyl,
3) 6-membered unsaturated carbocycle unsubstituted or substituted on any ring atom with $C_{1-4}$ alkyl, or,
4) —C(O)$C_{1-4}$ alkyl;
$R^2$ is
hydrogen or halogen;
—X—Z is
1) —$C_{1-4}$ alkylene-Z, wherein the alkylene is unsubstituted or substituted with OH, =$CH_2$, —$C_{1-4}$ alkyl, —$C_{1-4}$ alkylene OH, or —$OC_{1-4}$ alkyl,

2)

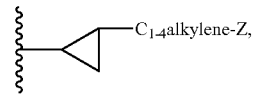

3) —$C_{1-4}$ alkenylene-Z,
4) —$NR^3C_{1-4}$ alkylene-Z,
5) —$OC_{1-4}$ alkylene-Z,
6) —$CH_2NR^3C_{1-4}$ alkylene-Z,
7) —$CH_2C(O)C_{1-4}$ alkylene-Z, or
8) —$CH_2OC_{1-4}$ alkylene-Z;
Z—Y is
O—Y, $C_{1-4}$ alkylene-Y, $NR^3$—Y or

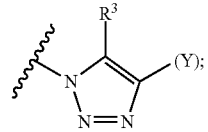

NH—Y is
NH—CH($C_6H_3R^4R^5$)$C_{1-4}$ alkylene-, where $C_{1-4}$ alkylene is unsubstituted or independently mono- or di-substituted with $R^6$;
$R^3$ is independently
hydrogen or $C_{1-4}$ alkyl;
$R^4$ is
hydrogen or halogen;
$R^5$ is
hydrogen or —$OC_{1-4}$ alkyl; and
$R^6$ is
OH or $C_{1-4}$ alkyl wherein alkyl is unsubstituted or substituted with OH.

2. A compound of claim 1, or a pharmaceutically acceptable salt thereof, wherein
$R^1$ is
1) —$C_{1-4}$ alkyl, unsubstituted or substituted with $R^{1'}$, wherein $R^{1'}$ is independently selected from F and $OC_{1-4}$ alkyl, or
2) 6-membered unsaturated heterocycle having 1 N atom, wherein the heterocycle is unsubstituted or substituted on any ring atom with $C_{1-4}$ alkyl,
$R^2$ is
hydrogen;
—X—Z is
1) —$C_{1-4}$ alkylene-Z, wherein the alkylene is unsubstituted or substituted with OH, =$CH_2$, —$CH_3$, —$CH_2OH$, or —$OC_{1-4}$ alkyl,
2)

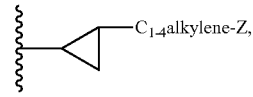

3) —$C_{1-4}$ alkenylene-Z,
4) —$NR^3C_{1-4}$ alkylene-Z,
5) —$OC_{1-4}$ alkylene-Z,
6) —$CH_2NR^3C_{1-4}$ alkylene-Z,
7) —$CH_2C(O)C_{1-4}$ alkylene-Z, or
8) —$CH_2OC_{1-4}$ alkylene-Z;

Z—Y is
O—Y, $C_{1-4}$ alkylene-Y, $NR^3$—Y or

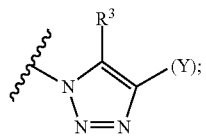

NH—Y is
NH—CH($C_6H_3R^4R^5$)$C_{1-4}$ alkylene-, where $C_{1-4}$ alkylene is unsubstituted or independently mono- or di-substituted with $R^6$;
$R^3$ is independently
hydrogen or $C_{1-4}$ alkyl;
$R^4$ is
hydrogen or F;
$R^5$ is
hydrogen or —$OC_{1-4}$ alkyl; and
$R^6$ is
OH or $C_{1-4}$ alkyl wherein alkyl is unsubstituted or substituted with OH.

3. A compound of claim 2, or a pharmaceutically acceptable salt thereof, wherein
$R^1$ is
—$CH_2CH_3$, —$CHF_2$, —$CH_3$, —$(CH_2)_3OCH_3$, —$(CH_2)_2OCH_3$, or

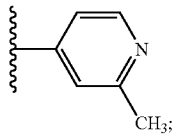

$R^2$ is
hydrogen;

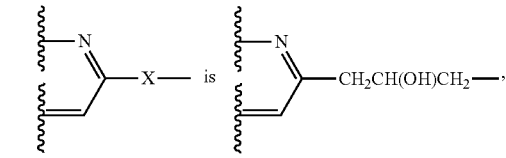

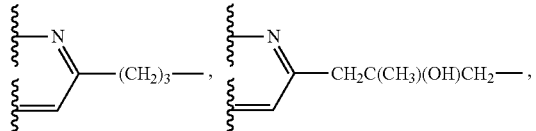

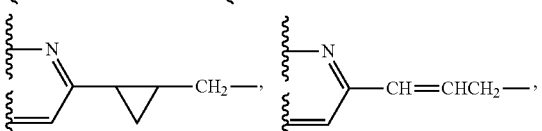

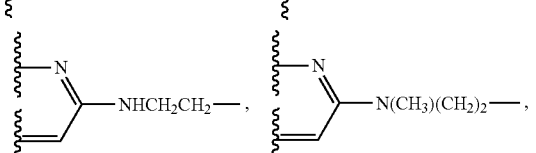

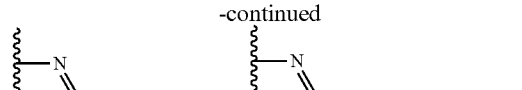

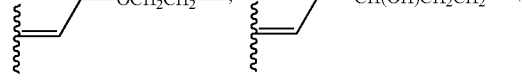

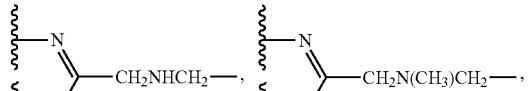

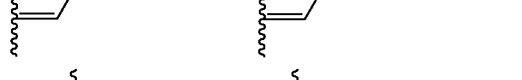

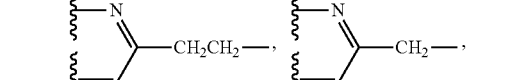

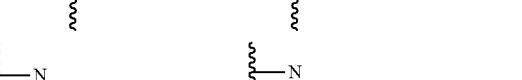

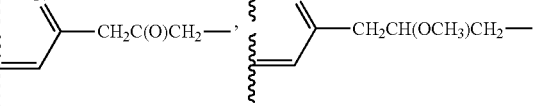

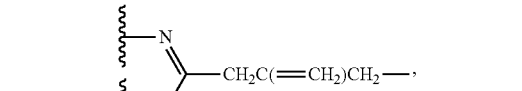

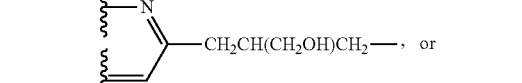

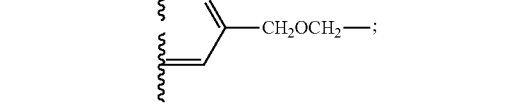

Z is
O, $CH_2$, $N(CH_3)$,

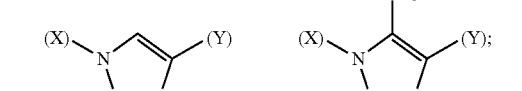

and
NH—Y— is
NH—CH($C_6H_5$)$CH_2$—, NH—CH($C_6H_5$)CH(OH),
NH—CH($C_6H_5$)C(OH)($CH_3$)—,
NH—CH($C_6H_5$)C($CH_3$)$_2$—, NH—CH($C_6H_5$)CH(CH(OH)($CH_3$)), or
NH—CH($C_6H_3$(F)($OCH_3$))$CH_2$—.

4. A compound of claim 3, or a pharmaceutically acceptable salt thereof, selected from the group consisting of
- (9S,13S)-1-ethyl-13-hydroxy-9-phenyl-1,6,9,10,13,14-hexahydro-12H-5,15-(azeno)pyrazolo[4,3-i][1,4,6]oxadiazacyclotetradecin-7(8H)-one,
- (9S,13R)-1-ethyl-13-hydroxy-9-phenyl-1,6,9,10,13,14-hexahydro-12H-5,15-(azeno)pyrazolo[4,3-i][1,4,6]oxadiazacyclotetradecin-7(8H)-one,
- (9R,10R)-1-ethyl-10-(hydroxymethyl)-9-phenyl-1,6,9,10,13,14-hexahydro-12H-5,15-(azeno)pyrazolo[4,3-i][1,4,6]oxadiazacyclotetradecin-7(8H)-one,
- (9S,10S)-1-ethyl-10-(hydroxymethyl)-9-phenyl-1,6,9,10,13,14-hexahydro-12H-5,15-(azeno)pyrazolo[4,3-i][1,4,6]oxadiazacyclotetradecin-7(8H)-one,
- (9S)-1-ethyl-10,10-dimethyl-9-phenyl-1,6,9,10,13,14-hexahydro-12H-5,15-(azeno)pyrazolo[4,3-i][1,4,6]oxadiazacyclotetradecin-7(8H)-one,
- (9R)-1-ethyl-10,10-dimethyl-9-phenyl-1,6,9,10,13,14-hexahydro-12H-5,15-(azeno)pyrazolo[4,3-i][1,4,6]oxadiazacyclotetradecin-7(8H)-one,
- (9S)-1-ethyl-13-hydroxy-13-methyl-9-phenyl-1,6,9,10,13,14-hexahydro-12H-5,15-(azeno)pyrazolo[4,3-i][1,4,6]oxadiazacyclotetradecin-7(8H)-one,
- (9S,12aS,13aR)-1-ethyl-9-phenyl-1,6,9,10,12,12a,13,13a-octahydro-5,14-(azeno)cyclopropa[1]pyrazolo[4,3-i][1,4,6]oxadiazacyclotetradecin-7(8H)-one,
- (9S,12aR,13aS)-1-ethyl-9-phenyl-1,6,9,10,12,12a,13,13a-octahydro-5,14-(azeno)cyclopropa[1]pyrazolo[4,3-i][1,4,6]oxadiazacyclotetradecin-7(8H)-one,
- (9S)-1-(difluoromethyl)-9-phenyl-1,6,9,10,13,14-hexahydro-12H-5,15-(azeno)pyrazolo[4,3-i][1,4,6]oxadiazacyclotetradecin-7(8H)-one,
- (9S,13Z)-1-(difluoromethyl)-9-phenyl-1,6,9,10-tetrahydro-12H-5,15-(azeno)pyrazolo[4,3-i][1,4,6]oxadiazacyclotetradecin-7(8H)-one,
- (9S)-1-methyl-9-phenyl-1,6,9,10,13,14-hexahydro-12H-5,15-(azeno)pyrazolo[4,3-i][1,4,6,12]oxatriazacyclotetradecin-7(8H)-one,
- (9S)-1-ethyl-9-phenyl-1,6,9,10,13,14-hexahydro-12H-5,15-(azeno)pyrazolo[4,3-i][1,4,6]oxadiazacyclotetradecin-7(8H)-one,
- 1,14-dimethyl-9-phenyl-1,6,9,10,11,12,13,14-octahydro-5,15-(azeno)pyrazolo[4,3-f][1,3,9]triazacyclotetradecin-7(8H)-one,
- (9S,10S)-10-hydroxy-1-methyl-9-phenyl-1,6,8,9,10,11,12,13-octahydro-7H-5,15-(azeno)pyrazolo[3,4-c][1,7,9]oxadiazacyclotetradecin-7-one,
- (9S,10R)-10-hydroxy-1-methyl-9-phenyl-1,6,8,9,10,11,12,13-octahydro-7H-5,15-(azeno)pyrazolo[3,4-c][1,7,9]oxadiazacyclotetradecin-7-one,
- 1-ethyl-9-phenyl-1,6,9,10,11,12,13,14-octahydro-5,15-(azeno)pyrazolo[4,3-f][1,3,9]triazacyclotetradecin-7(8H)-one,
- (9S,10S)-1-ethyl-10-hydroxy-9-phenyl-1,6,8,9,10,11,12,13-octahydro-7H-5,15-(azeno)pyrazolo[3,4-c][1,7,9]oxadiazacyclotetradecin-7-one,
- (9S,10R)-1-ethyl-10-hydroxy-9-phenyl-1,6,8,9,10,11,12,13-octahydro-7H-5,15-(azeno)pyrazolo[3,4-c][1,7,9]oxadiazacyclotetradecin-7-one,
- (9S)-1,11-dimethyl-9-phenyl-1,6,9,10,11,12,13,14-octahydro-5,15-(azeno)pyrazolo[3,4-k][1,3,6]triazacyclotetradecin-7(8H)-one,
- (9S,10R)-1-ethyl-10-hydroxy-10-methyl-9-phenyl-1,6,8,9,10,11,12,13-octahydro-7H-5,15-(azeno)pyrazolo[3,4-c][1,7,9]oxadiazacyclotetradecin-7-one,
- 13-hydroxy-1-methyl-9-phenyl-1,6,9,10,11,12,13,14-octahydro-5,15-(azeno)pyrazolo[4,3-f][1,3]diazacyclotetradecin-7(8H)-one,
- (9S)-1-ethyl-9-phenyl-1,6,9,10,13,14-hexahydro-12H-5,15-(azeno)pyrazolo[4,3-i][1,4,6,12]oxatriazacyclotetradecin-7(8H)-one,
- (9S,10S)-1-ethyl-10-hydroxy-10-methyl-9-phenyl-1,6,8,9,10,11,12,13-octahydro-7H-5,15-(azeno)pyrazolo[3,4-c][1,7,9]oxadiazacyclotetradecin-7-one,
- 1-methyl-9-phenyl-1,6,9,10,11,12-hexahydro-5,15-(azeno)pyrazolo[4,3-k][1,6,8]oxadiazacyclotetradecin-7(8H,14H)-one,
- 1-ethyl-9-phenyl-1,6,8,9,10,11,12,13-octahydro-7H-5,15-(azeno)pyrazolo[3,4-c][1,7,9]oxadiazacyclotetradecin-7-one,
- 1,13-dimethyl-9-phenyl-1,6,9,10,11,12,13,14-octahydro-5,15-(azeno)pyrazolo[3,4-k][1,3,8]triazacyclotetradecin-7(8H)-one,
- (9S)-1-methyl-9-phenyl-1,6,9,10,13,14-hexahydro-12H-5,15-(azeno)pyrazolo[4,3-i][1,4,6]oxadiazacyclotetradecin-7(8H)-one,
- (9R)-1-methyl-9-phenyl-1,6,9,10,11,12,13,14-octahydro-5,15-(azeno)pyrazolo[4,3-f][1,3,9]triazacyclotetradecin-7(8H)-one,
- (9S)-1-methyl-9-phenyl-1,6,9,10,12,13-hexahydro-5,15-(azeno)pyrazolo[4,3-i][1,12,4,6]dioxadiazacyclotetradecin-7(8H)-one,
- 1-(3-methoxypropyl)-9-phenyl-1,6,9,10-tetrahydro-5,16-(azeno)-14,11-(metheno)pyrazolo[4,3-l][1,2,3,7,9]pentaazacyclopentadecin-7(8H,15H)-one,
- (9R)-1-methyl-9-phenyl-1,6,8,9,10,11,12,13-octahydro-7H-5,15-(azeno)pyrazolo[3,4-c][1,7,9]oxadiazacyclotetradecin-7-one,
- 1-methyl-9-phenyl-1,6,9,10,11,12,13,14-octahydro-5,15-(azeno)pyrazolo[4,3-f][1,3]diazacyclotetradecin-7(8H)-one,
- 1-(2-methoxyethyl)-9-phenyl-1,6,9,10-tetrahydro-5,16-(azeno)-14,11-(metheno)pyrazolo[4,3-l][1,2,3,7,9]pentaazacyclopentadecin-7(8H,15H)-one,
- 1-(2-methylpyri din-4-yl)-9-phenyl-1,6,9,10-tetrahydro-5,16-(azeno)-14,11-(metheno)pyrazolo[4,3-l][1,2,3,7,9]pentaazacyclopentadecin-7(8H,15H)-one,
- 1-(2-methylpyri din-4-yl)-9-phenyl-1,6,9,10-tetrahydro-5,16-(azeno)-14,11-(metheno)pyrazolo[4,3-l][1,2,3,7,9]pentaazacyclopentadecin-7(8H,15H)-one,
- 1,18-dimethyl-9-phenyl-1,6,9,10-tetrahydro-5,16-(azeno)-14,11-(metheno)pyrazolo[4,3-l][1,2,3,7,9]pentaazacyclopentadecin-7(8H,15H)-one,
- 1-methyl-9-phenyl-1,6,9,10,11,12,13,14-octahydro-5,15-(azeno)pyrazolo[3,4-k][1,3,8]triazacyclotetradecin-7(8H)-one,
- (9R)-1-methyl-9-phenyl-1,6,9,10-tetrahydro-5,16-(azeno)-14,11-(metheno)pyrazolo[4,3-l][1,2,3,7,9]pentaazacyclopentadecin-7(8H,15H)-one,
- 1-methyl-9-phenyl-1,6,9,10-tetrahydro-5,16-(azeno)-14,11-(metheno)pyrazolo[4,3-l][1,2,3,7,9]pentaazacyclopentadecin-7(8H,15H)-one,
- (9S, 13Z)-1-Ethyl-10,10-dimethyl-9-phenyl-1,6,9,10-tetrahydro-12H-5,15-(azeno)pyrazolo[4,3-i][1,4,6]oxadiazacyclotetradecin-7(8H)-one,
- (9R, 13Z)-1-Ethyl-10,10-dimethyl-9-phenyl-1,6,9,10-tetrahydro-12H-5,15-(azeno)pyrazolo[4,3-i][1,4,6]oxadiazacyclotetradecin-7(8H)-one,
- (9S)-1-ethyl-9-phenyl-1,6,9,10-tetrahydro-12H-5,15-(azeno)pyrazolo[4,3-i][1,4,6]oxadiazacyclotetradecine-7,13(8H,14H)-dione, (9R,13R)-1-Ethyl-13-methoxy-9-phenyl-1,6,9,10,13,14-hexahydro-12H-5,15-(azeno)pyrazolo[4,3-i][1,4,6]oxadiazacyclotetradecin-7(8H)-one, (9S,10S)-1-ethyl-10-[(1R)-1-hydroxyethyl]-9-phenyl-1,6,9,10,13,14-hexahydro-12H-5,15-(azeno)pyrazolo[4,3-i][1,4,6]oxadiazacycl otetradecin-7(8H)-one, (9S,10S)-1-ethyl-10-[(1S)-1-hydroxyethyl]-9-phenyl-1,6,9,10,13,14-hexahydro-12H-5,15-(azeno)pyrazolo[4,3-i][1,4,6]oxadiazacyclotetradecin-7(8H)-one, (9R,10R)-1-ethyl-10-[(1R)-1-hydroxyethyl]-9-phenyl-1,6,9,10,13,14-hexahydro-12H-5,15-(azeno)pyrazolo[4,3-i][1,4,6]oxadiazacyclotetradecin-7(8H)-one, (9R,10R)-1-ethyl-10-[(1S)-1-hydroxyethyl]-9-phenyl-1,6,9,10,13,14-hexahydro-12H-5,15-(azeno)pyrazolo[4,3-i][1,4,6]oxadiazacyclotetradecin-7(8H)-one, (9S,13R)-9-(3-chlorophenyl)-1-ethyl-13-hydroxy-1,6,9,10,13,14-hexahydro-12H-5,15-(azeno)pyrazolo[4,3-i][1,4,6]oxadiazacyclotetradecin-7(8H)-one, (9S,13S)-9-(3-chlorophenyl)-1-ethyl-13-hydroxy-1,6,9,10,13,14-hexahydro-12H-5,15-(azeno)pyrazolo[4,3-i][1,4,6]oxadiazacyclotetradecin-7(8H)-one, (9S,13S)-1-ethyl-9-(3-fluorophenyl)-13-hydroxy-1,6,9,10,13,14-hexahydro-12H-5,15-(azeno)pyrazolo[4,3-i][1,4,6]oxadiazacyclotetradecin-7(8H)-one, (9S,13R)-1-ethyl-9-(3-fluorophenyl)-13-hydroxy-1,6,9,10,13,14-hexahydro-12H-5,15-(azeno)pyrazolo[4,3-i][1,4,6]oxadiazacyclotetradecin-7(8H)-one, (9S,13S)-1-ethyl-9-(3-fluoro-4-methoxyphenyl)-13-hydroxy-1,6,9,10,13,14-hexahydro-12H-5,15-(azeno)pyrazolo[4,3-i][1,4,6]oxadiazacyclotetradecin-7(8H)-one, (9S,13R)-1-ethyl-9-(3-fluoro-4-methoxyphenyl)-13-hydroxy-1,6,9, 10,13,14-hexahydro-12H-5,15-(azeno)pyrazolo[4,3-i][1,4,6]oxadiazacyclotetradecin-7(8H)-one, (9S)-1-ethyl-13-(hydroxymethyl)-9-phenyl-1,6,9,10,13,14-hexahydro-12H-5,15-(azeno)pyrazolo[4,3-i][1,4,6]oxadiazacyclotetradecin-7(8H)-one, (9S)-1-ethyl-13-methylidene-9-phenyl-1,6,9,10,13,14-hexahydro-12H-5,15-(azeno)pyrazolo[4,3-i][1,4,6]oxadiazacyclotetradecin-7(8H)-one, (9S)-1-ethyl-13-(hydroxymethyl)-9-phenyl-1,6,9,10,13,14-hexahydro-12H-5,15-(azeno)pyrazolo[4,3-i][1,4,6]oxadiazacyclotetradecin-7(8H)-one, and (9S,13R)-1-ethyl-9-(3-fluorophenyl)-13-hydroxy-1,6,9,10,13,14-hexahydro-12H-5,15-(azeno)pyrazolo[4,3-i][1,4,6]oxadiazacyclotetradecin-7(8H)-one.

5. A composition comprising a compound of claim 1 and a pharmaceutically acceptable carrier.

6. A method for treating non-small cell lung cancer, pancreatic cancer, colorectal cancer, kidney cancer, hepatocellular carcinoma, and melanoma comprising administering to a patient in need there of a composition of claim 5.

* * * * *